United States Patent
Zitvogel et al.

(10) Patent No.: US 9,593,376 B2
(45) Date of Patent: Mar. 14, 2017

(54) NATURAL KILLER P30 (NKP30) DYSFUNCTION AND THE BIOLOGICAL APPLICATIONS THEREOF

(75) Inventors: Laurence Zitvogel, Paris (FR); Nicolas Delahaye, La Hulpe (BE)

(73) Assignees: INSTITUT GUSTAVE ROUSSY, Villejuif (FR); INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 458 days.

(21) Appl. No.: 12/994,192

(22) PCT Filed: Jun. 2, 2009

(86) PCT No.: PCT/EP2009/056741
§ 371 (c)(1),
(2), (4) Date: Nov. 23, 2010

(87) PCT Pub. No.: WO2009/147137
PCT Pub. Date: Dec. 10, 2009

(65) Prior Publication Data
US 2011/0104136 A1    May 5, 2011

(30) Foreign Application Priority Data
Jun. 2, 2008 (EP) .................... 08305223

(51) Int. Cl.
*C12Q 1/68* (2006.01)
*C07H 21/04* (2006.01)

(52) U.S. Cl.
CPC ..... *C12Q 1/6886* (2013.01); *C12Q 2600/106* (2013.01); *C12Q 2600/136* (2013.01); *Y10T 436/143333* (2015.01)

(58) Field of Classification Search
CPC ...... C12N 15/1044; C12N 2795/14011; C12N 15/1068; C12N 15/62; C12N 15/1065; C12N 15/1089; C12N 15/52; C12N 2799/021; C12N 15/113; C12N 15/1136; C12N 15/8261; C12N 15/1137; C12N 15/8271; C12N 15/8273; C12N 15/8274; C12N 15/8279; C12N 15/8285; C12N 15/8286; C12N 15/8289; C12N 7/00; C12N 9/2462; C12Q 1/6886; C12Q 2600/106; C12Q 2600/136
See application file for complete search history.

(56) References Cited

U.S. PATENT DOCUMENTS

2008/0153877 A1*  6/2008  Adimoolam ......... A61K 31/164
                                                    514/320

FOREIGN PATENT DOCUMENTS

WO    WO 02/08287      1/2002
WO    WO 2006/124668   11/2006

OTHER PUBLICATIONS

Delahaye, Nicolas et al. Microbes and Infection 2007 vol. 9 pp. 160-166.*
Hollyoake (Mol Biol Evol 2005 vol. 22 No. 8 pp. 1661-1672).*
Whitehead, Andrew et al. Variation in tissue specific gene expression among natural populations. Genome Biology 2005 vol. 6 Issue 2 Article R13.*
Hoshikawa, Yasushit et al. Hypoxia induces different genes in the lungs of rats compared with mice. Physical Genomics 2003 vol. 12 pp. 209-219.*
Sato, M. et al. "Identification of novel single nucleotide substitutions in the NKp30 gene expressed in human natural killer cells" *Tissue Antigens*, 2001, pp. 255-258, vol. 58, XP-002494077.
Pende, D. et al. "Identification and Molecular Characterization of NKp30, a Novel Triggering Receptor Involved in Natural Cytotoxicity Mediated by Human Natural Killer Cells" *J. Exp. Med.*, Nov. 15, 1999, pp. 1505-1516, vol. 190, No. 10, XP-002167575.
Castriconi, R. et al. "Transforming growth factor β1 inhibits expression for NKp30 and NKG2D receptors: Consequences for the NK-mediated killing of dendritic cells" *PNAS*, Apr. 1, 2003, pp. 4120-4125, vol. 100, No. 7, XP-002494078.
Gore, S. D. "Inhibitors of signaling in myelodysplastic syndrome" *Best Practice & Research Clinical Haematology*, 2004, pp. 613-622, vol. 17, No. 4, XP-004603464.
Backman-Petersson, E. et al. "Molecular characterization of the novel rat NK receptor 1C7" *Eur. J. Immunol.*, 2003, pp. 342-351, vol. 33, XP-002494080.
Byrd, A. et al. "Expression Analysis of the Ligands for the Natural Killer Cell Receptors NKp30 and NKp44" *PLOS One*, Dec. 2007, p. e1339 (pp. 1-8), vol. 12, XP-002494079.
Written Opinion in International Application No. PCT/EP2009/056741, Jul. 15, 2009, pp. 1-8.
Gong, J. H. et al. "Characterization of a human cell line (NK-92) with phenotypical and functional characteristics of activated natural killer cells" *Leukemia*, Apr. 1994, pp. 652-658, vol. 8, No. 4.
Yoneda, N. et al. "Detection of Epstein-Barr virus genome in natural-killer-like cell line, YT" *Leukemia*, Feb. 1992, pp. 136-141, vol. 6, No. 2.

* cited by examiner

*Primary Examiner* — Amanda Haney
(74) *Attorney, Agent, or Firm* — Saliwanchik, Lloyd & Eisenschenk

(57) ABSTRACT

The present invention relates to a method of assessing a favorable or, on the contrary, an unfavorable prognosis of a cancer in the subject, which method comprises detecting the presence of a mutated Natural Cytotoxicity-triggering Receptor 3 (NCR3) nucleic acid, an abnormal relative amount of at least one particular Natural Killer p30 (NKp30) RNA transcript isoform, and/or an abnormal Natural Killer p30 (NKp30) expression or activity of at least one particular NKp30 protein isoform in a sample from the subject, the presence of mutated NCR3 nucleic acid, abnormal relative amount of at least one particular NKp30 RNA transcript isoform, or abnormal expression or activity of at least one particular NKp30 protein isoform being indicative of the prognosis of cancer in the subject.

6 Claims, 24 Drawing Sheets
(4 of 24 Drawing Sheet(s) Filed in Color)

NATURAL KILLER P30 (NKP30) DYSFUNCTION AND THE BIOLOGICAL APPLICATIONS THEREOF

CROSS-REFERENCE TO RELATED APPLICATION

This application is the U.S. national stage application of International Patent Application No. PCT/EP2009/056741, filed Jun. 2, 2009.

The Sequence Listing for this application is labeled "Seq-List.txt" which was created on Nov. 22, 2010 and is 33 KB. The entire contents of the sequence listing is incorporated herein by reference in its entirety.

The present disclosure generally relates to the fields of genetics, immunology and medicine. The inventors more particularly disclose the identification of a human gene which can be used to determine the prognosis of a cancer in a subject, the sensitivity of a subject to a treatment of cancer before any treatment, or the efficacy of a treatment of cancer after a given period of time. Said human gene may further be used in the prevention or treatment of cancer, as well as for the screening of therapeutically active drugs.

The present disclosure more specifically relates to an altered or abnormal Natural Cytotoxicity-triggering Receptor 3 (NCR3) gene responsible for an altered NCR3 or NKp30 gene expression leading in particular to an abnormal (relative) amount of at least one particular Natural Killer p30 (NKp30) RNA transcript isoform, and/or at least one abnormal NKp30 receptor (NKp30 protein) isoform expression or activity, said abnormal gene, transcript isoforms and protein isoforms representing novel targets for therapeutic intervention.

BACKGROUND

Combating cancer efficiently relies on pharmaceutical compounds directly targeting tumor cells or boosting host defense against said cells. Although several anti-cancer therapies are proposed, amongst which feature chemotherapy [anthracyclines, such as doxycycline (DOX), oxaliplatinum (herein called PLAT) and cis-platinum (herein called PLAT) and tyrosine kinase inhibitors are considered as the most efficient cytotoxic agents of the oncologist armamentarium] and radiotherapy [X-Rays (XR)], the benefits of said treatments still tends to be insufficient. Since the above mentioned therapies represent the basis of up to 70% of anti-cancer therapies, detection of dysfunctions responsible for a reduced response to said treatments appears critical for patient management.

The emerging problem of therapeutic resistance of tumors underlines the importance to consider, firstly, the efficacy of the treatment on the tumor, and, secondly, the efficacy of the host immune system in the eradication of tumor cells. The inventors herein demonstrate that intrinsic (immune) tumor suppression mechanisms act in synergy with extrinsic tumor suppression mechanisms induced by cancer treatments, and that mutations in genes implicated in the immune response affect these extrinsic tumor suppression mechanisms. The mutational and transcriptional status of said genes constitute a new factor predictive of clinical response to cancer treatments.

Gastrointestinal stromal tumors (GISTs) are the most common mesenchymal tumors of the gastrointestinal tract[1]. GISTs are thought to originate from the neoplastic transformation of the interstitial cells of Cajal, the intestinal pacemaker cells. The true incidence of GISTs remains unknown, but experience from clinical trials suggests an incidence of 4500-6000 new cases per year in the United States[2]. The median age at diagnosis is approximately 58 years.

Historically, GISTs have been targeted by the three traditional cancer therapeutic modalities: surgery, chemotherapy, and radiotherapy. Surgery is effective for patients with resectable disease, but disease may recur in as many as 50% of individuals. Chemotherapy and radiotherapy have shown little efficacy[3]. A major breakthrough occurred in 1998 with the discovery of gain-of-function mutations in the KIT oncogene in GISTs[4]. KIT encodes the transmembrane KIT receptor tyrosine kinase (CD117) that, when activated via binding by its ligand, regulates the intracellular signal transduction process. Constitutive tyrosine kinase activation by mutation results in unregulated cell growth and malignant transformation. More than 90% of GISTs harbour activating KIT mutations[5]. These mutations commonly occur in exon 11 (juxtamembrane domain) in 57-71% of cases, exon 9 (extracellular domain) in 10-18% of cases, exon 13 (tyrosine kinase domain I) in 1-4% of cases, and exon 17 (tyrosine kinase domain II) in 1-4% of cases[1]. Approximately 35% of GISTs lacking KIT mutations have activating mutations in a gene encoding a related receptor tyrosine kinase, the platelet-derived growth factor receptor α (PDGFRA)[6]. PDGFRA mutations have been identified in exon 12 (1-2% of GISTs), exon 18 (2-6%), and exon 14 (<1%)[7]. Identification of KIT and PDGFRA mutations led to the development of specific targeted therapies with tyrosine kinase inhibitors (TKIs). Therapy with the TKIs imatinib mesylate (STI571, Gleevec-Novartis) and sunitinib malate (SU11248, Sutent-Pfizer) is effective for unresectable, metastatic, and recurrent disease[8]. Imatinib selectively inhibits several tyrosine kinases including KIT, PDGFRA, and ABL. Data from a phase II imatinib trial revealed that mutational status of KIT was the most important factor predictive of clinical response to imatinib[8]. Patients with GISTs expressing exon 11 KIT mutants who received imatinib had a substantially higher partial response rate, longer median survival, and less likelihood of progressing than those with GISTs expressing wild-type or exon 9 KIT mutants. Imatinib is a dramatically effective agent, but the duration of its benefits is finite. The second targeted tyrosine kinase inhibitor, sunitinib malate, has been approved for the treatment of imatinib-resistant GISTs after recent encouraging results[9]. However, as explained previously, drug resistance is an increasingly more common phenomenon[10].

Responsible for 15% of all cancer-related deaths in children, neuroblastoma is the most common extracranial malignancy and second most common solid tumor affecting the paediatric population[11]. This cancer of the peripheral sympathetic nervous system is well known for its dichotomous pattern of presentation. Approximately one-half of children have localized tumors that can be cured with surgery alone. A small subset of children under 1 year of age who show disease involving the liver, skin, lymph nodes, or bone marrow have a good prognosis despite the extent of their disease. The remaining children have widespread metastatic disease or quite large, aggressive, localized tumors. These children have a poor long-term survival rate of approximately 30%. The challenge of treating children with neuroblastoma is to increase the survival of the high risk patients while avoiding overtreatment of those with lower risk disease. The standard prognostic indicators of outcome in neuroblastoma are age, stage, and histopathology. Additional chromosomal and molecular markers exist that are beginning to improve the accuracy of risk group assignment and outcome prediction[12].

Among the actors of the anti-tumoral response, natural killer (NK) cells provide innate defence against tumors by virtue of potent capacities to immediately kill cellular targets and produce cytokines such as TNFα and IFNγ[13].

NK cells control tumor growth by preventing the dissemination of metastatic tumors in mice[14]. The relevance of NK cells in human malignancies has been discussed by inventors in a recent *Perspective* written for *Nature Immunol*[15]. Recently published data obtained by inventors established in GIST patients that GIST tumors may be controlled by NK cells during the gold standard therapy with imatinib mesylate (IM). Indeed, IM can promote a c-kit dependent DC/NK cell cross-talk leading to NK cell IFNγ production in both mice and humans[16]. Importantly, the NK cell IFNγ production after 2 months of IM represented an independent predictor of long term survival in advanced GIST treated with IM[17]. Such an enhanced IFNγ production of purified NK cells was achieved after short term ex vivo restimulation with maturing DC, suggesting that NK cells from "immunological responders" had been primed in vivo during the GIST development[18,19]. Despite the ongoing questions regarding their effective role against human cancers, physiologic ligation of NK activating or cytokine receptors and/or blockade of inhibitory receptors can result in NK cell proliferation, trafficking, cytotoxicity, production of chemokines and cytokines and in dendritic cell triggering that can be exploited to harness hematological malignancies and some solid tumors.

The human major histocompatibility complex (MHC) encompasses about four megabases of DNA within the chromosomic region 6p21.3 that was characterized by a high density of polymorphic genes[20,21]. The telomeric end of the class III MHC has been designated as class IV region because it contains genes encoding inflammatory functions such as tumor necrosis factor (TNF) family members, allograft inflammatory factor 1 (AIF1), heat shock 70 kDa protein 1B (HSPA1B), lymphotoxin-α LTA) and -β (LTB), HLA-B associated transcript 3 (BAT3), leucocyte-specific transcript 1 (LST1), and natural cytotoxicity triggering receptor 3 (NCR3/1C7/CD337/NKp30)[22] (cf. FIG. 1). The NCR3 gene is transcribed to several mRNA splice variants, most of which are translated into cell surface molecules of the immunoglobulin superfamily[23-25]. By generating monoclonal antibodies directed against the extracellular domain of the NCR3 gene product, Moretta's group succeeded in defining the cellular distribution of the NCR3 gene product and in characterizing NKp30 as a novel NK cell receptor involved in the killing of tumor cells and dendritic cells[26,27]. It is part of the so-called Natural Cytotoxicity Receptors (NCRs) also including NKp44, NKp46 and NKp80[28]. Beyond its expression in NK cells, NKp30 can be exposed on the surface of IL-15 stimulated umbilical cord T lymphocytes[29] and endometrial epithelial cells[30]. However, in peripheral blood of the adult, the only circulating NKp30-expressing cells are NK cells. In contrast to NKp46, the murine ortholog of NKp30 is a pseudogene (in *Mus musculus* but not in *Mus caroli*)[25,31,32] meaning that there is no suitable mouse model for the exploration of NKp30. However, rats express the gene NCR3 encoding an ortholog protein to NKp30[33] and a transcript is detected in macaques (*M. fascicularis*)[32].

Human NKp30 is a 190 amino-acids transmembrane protein with an extracellular variable-type Ig-like domain containing two putative N-glycosylation sites[26]. Three alternative splices can yield three different intracellular domains (that have 36, 25 and 12 amino acids) depending on which particular exon 4 they utilize[24]. An additional alternative splice can induce the deletion of 25 AA in the extracellular domain leading to the formation of a predicted constant-type Ig-like domain instead of a variable-type Ig-like domain[24,32]. In favour of the presence of multiple forms of NKp30 at the cell surface of NK cells, a western blot using a polyclonal antibody directed against NKp30 reveals a broad band of about 10 kD corresponding possibly to differences in glycosylation but also eventually to alternative protein cores[26]. Although these alternative forms of NKp30 were described, the functional relevance of this observation is not clear yet.

In regard to the role of NKp30 in tumor environment, NKp30 has been involved in the lysis of various tumours in vitro, including carcinomas, neuroblastomas, myeloid and lymphoblastic leukaemias and also in the lysis of various cell lines[26,34,35]. NKp30 is not only pivotal at the effector phase of immune responses (to attack targets) but also at the priming phase of cognate immunity. Indeed, NKp30 is regulating the cross-talk between DC and NK cells. Inventors were the first to describe the capacity of DC to trigger NK cell activation in mice[36] and subsequent work definitely established the bidirectional regulation between these cell types[27,37,38]. Depending on the DC/NK ratio and on the KIR/NKG2A expression on the NK cell side, activated NK cells may either kill or promote the immature DC activation. In both cases, NKp30 is directly involved in the recognition of DC by NK cells. In the latter case (when activated NK cells activate immature DC), NKp30 triggering leads to TNFα and IFNγ release by NK cells, both cytokines participating in the DC maturation process[39]. Hence, the DC/NK cell cross talk appears to be critical to modulate Th1 differentiation[40,41]. Therefore, NKp30 triggering could represent a master regulator of the adaptive immune responses in the lymph nodes.

Recent studies have demonstrated a role of NKp30 in human malaria infection[42,43]. The results suggest that NKp30 is involved in the NK cell-*Plasmodium falciparum*-parasitized red blood cells interaction[42]. This interaction is direct, specific and functional, leading to perforine production and granzyme B release. Moreover, an association has been demonstrated between mild malaria and a mutation located within the NCR3 promoter (NCR3-412 G/C-rs2736191)[43]. This suggests that genetic variation in NKp30 may account for the heterogeneity of human NK cell reactivity to *P. falciparum*-infected erythrocytes[44].

It has been suggested that NKp30 could recognize heparan sulfate residues on the cellular membrane of target cells, either tumor cells or dendritic cells[45]. However, these results were criticized by Warren et al[46]. The group of Angel Porgador tried to settle this controversy by comparing various NKp30Fc recombinant proteins used in these studies. Their findings are that glycosylations on the Fc proteins are important in the recognition of NKp30 ligands and they confirm their original findings that heparan sulfates bind to recombinant NKp30 in in vitro assays[47]. Pogge et al claims that Leukocyte Antigen-B-associated transcript 3 (BAT3) is released by tumor cells and engages NKp30[48]. Byrd et al demonstrated that NKp30 ligands are expressed intracellularly in most cell lines and probably in early endosomal compartments[49].

In summary, strong evidence lack on the exact nature of NKp30 ligand(s), in particular in tumoral environment and in in vivo models.

SUMMARY

A first object herein disclosed resides in methods of assessing the prognosis of a cancer in a subject, the method comprising detecting, in particular in vitro or ex vivo, the presence of a mutated Natural Cytotoxicity-triggering Receptor 3 (NCR3) nucleic acid, an abnormal (relative) amount of at least one particular Natural Killer p30 (NKp30) RNA transcript isoform, and/or an abnormal expression or activity of at least one particular NKp30 protein isoform in a sample from the subject, the presence of said mutated NCR3 nucleic acid, abnormal amount of at least one particular NKp30 RNA transcript isoform, or abnormal expression or activity of at least one particular NKp30 protein isoform being indicative of an unfavourable prognosis of the cancer in said subject.

A particular method of assessing the prognosis of a cancer in a subject, comprises measuring, in particular in vitro or ex vivo, the (relative) amount(s) of NKP30 RNA transcript and/or protein isoforms, in particular of intermediate, short and/or long NKp30 isoforms, such amount(s) being indicative of the course of the cancer and allowing the assessment of the prognosis of the cancer in said subject.

Another object herein disclosed resides in a method of assessing the sensitivity of a subject to a treatment of cancer or the efficacy, in a subject, of a treatment of cancer, comprises measuring, in particular in vitro or ex vivo, the (relative) amount(s) of NKP30 RNA transcript and/or protein isoforms, in particular of intermediate, short and/or long NKp30 isoforms, such amount(s) being indicative of the sensitivity of a subject to a treatment of cancer or of the efficacy, in the subject, of a treatment of cancer.

An abnormal NKp30 protein expression may be the result of an abnormal (relative) amount of at least one particular Natural Killer p30 (NKp30) protein isoform, preferably of the intermediate NKp30 protein isoform, said isoform having a constant or variable Ig-like domain.

In particular embodiments, the detected or measured amount(s), expression or activity are respectively compared to control condition(s) or reference(s) or mean value(s), or to that detected or measured in a control sample.

According to specific embodiments of the above described methods, determined isoforms relative amounts may be selected from the group consisting of the short/intermediate NKp30 isoforms relative amounts, short/long NKp30 isoforms relative amounts, intermediate/long NKp30 isoforms relative amounts, and short/intermediate/long NKp30 isoforms relative amounts.

As revealed by results herein provided (see part B of the experimental section), a (relative) increase of the NKp30 intermediate isoform amount and/or decrease in the NKp30 short and/or long isoforms amounts, measured in a sample of a subject, are indicative of an unfavourable prognosis of the cancer in the subject (subjects herein included in the group identified as "profile B") or of a resistance of the subject to a treatment of cancer.

In particular a (relative) increase of the NKp30 intermediate isoform and decrease in the NKp30 short and long isoforms are indicative of an unfavourable prognosis of the cancer in the subject or of a resistance of the subject to a treatment of cancer.

On the contrary, a (relative) decrease of the NKp30 intermediate isoform and increase in the NKp30 short and/or long isoforms are indicative of a favourable prognosis of the cancer in the subject (subjects herein included in the group identified as "profile A"), or of a positive response of the subject to a treatment of cancer.

It has been indeed herein demonstrated by inventors that the functional NKp30 expression is typically associated to a normal or protective NKp30 isoforms status or profile wherein, in a subject, the relative expression or amount of the NKp30 intermediate isoform is decreased and the relative expression or amount of NKp30 short and/or long isoforms is increased when compared to reference or mean values.

In a particular embodiment, a normal or protective NKp30 isoforms status or profile is a profile wherein the (relative) amount of the NKp30 intermediate isoform is lower than the (relative) amount of the NKp30 short and/or long isoforms.

This means that a subject exhibiting such a protective NKp30 profile will benefit from a natural higher protection against cancer fatal evolution than a subject exhibiting an abnormal NKp30 isoforms status or profile, in particular a profile wherein the relative amount of the NKp30 intermediate isoform is higher than a reference or mean value or than the (relative) amount(s) of the NKp30 short and/or long isoforms.

Particular mutations in the NCR3 gene and expression products are further herein described. These mutations are usable in a method of assessing the prognosis of a cancer in a subject, the sensitivity of a subject to a treatment of cancer or the efficacy, in a subject, of a treatment of cancer. The alleles comprising said mutations represent novel targets for therapeutic intervention.

In an embodiment, the present description thus provides a method of assessing the prognosis of a cancer in a subject, the method comprising detecting the presence, in a sample from the subject, of a mutated NCR3 nucleic acid, of an abnormal NKp30 expression isoforms profile or status, in particular of an abnormal NKp30 RNA transcript expression isoforms profile or status, or of an abnormal NKp30 protein isoform expression or activity.

A particular method of determining or assessing the prognosis of a cancer in a subject, the sensitivity of a subject to a treatment of cancer or the efficacy, in a subject, of a treatment of cancer, comprises the detection of the presence, in a sample from the subject, of a mutated NCR3 sequence comprising a point mutation, preferably a single nucleotide polymorphism (SNP) selected from a SNP leading to the substitution of a guanine (G) to the thymine (T) at position 3571 (3571 G/T) (position relative to ATG start codon) of Seq ID NO: 1 [NC_000006.10 (31668933-31664651)], in a sample from the subject, the detection of the presence of a mutated NCR3 sequence comprising such a point mutation being indicative of an unfavourable prognosis of the cancer in said subject, or of a resistance of the subject to the treatment of cancer.

In a further embodiment, the present description provides a method of determining or assessing the prognosis of a cancer in a subject, the sensitivity of a subject to a treatment of cancer or the efficacy, in a subject, of a treatment of cancer, the method comprising detecting the presence, in a sample from the subject, of a mutated NCR3 nucleic acid sequence comprising a point mutation, preferably a SNP leading to the substitution of a cytosine (C) to the Thymine (T) at position 3790 (3790 T/C) (position relative to ATG start codon) of Seq ID NO: 1 [NC_000006.10 (31668933-31664651)], the detection of the presence of a mutated NCR3 sequence comprising such a point mutation being indicative of an unfavourable prognosis of the cancer in said subject, or of an unfavourable, negative response of the subject to the treatment of cancer, as revealed in part B of the experimental section.

The present application further describes the use of:
(i) a NKp30 RNA transcript encoding a functional NKp30 protein isoform, (ii) (a) functional NKp30 protein isoform(s) and/or (iii) a nucleic acid encoding (a) functional NKp30 protein isoform(s), to prepare a pharmaceutical composition for treating or preventing a cancer in a subject;

a compound or substance capable of restoring a functional NKp30 RNA transcription, to prepare a pharmaceutical composition for treating or preventing a cancer in a subject having a mutated NCR3 nucleic acid, an abnormal (relative) amount of at least one particular NKp30 RNA transcript isoform, or an abnormal expression or activity of at least one particular NKp30 protein isoform;

a compound or substance capable of restoring a functional expression or activity of NKp30 protein isoforms, to prepare a pharmaceutical composition for treating or preventing a cancer in a subject having a mutated NCR3 nucleic acid, an abnormal (relative) amount of at least one particular NKp30 RNA transcript isoform, or an abnormal expression or activity of at least one particular NKp30 protein isoform;

a compound or substance bypassing NKp30 signalling pathway and leading to dendritic cell (DC) maturation, to prepare a pharmaceutical composition for treating or preventing a cancer in a subject having a mutated NCR3 nucleic acid, an abnormal (relative) amount of at least one particular NKp30 RNA transcript isoform, or an abnormal expression or activity of at least one particular NKp30 protein isoform;

a compound or substance bypassing NKp30 signalling pathway and leading to NK cell activation, to prepare a pharmaceutical composition for treating or preventing a cancer in a subject having a mutated NCR3 nucleic acid, an abnormal (relative) amount of at least one particular NKp30 RNA transcript isoform, or an abnormal expression or activity of at least one particular NKp30 protein isoform;

and the corresponding methods of treatment.

The description further provides a method of treating or preventing a cancer in a subject in need thereof, comprising administering to said subject an effective amount of a compound or of compounds as defined above.

In a preferred embodiment, the subject has a mutated Natural Cytotoxicity-triggering Receptor 3 (NCR3) nucleic acid, an abnormal (relative) amount of at least one particular Natural Killer p30 (NKp30) RNA transcript isoform, and/or an abnormal expression or activity of at least one particular NKp30 protein isoform.

In a particular embodiment, the method of treating or preventing a cancer in a subject in need thereof, comprises a modulation of NCR3 transcription (alternative splicing) and/or a modulation, in particular an activation of at least one functional NKp30 protein isoform expression or activity, preferably the short and/or long isoforms of NKp30.

More particularly, methods of treating a subject who carries an abnormal NCR3 gene, in particular mutated alleles of the NCR3 gene, which methods include employing combined therapy, are herein provided. Subjects may thus be treated for example through gene therapy, protein replacement therapy or through the administration of NKp30 protein mimetics, activators and/or inhibitors, such as defined above. At least one of said methods may further be combined to a cancer therapy such as a chemotherapy implying for example administration of an alkylating agent, a therapy implying administration of a tyrosine kinase inhibitor (TKI) or a farnesyl-transferase inhibitor (FTI), a therapy implying administration of PKC inhibitors (such as Gö6983)[50], or a radiotherapy.

An in vitro method for screening a compound useful for preventing or treating a cancer is also described. A particular method comprises determining the ability of a test compound or substance to modulate the expression of NCR3, or the expression or activity of NKp30, preferably of a particular NKp30 RNA transcript or protein isoform or of particular NKp30 isoforms. Another particular method comprises determining the ability of a test compound or substance to mimic, induce, increase or stimulate, or, on the contrary decrease, in vitro, in vivo or ex vivo the expression or activity of a ligand of NKp30, preferably of a particular NKp30 RNA transcript or protein isoform or of particular NKp30 isoforms.

The description further provides, in particular embodiments:

a nucleic acid primer that allows (specific) amplification of a particular NKp30 RNA transcript isoform, or allows to discriminate between short, intermediate and long isoforms and preferably also between constant and variable Ig-like domain isoforms;

a nucleic acid probe that (specifically) hybridizes with a particular NKp30 RNA transcript isoform, or allows to discriminate between short, intermediate and long isoforms and preferably also between constant and variable Ig-like domain isoforms;

an antibody (including derivatives thereof and hybridomas producing said antibody), that (specifically) binds a particular isoform of NKp30 protein or allows to discriminate between short, intermediate and long isoforms and preferably also between constant and variable Ig-like domain isoforms.

The description also provides a kit comprising a primer, probe, and/or antibody as defined above. Such kits may comprise a container or support, and/or reagents to perform an amplification, hybridization or binding reaction.

A particular aspect of this invention resides in compositions of matter comprising primers, probes, and/or antibodies, which are designed to specifically detect at least one isoform selected from the group consisting of a short, an intermediate and a long NKp30 isoform having a variable or constant Ig-like extracellular domain.

DESCRIPTION OF DRAWINGS

The patent or application file contains at least one drawing executed in color. Copies of this patent or patent application publication, with color drawing(s), will be provided by the Office upon request and payment of the necessary fee.

NCR3: Natural cytotoxicity-triggering receptor 3; LST1: Leucocyte specific transcript 1; LTB: Lymphotoxin β; TNF: Tumor necrosis factor; LTA: Lymphotoxin α; UTR: Untranslated region; SNP: Single nucleotide polymorphism.

Figure 2:
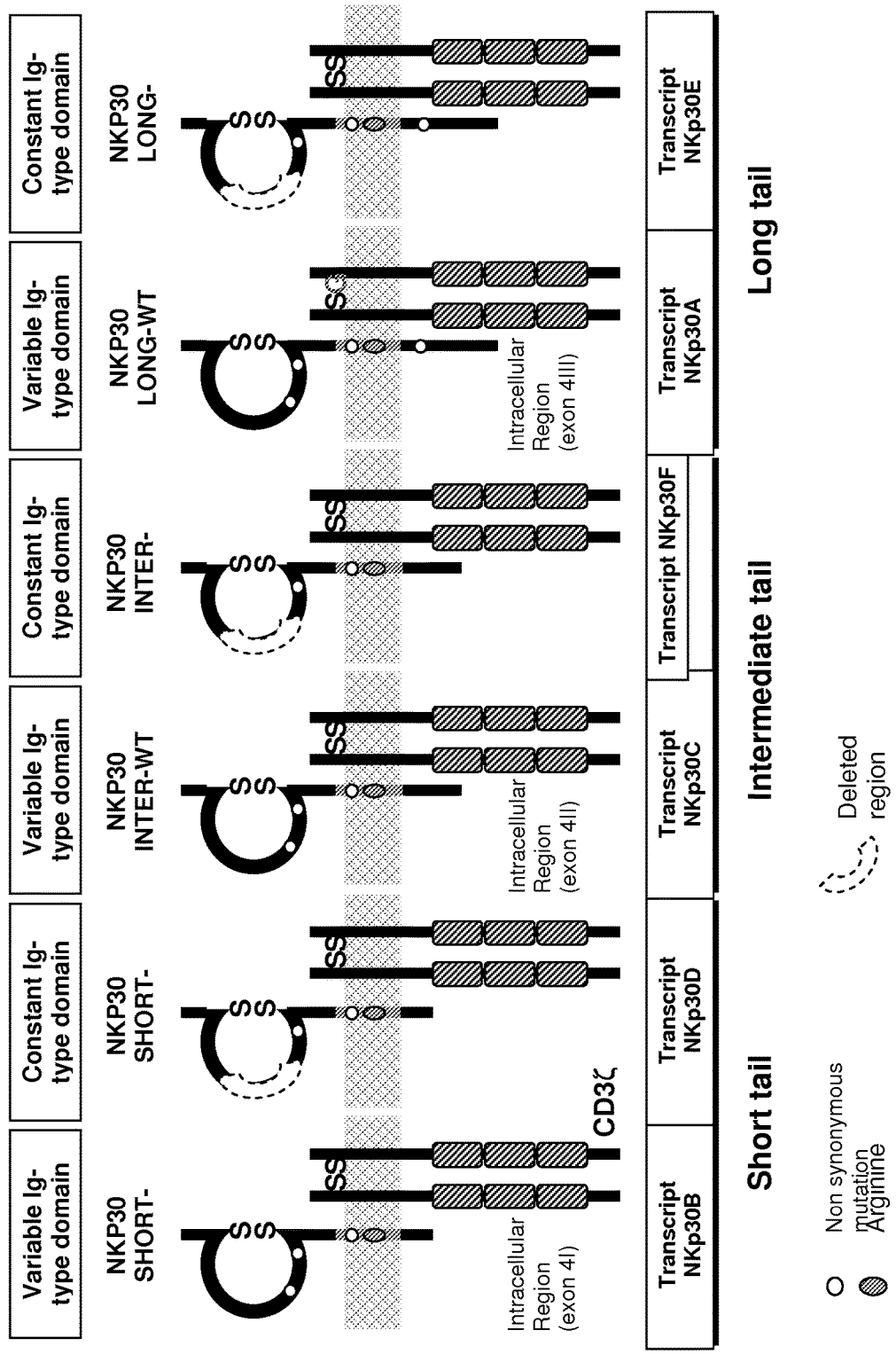

FIG. 2. The six alternative splice forms of NKP30 receptor

Figure 3:
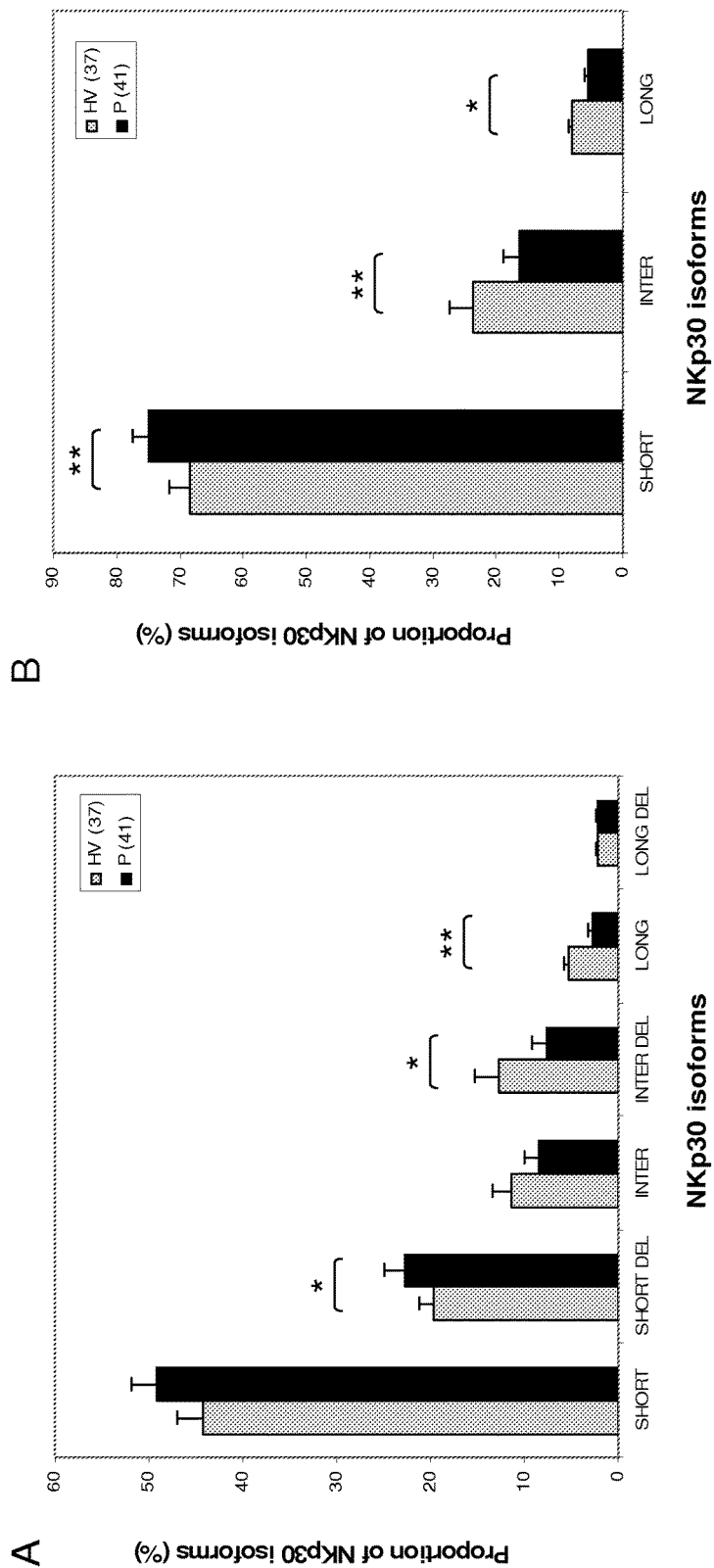

FIG. 3. Comparison of proportions of NKP30 isoforms in GIST patients and healthy volunteers (part A of experimental section)

(A) Proportions of the six isoforms were compared between 41 GIST patients (P) and 37 healthy volunteers (HV).

NKp30 isoform proportions are shown as the ratio of the relative quantities of each isoform and the total quantity of the six isoforms.

(B) Proportions of the SHORT-, INTER- and LONG-tail isoforms were compared between 41 GIST patients and 37 healthy volunteers.

NKp30 isoform proportions are shown as the ratio of the sum of WT—(variable Ig-like) and DEL—(constant Ig-like) extracellular domain relative quantities for each intracellular domain and the total quantity of the six isoforms. Median values±standard error were represented. The Mann-Withney test was used for statistical analyses. *:P<0.05-:P<0.01-*:P<0.001

Figure 4:
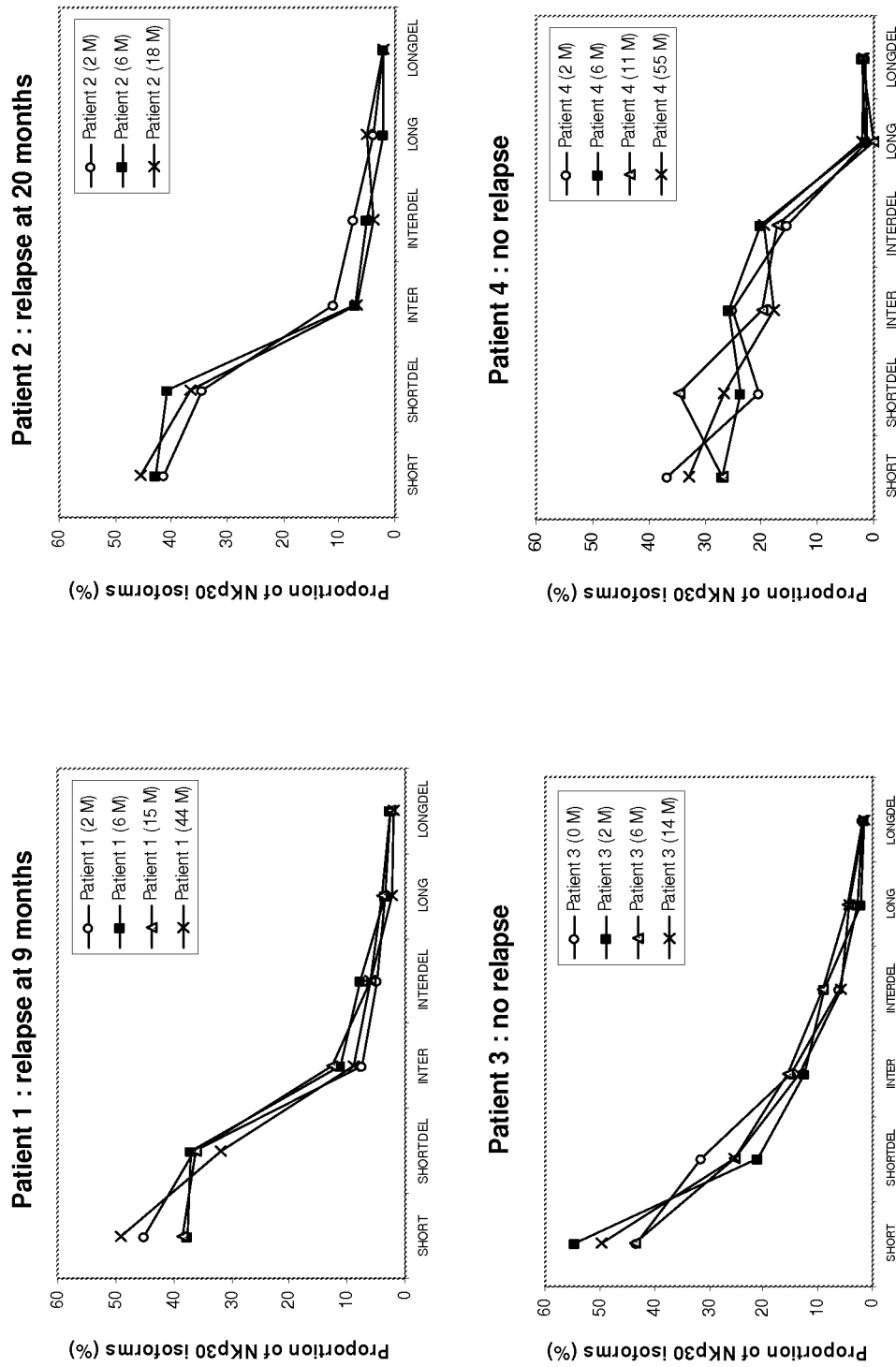

FIG. 4. Representation of NKp30 transcriptional profile intra-individual stability in four GIST patients during the course of treatment Proportions of the six isoforms were compared during the course of GLEEVEC [imatinib mesylate (STI571)] treatment in 4 GIST patients to evaluate the intra-individual stability of NKP30 transcriptional profile. NKp30 isoform proportions are shown as the ratio of the relative quantities of each isoform and the total quantity of the six isoforms. For each patient, the numbers in brackets represent the time post-treatment in months.

Figure 5:
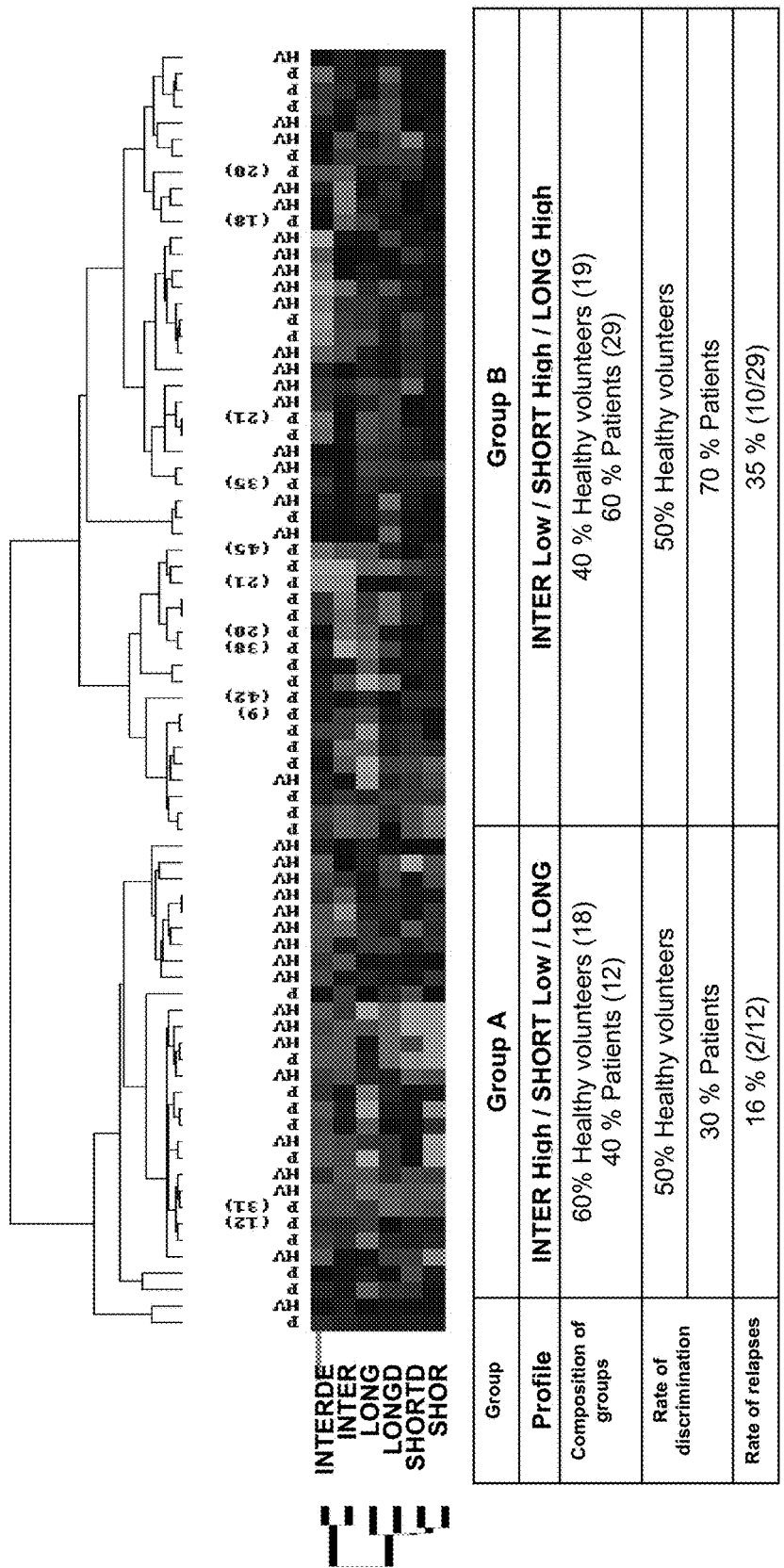

FIG. 5. Discrimination of GIST patients and healthy volunteers by clustering of the NKp30 transcriptional profiles (part A of experimental section)

Unsupervised hierarchical clustering was applied to data log-transformed and median-centred using the Cluster and TreeView programs (average linkage clustering using Pearson's correlation as similarity metric). Each row represents a NKP30 isoform and each column represents a patient (P) or a healthy volunteer (HV). The numbers in brackets represent the time to relapse in months. Red and green indicate expression levels above and below the median, respectively.

Figure 6:
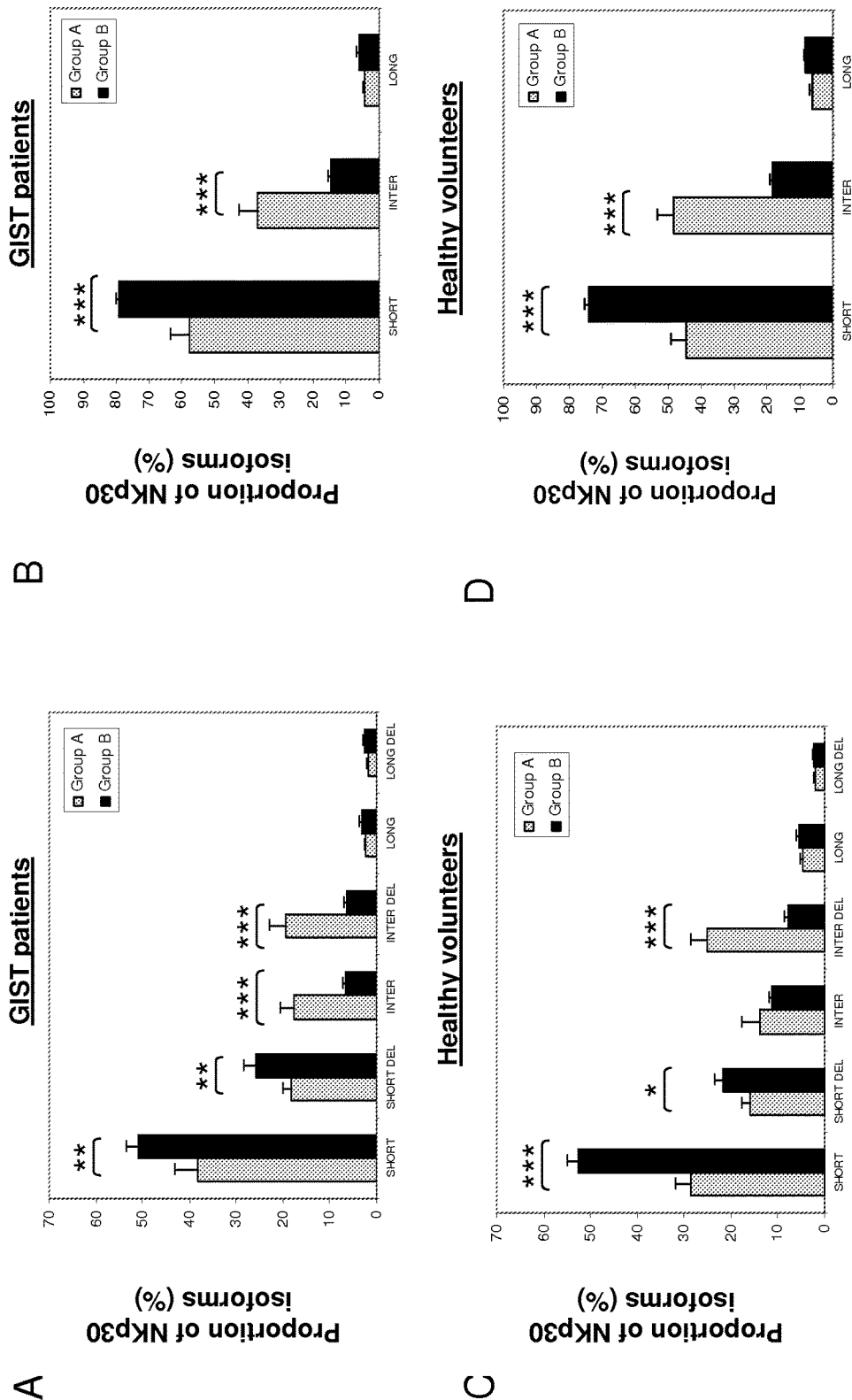

FIG. 6. Characterization of NKp30 transcriptional profiles in group A and group B obtained by clustering of 41 GIST patients and 37 healthy volunteers (part A of experimental section)

Proportions of the six isoforms were compared between group A (favorable NKp30 profile) and group B (unfavorable NKp30 profile) in GIST patients (A) and in healthy volunteers (C). NKp30 isoform proportions are shown as the ratio of the relative quantities of each isoform and the total quantity of the six isoforms. Proportions of the SHORT-, INTER- and LONG-tail isoforms were compared between group A and group B in GIST patients (B) and in healthy volunteers (D). NKp30 isoform proportions are shown as the ratio of the sum of WT—(variable Ig-like) and DEL—(constant Ig-like) extracellular domain relative quantities for each intracellular domain and the total quantity of the six isoforms. Median values±standard error were represented. The Mann-Withney test was used for statistical analyses. *:P<0.05-:P<0.01-*:P<0.001

Figure 7:
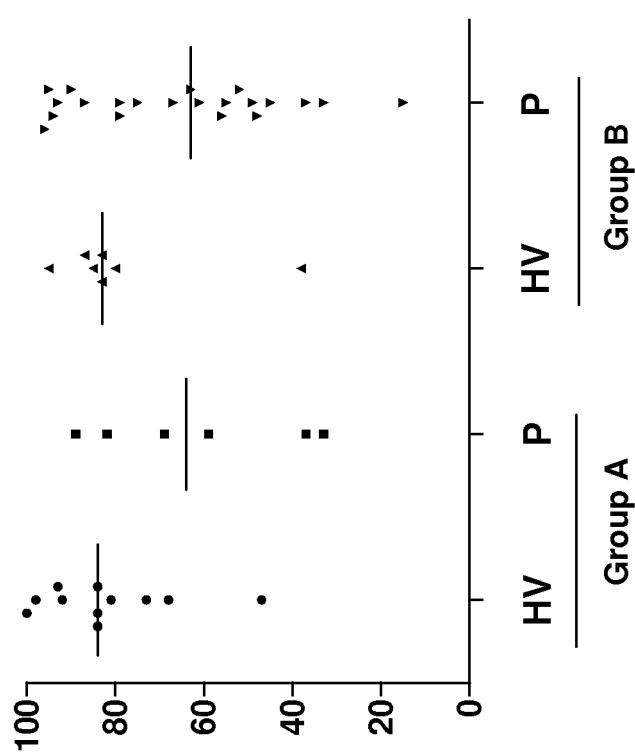

FIG. 7. Comparison of NKp30 surface expression in 37 healthy volunteers (HV) and GIST patients (P) between $INTER^{High}/SHORT^{Low}/LONG^{Low}$ group A and $INTER^{Low}/SHORT^{High}/LONG^{High}$ group B (part A of experimental section)

NK cells were immunostained with CD3-APC (clone UCHT), NKp30-PE (clone AF29-4D12), CD56-PC5 (clone N901). Cell surface analysis was performed through flow cytometry with the use of a FACScalibur cytometer and CellQuest software (Becton Dickinson).

Figure 8:
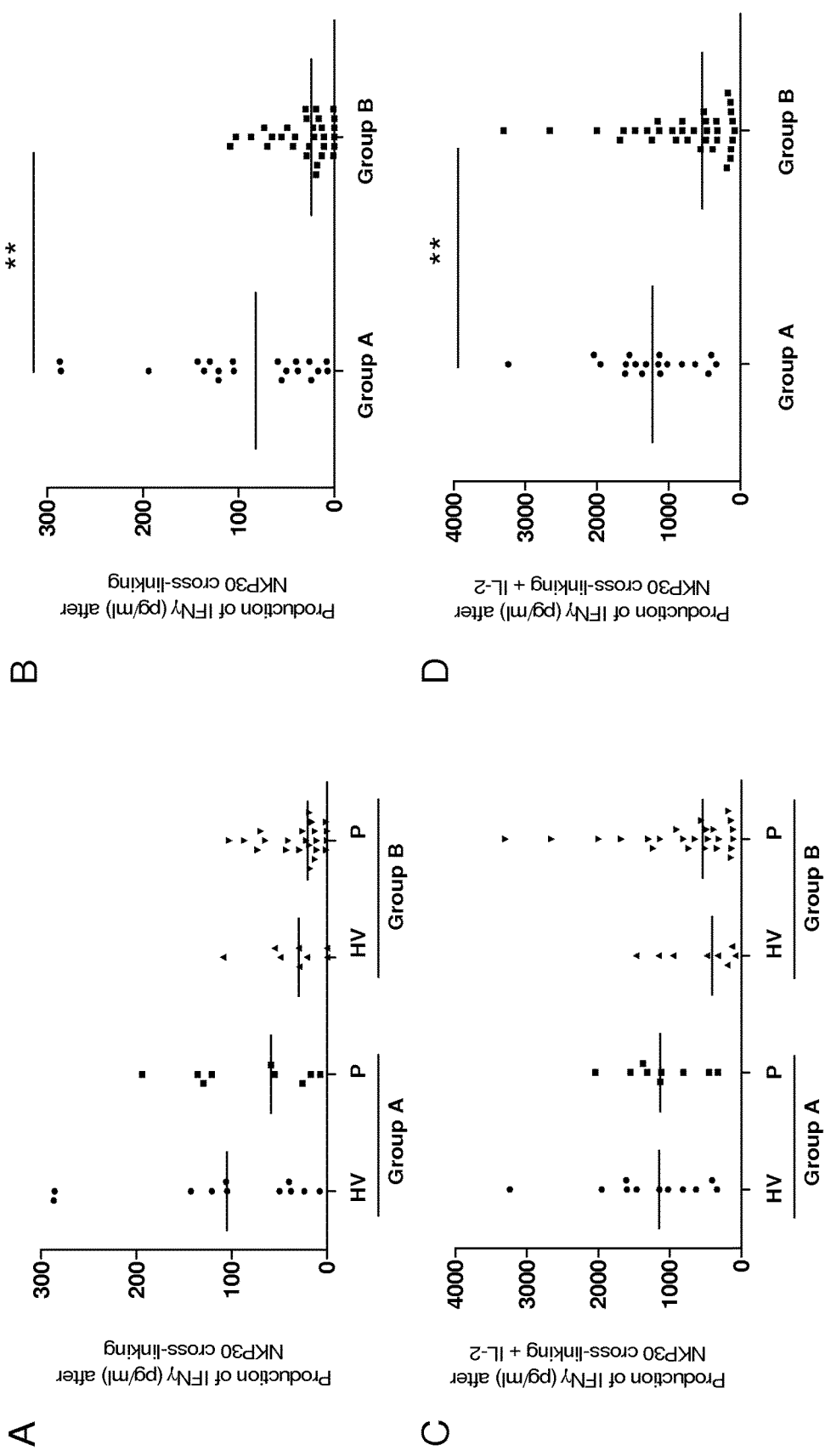

FIG. 8. Production of IFNγ from NK cells (after NKp30 crosslinking±IL-2) in the $INTER^{High}/SHORT^{Low}/LONG^{Low}$ group A and $INTER^{Low}/SHORT^{High}/LONG^{High}$ group B (part A of experimental section)

(A) Production of IFNγ was assessed by ELISA in supernatants from stimulated NK cells of healthy volunteers (HV) and GIST patients (P) in groups A and B. NK cells was stimulated for 20 hr by cross-linking of NKp30 (2.5 μg/ml of mouse IgG2a anti-NKp30). No significant differences were detected between HV and P within each group.

(B) Representation of the production of IFNγ after NKP30 cross-linking in groups A and B considering HV and P together.

(C) Production of IFNγ was assessed by ELISA in supernatants from stimulated NK cells of HV and P by cross-linking of NKp30 and IL-2 (1000 Ul/ml) for 20 hr. No significant differences were detected between HV and P within each group.

(D) Representation of the production of IFNγ after NKP30 cross-linking+IL-2 in groups A and B considering HV and P together. Bars represent medians. The Mann-Withney test was used for statistical analyses. **:P<0.01

Figure 9:
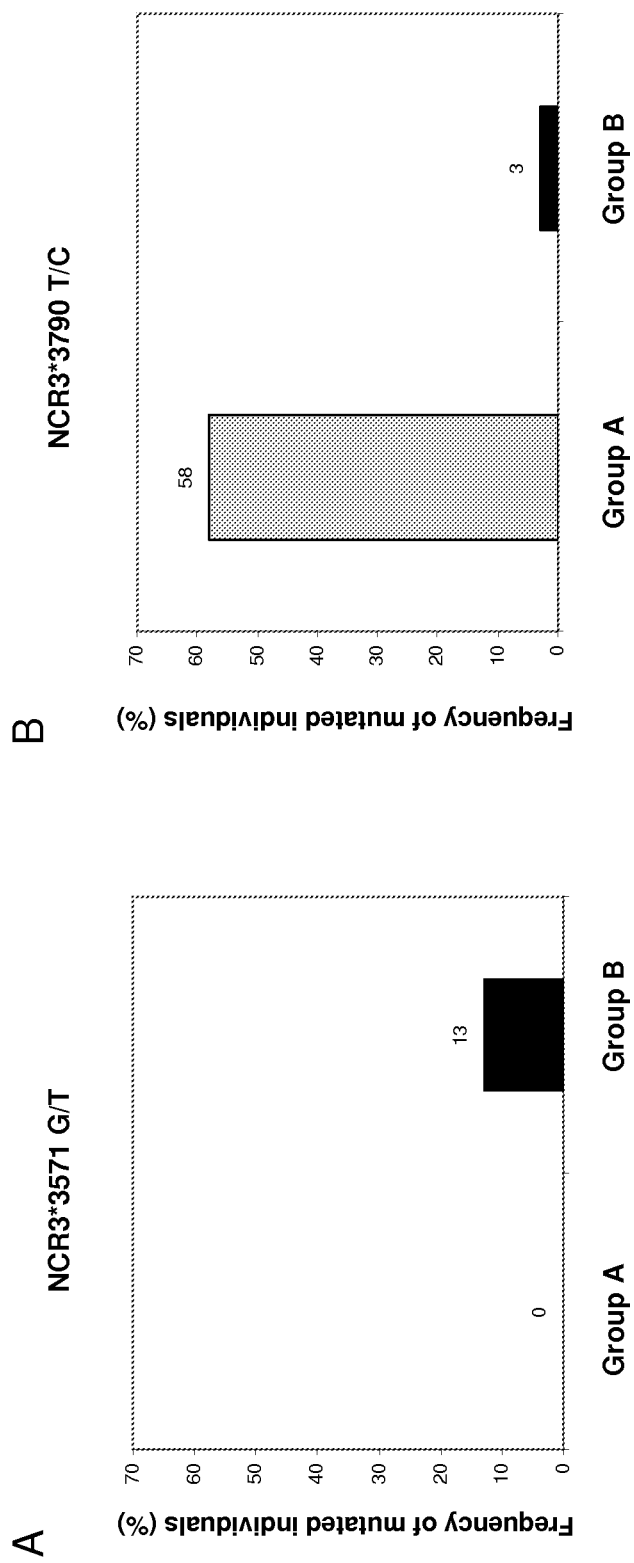

FIG. 9. Frequencies of the NCR3*3571 and NCR3*3790 candidate mutations in the $INTER^{High}/SHORT^{Low}/LONG^{Low}$ group A and $INTER^{Low}/SHORT^{High}/LONG^{High}$ group B (part A of experimental section)

(A) The NKp30 transcriptional profile of group B is associated with the non-synonymous NCR3*3571 G/T (R174S-rs3179003) mutation (13% in B versus 0% in A).

(B) The NKp30 transcriptional profile of group A is associated with the NCR3*3790 T/C (rs986475) mutation localised in the 3' untranslated region of NCR3 gene (58% in A versus 3% in B).

Figure 10:
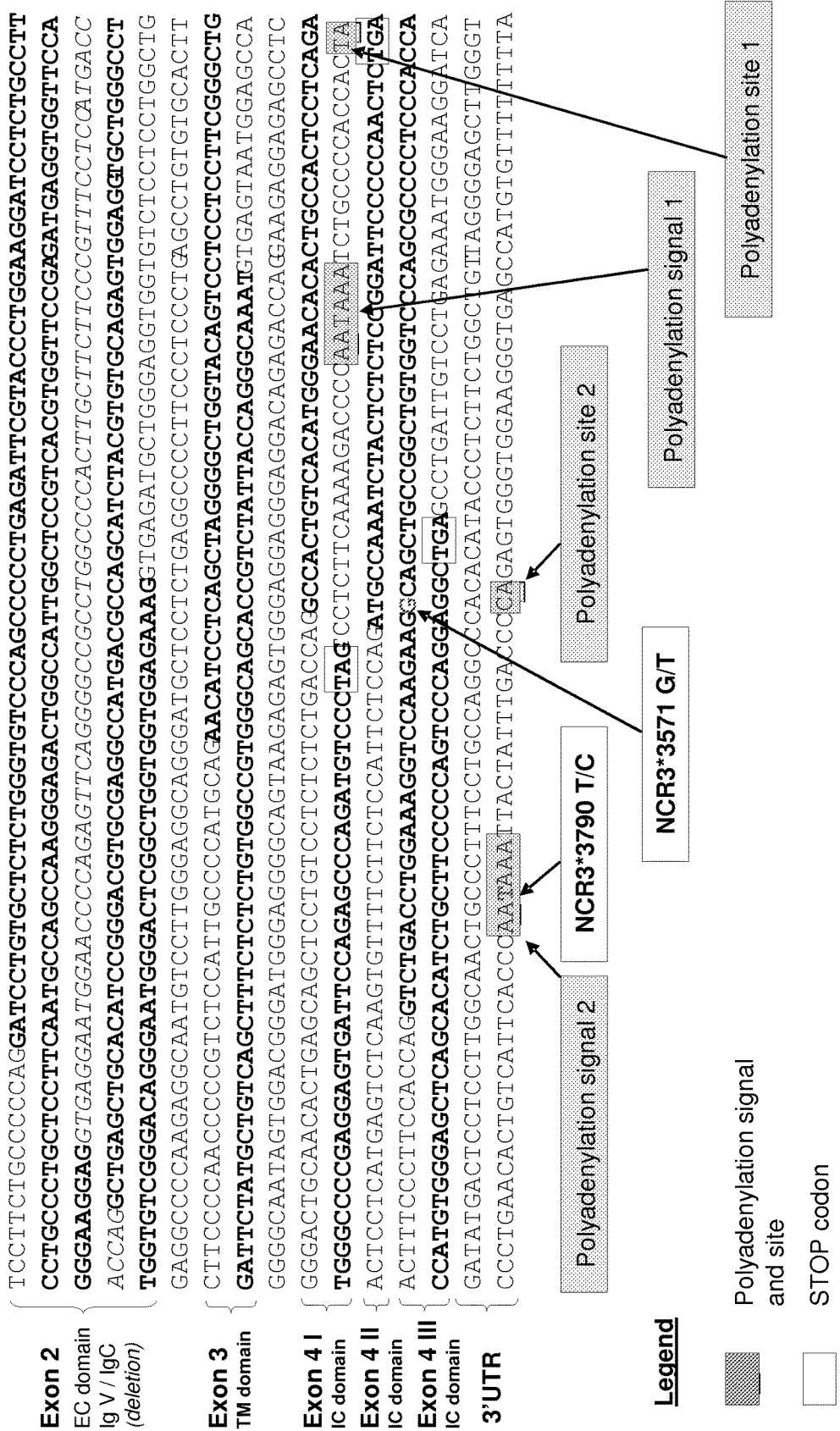

FIG. 10. Localization of the NCR3*3571 and NCR3*3790 candidate mutations in the NCR3 nucleotide sequence (SEQ ID NO: 1).

The exonic sequences are in bold. The STOP codons and polyadenylation sites are framed. The transcription of the INTER isoforms depends to the first polyadenylation site. The transcription of the SHORT and LONG isoforms depends to the second polyadenylation site. The non-synonymous NCR3*3571 mutation is localized in the intracellular domain of the LONG isoform (exon 4 III). The NCR3*3790 mutation is localized in the second polyadenylation site. The NCR3*3790 C allele disrupts the polydenylation site and blocks the transcription of the SHORT and LONG isoforms.

EC domain: extracellular domain; TM domain: transmembrane domain; IC domain: intracellular domain; 3'UTR: 3' untranslated region.

Figure 11:
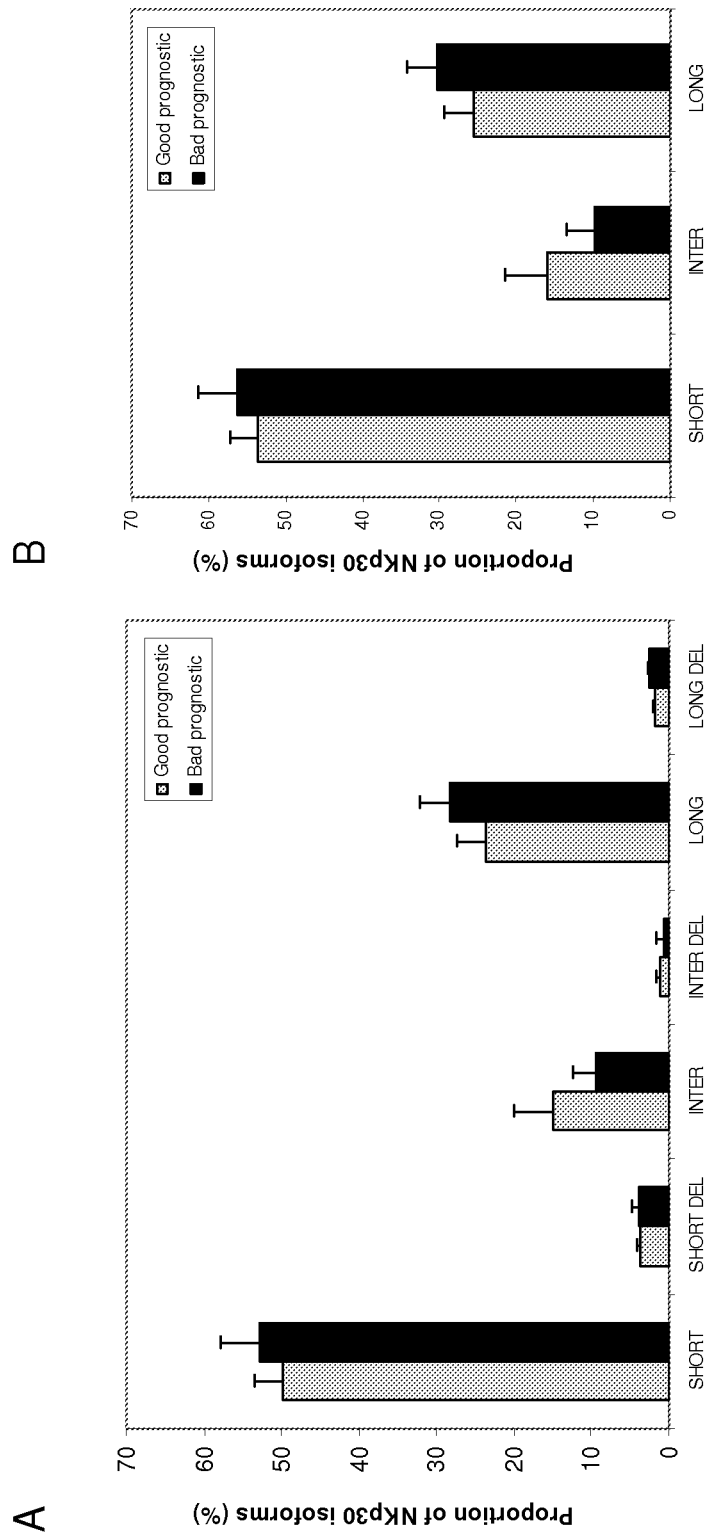

FIG. 11. Comparison of proportions of NKP30 isoforms in neuroblastoma patients with a good or bad clinical prognostic (part A of experimental section)

(A) Proportions of the six isoforms were compared between 7 neuroblastoma patients with a good clinical prognostic and 12 neuroblastoma patients with a bad clinical prognostic.

NKp30 isoform proportions are shown as the ratio of the relative quantities of each isoform and the total quantity of the six isoforms.

(B) Proportions of the SHORT-, INTER- and LONG-tail isoforms were compared between 7 neuroblastoma patients with a good clinical prognostic and 12 neuroblastoma patients with a bad clinical prognostic. NKp30 isoform proportions are shown as the ratio of the sum of WT—(variable Ig-like) and DEL—(constant Ig-like) extracellular domain relative quantities for each intracellular domain and the total quantity of the six isoforms.

Median values±standard error were represented.

Figure 12:
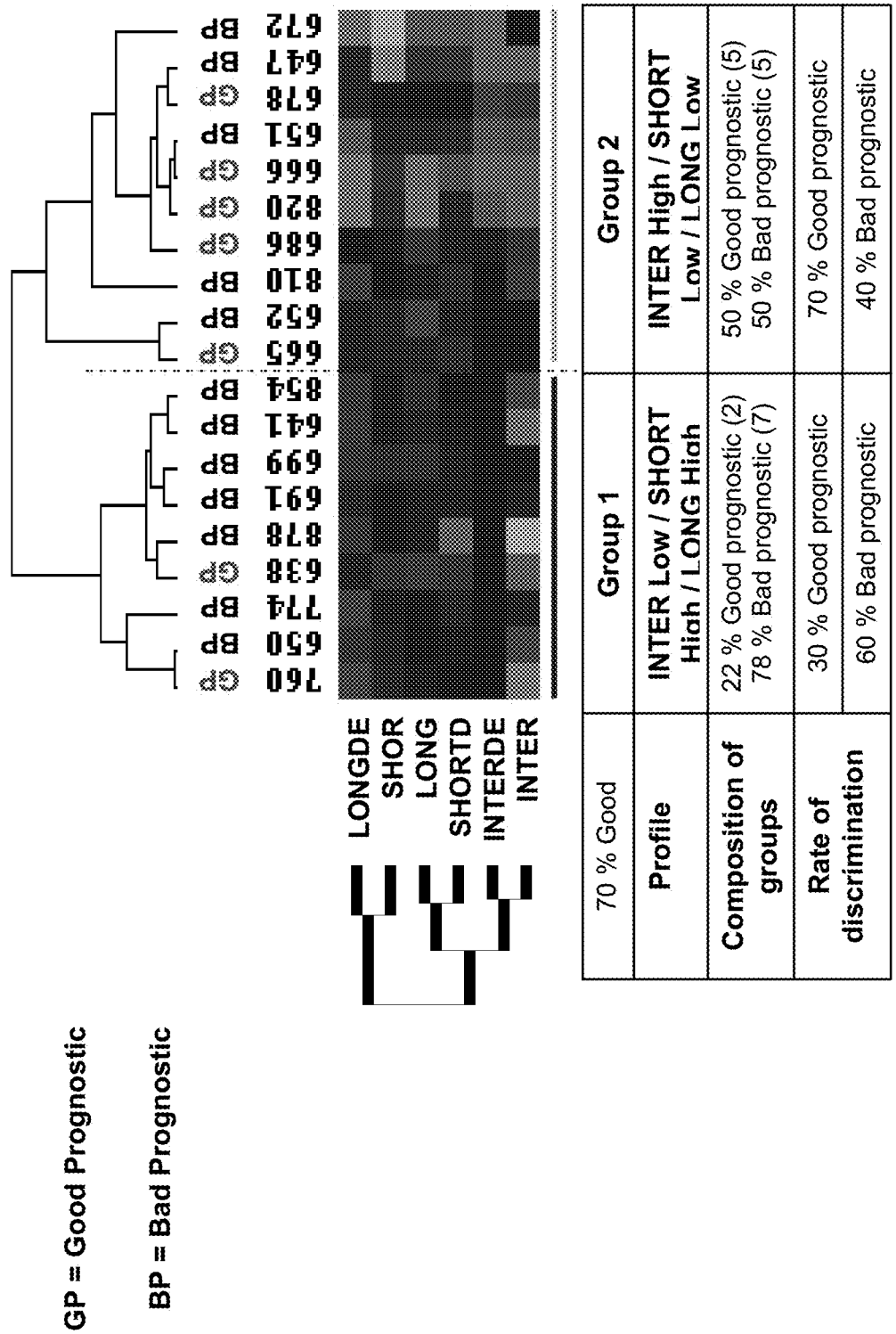

FIG. 12. Discrimination of neuroblastoma patients with good and bad clinical prognostic by clustering of the NKp30 transcriptional profiles (part A of experimental section)

Unsupervised hierarchical clustering was applied to data log-transformed and median-centred using the Cluster and TreeView programs (average linkage clustering using Pearson's correlation as similarity metric). Each row represents a NKP30 isoform and each column represents a neuroblastoma patient with a good clinical prognostic (GP) or a bad clinical prognostic (BP). Red and green indicate expression levels above and below the median, respectively.

Figure 13:
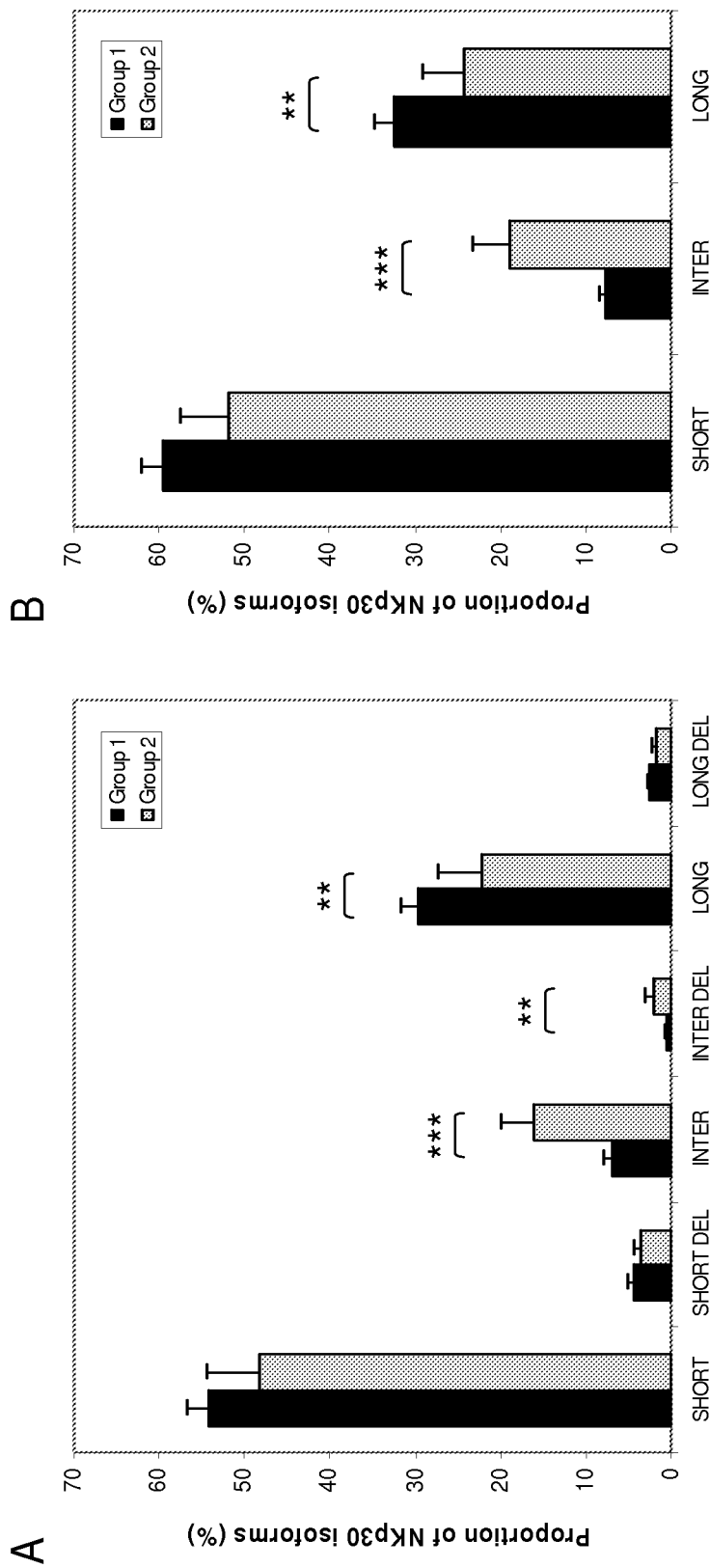

FIG. 13. Characterization of NKp30 transcriptional profiles in group 1 and group 2 obtained by clustering of the 19 neuroblastoma patients (part A of experimental section)

(A) Proportions of the six isoforms were compared between group 1 (unfavorable NKp30 profile) and group 2 (favorable NKp30 profile) in neuroblastoma patients.

NKp30 isoform proportions are shown as the ratio of the relative quantities of each isoform and the total quantity of the six isoforms.

(B) Proportions of the SHORT-, INTER- and LONG-tail isoforms were compared between group 1 and group 2 in neuroblastoma patients.

NKp30 isoform proportions are shown as the ratio of the sum of WT—(variable Ig-like) and DEL—(constant Ig-like) extracellular domain relative quantities for each intracellular domain and the total quantity of the six isoforms.

Median values±standard error were represented. The Mann-Withney test was used for statistical analyses. *:P<0.05-:P<0.01-*:P<0.001

Figure 14:
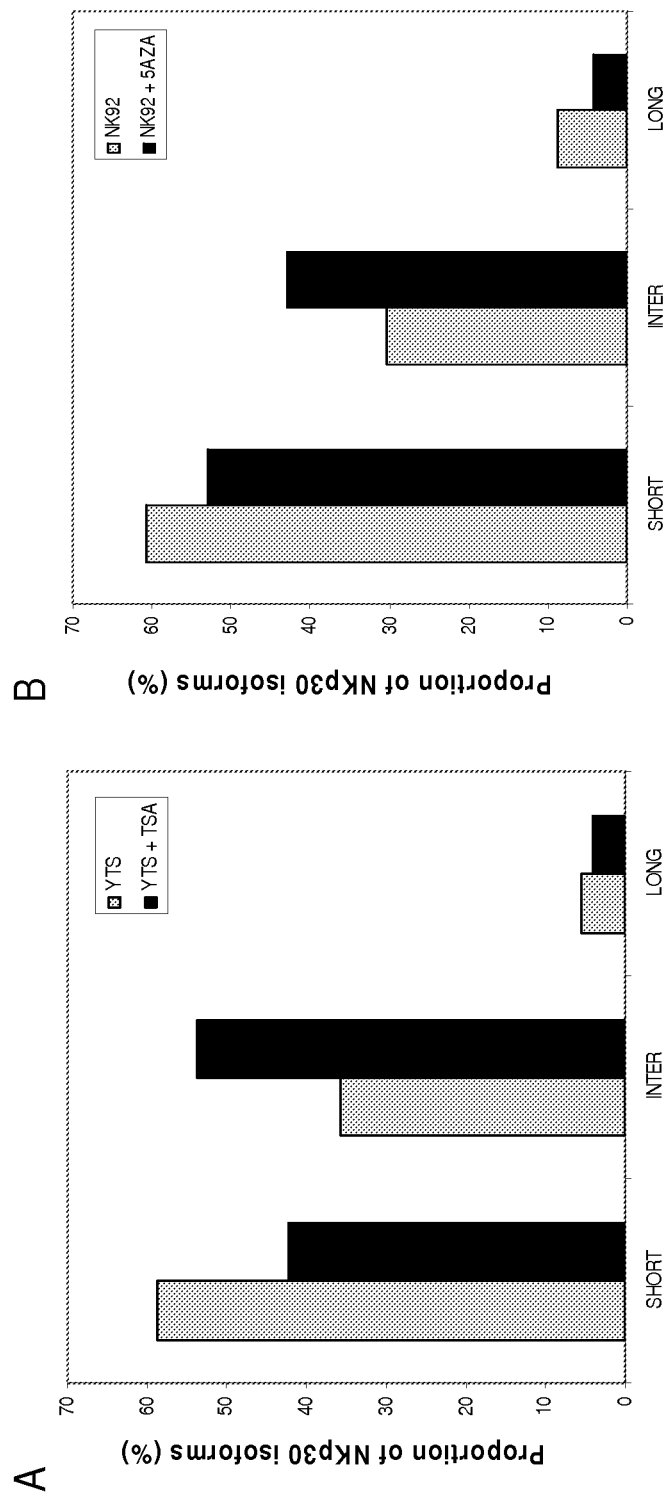

FIG. 14. Modulation of alternative splicing of NCR3 gene with histone deacetylase inhibitors and DNA methyltransferase inhibitors (part A of experimental section)

NKp30 isoform proportions are shown as the ratio of the sum of WT—(variable Ig-like) and DEL—(constant Ig-like) extracellular domain relative quantities of each isoform (SHORT-, INTER- and LONG-tail isoforms) and the total quantity of the six isoforms.

(A) YTS cells were seeded ($5.10^5$ NK/well) in 96 wells plates and incubated with trichostatine A (100 nM) (TSA) for 45 h at 37° C.

(B) NK92 cells were seeded ($5.10^5$ NK/well) in 96 wells plates and incubated with 5-azacitidine (2 μM) (5AZA) and IL-2 (50 Ul/ml) for 36 h at 37° C.

Figure 15:
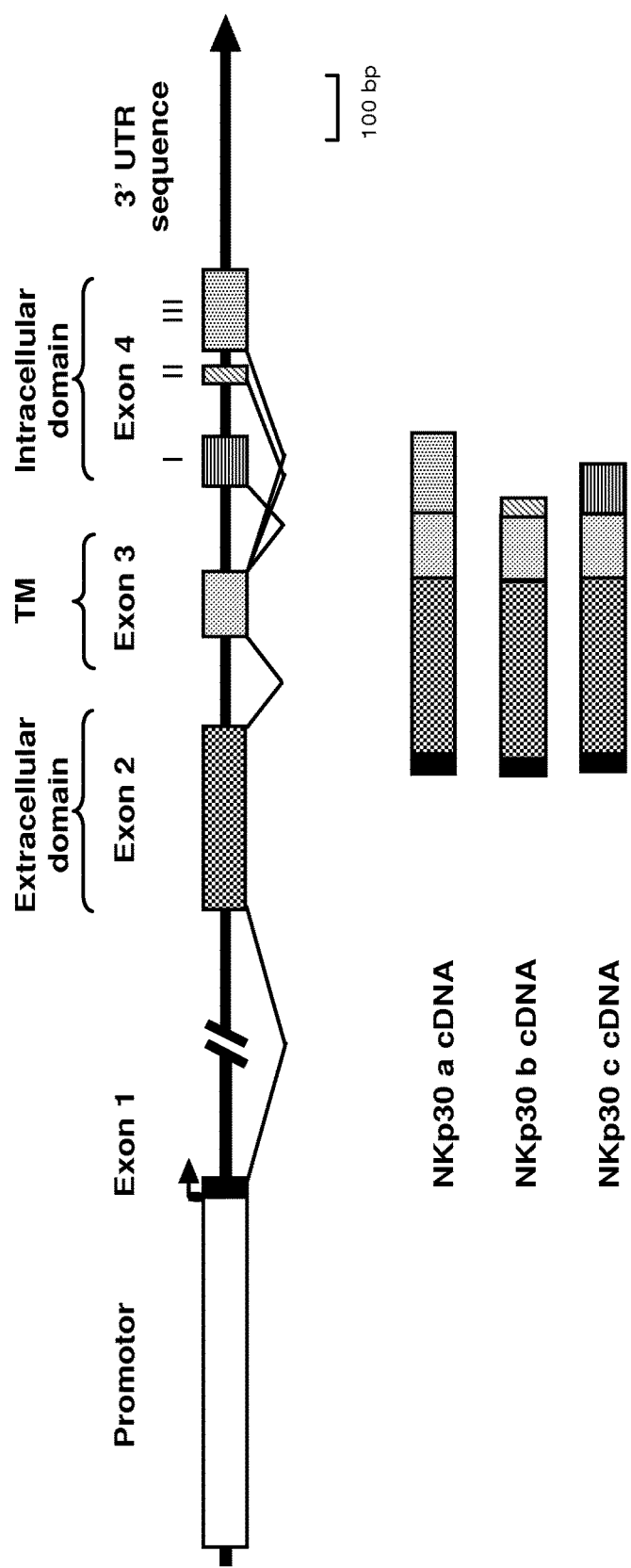

FIG. 15. Scheme of expression cloning of the NKp30 exon 4I, exon 4II and exon 4III in vectors.

The three cDNA NKp30a (LONG) (exon 4III), NKp30b (SHORT) (exon 4II) and NKp30c (INTERMEDIATE) (exon 4I) derived from NCR3 gene of NK92 cell line were cloned in pIRES bicistronic expression vector.

Figure 16:
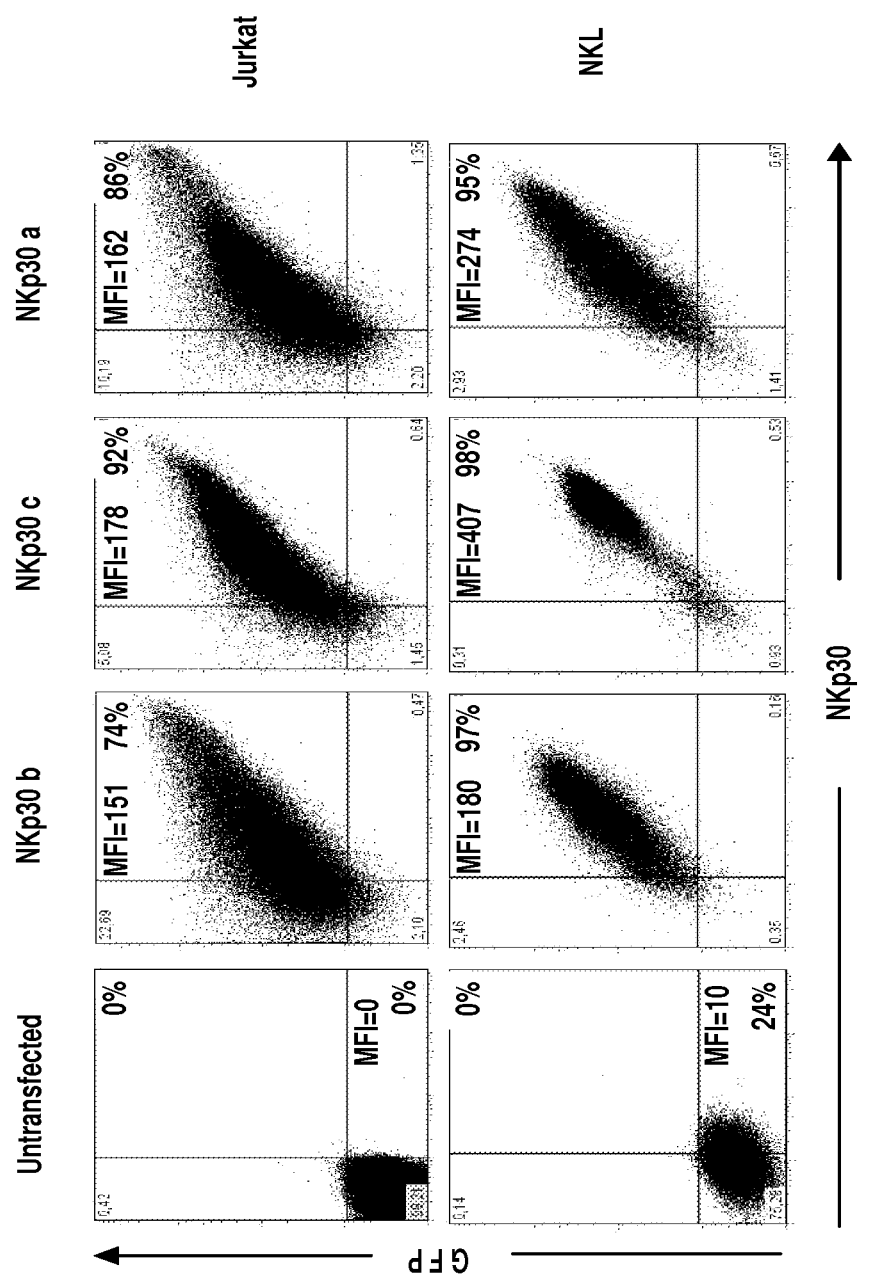

FIG. 16. Expression of NKp30a, b or c isoforms in cell lines.

Jurkat (A) and NKL cell lines (B) were transfected with plasmid cDNAs encoding the various isoforms of NKp30a, b or c along with GFP. After 3 weeks selection in G418, cell lines were examined for GFP and NKp30 expression by flow cytometry. A representative dot plot is depicted for Jurkat (A) and NKL (B).

Figure 17:
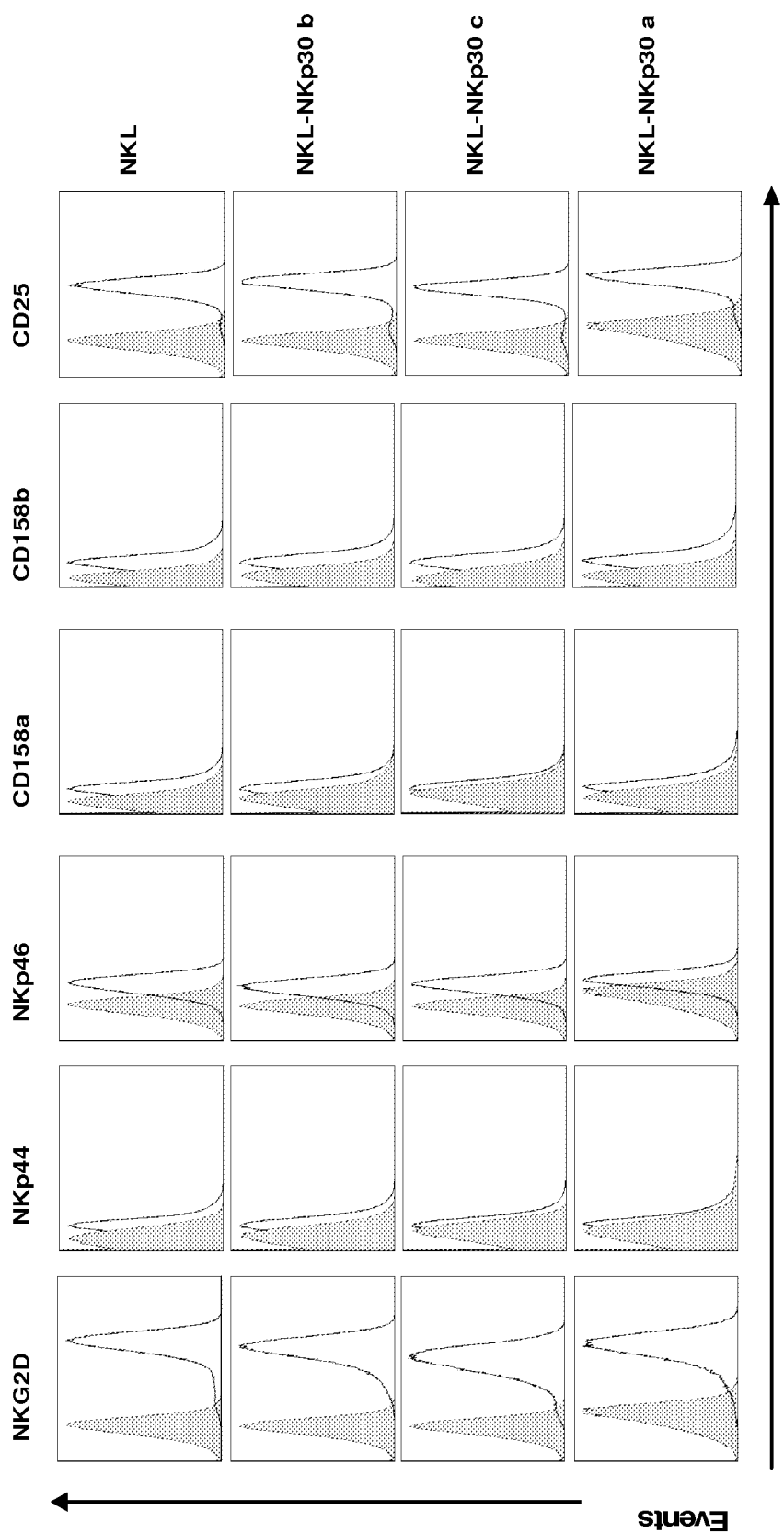

FIG. 17. Phenotyping of the transfected NKL cell lines before and after G418 selection.

Flow cytometry analyses of different NK cell receptors on the NKL cell lines stably transfected with the cDNA encoding the distinct NKp30 isoforms. No significant difference was observed.

Figure 18:
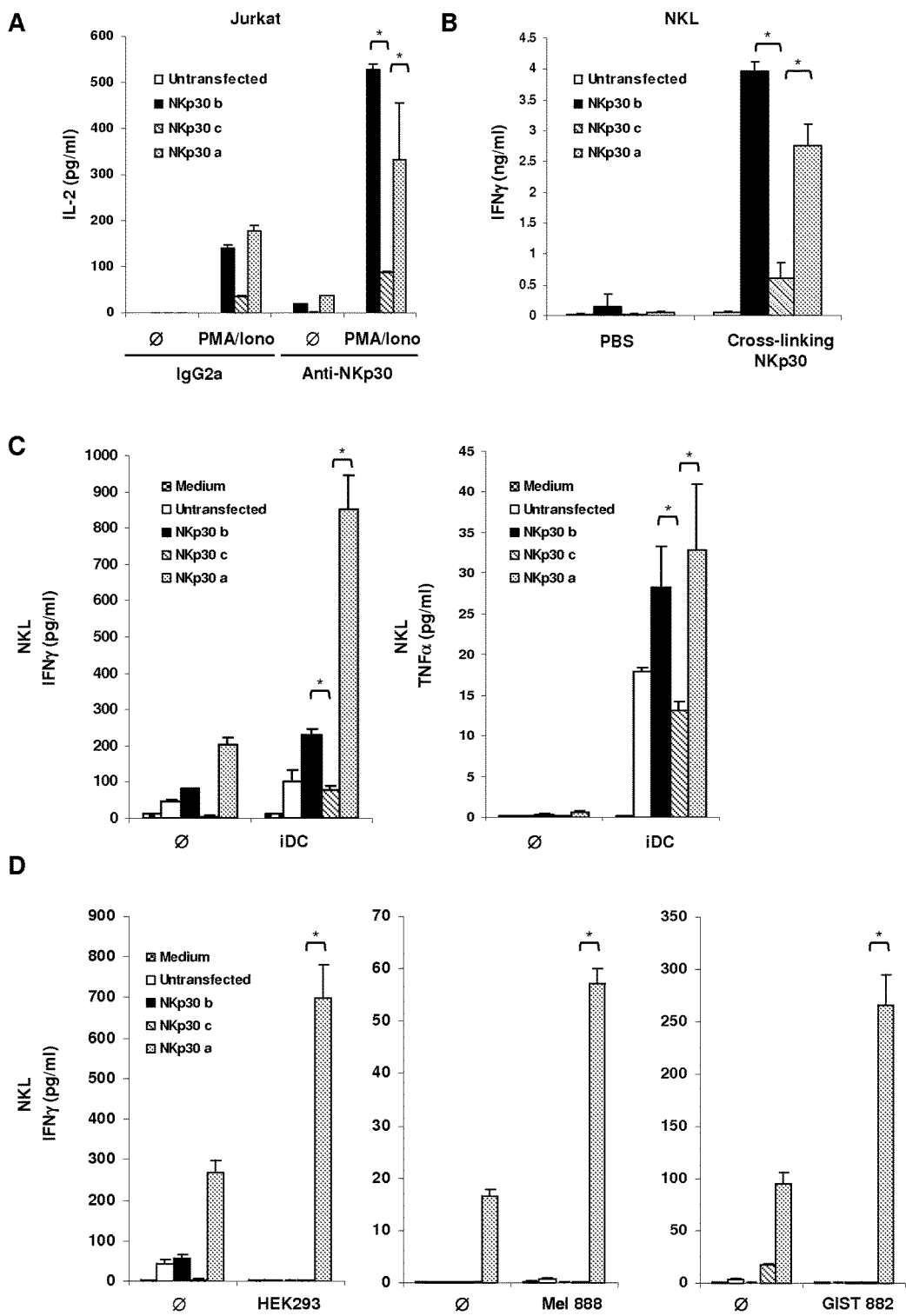

FIG. 18. The NKp30c isoform fails to mediate cytokine secretion upon NKp30 triggering.

Immobilized mouse IgG2a anti-NKp30 Ab (clone 210847, 2.5 ug/ml) or control IgG with (A) or without (B) PMA-ionomycine (5 ng/mL, 0.1 μg/mL) were used to cross-linked all three transfected Jurkat (A) or NKL (B). In addition the transfected NKL were stimulated with immature DC (ratio DC:NKL 1:3) (C), or with various tumour cell lines (ratio 1:1) (D) for 24 hrs. The graph depicts a representative experiment out of three, monitoring the IL-2 (A) or IFNγ (B, C, D) or TNFα (C) secretion levels in the supernatants. The experiments have been performed three times (A, B, D) and five times using three different DC donors (C) yielding identical results. *p<0.05.

Figure 19:
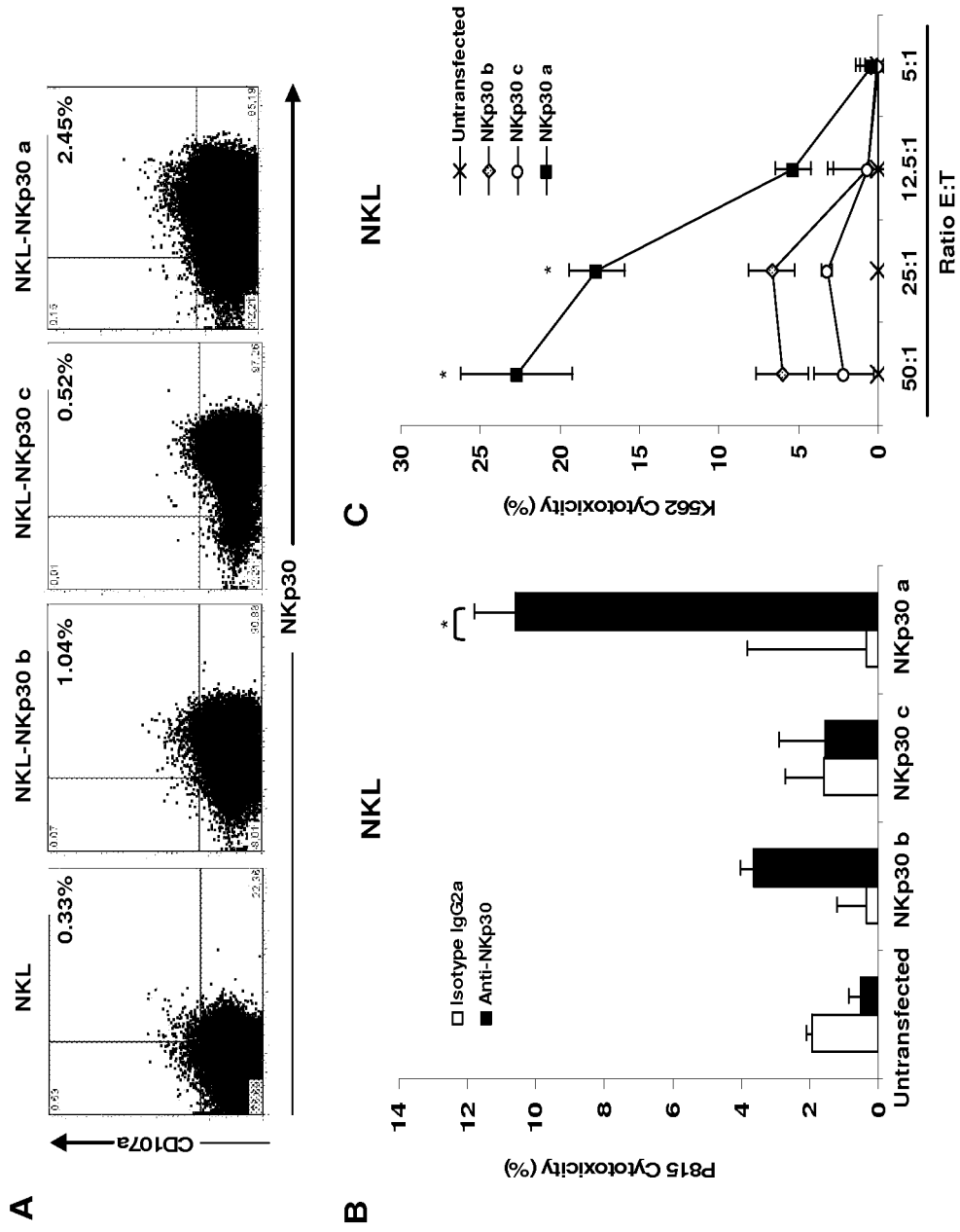

FIG. 19. The NKp30a (LONG) isoform selectively induces degranulation of NKL.

CD107a expression on all three NKL transfectants after 7 h NKp30 cross-linking is shown (A). The three NKp30-transfected NKL cytotoxicity against P815 coated with anti-NKp30 mAb (B) or K562 (C) were performed in a standard 4 hour chromium release assay. Experiments were conducted in triplicates at various effector to target (E:T) ratios (50:1, 25:1, 12.5:1, 5:1) (C) and at 50:1 (B). A representative experiment out of three is depicted. *p<0.05.

Figure 20:
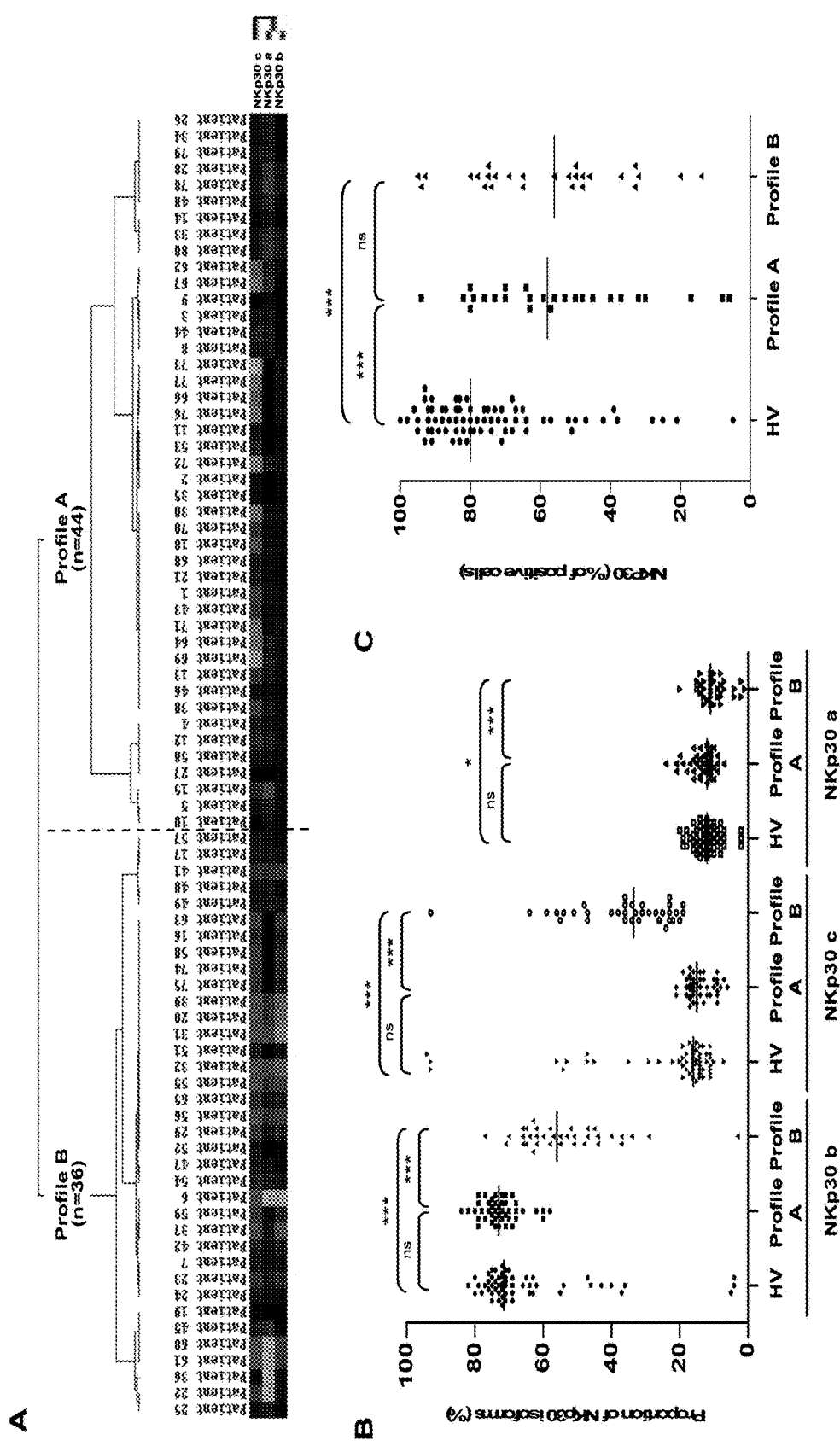

FIG. 20. Expression of NKp30 isoforms in a cohort of 80 GIST patients.

(A) Clustering of NKp30 profiles based on the three distinct isoforms in a cohort of GIST.

NKp30 profiles based on proportions of the three NKp30 isoforms were performed by RT-PCR (normalized on β2 microglobulin) and an unsupervised hierarchical clustering of NKp30 profiles was applied to data log-transformed and median-centered using the Cluster and TreeView programs (average linkage clustering using Pearson's centered correlation as similarity metric). Each row represents a NKP30 isoform and each column represents a patient. Red and green indicate expression levels above and below the median, respectively.

(B) Differential proportions of each isoform of NKp30 between GIST and HV.

Data presented in (A), for 80 GIST are depicted in a graph as proportions of the distinct isoforms in the two groups (profile A versus profile B GIST) and compared to results obtained with a cohort of n=56 HV.

(C) Profile A and B do not differ in NKp30 expression detected in flow cytometry. Fresh NK cells were examined at the time of the transcriptional analysis of the NKp30 isoforms during IM therapy. No significant difference between the two groups could be found. *p<0.05. ns: non-significant.

Figure 21:
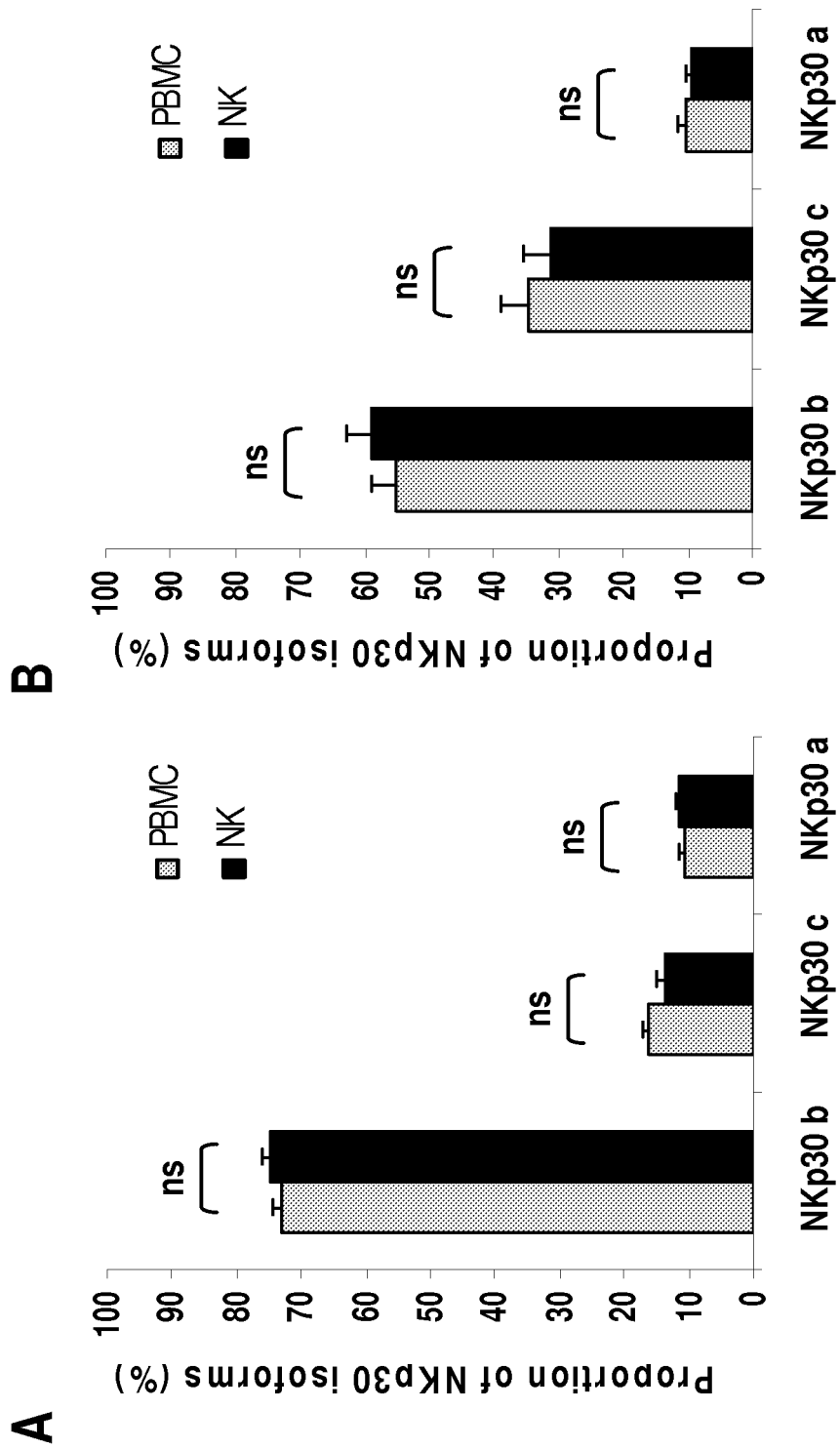

FIG. 21. Comparisons of the transcriptional profiling of NKp30 obtained in bulk PBMC and purified NK cells.

The determination in RT-PCR of the relative expression of each individual splice variant of NKp30 was performed on 11 GIST with a profile A (A) and 9 GIST with a profile B (B) according to the procedure described in FIGS. 20A and 20B starting from cDNA extracted from PBMC or purified NK cells after Ficoll. No significant (ns) difference was observed between NKp30 profiles from PBMC and NK.

Figure 22:
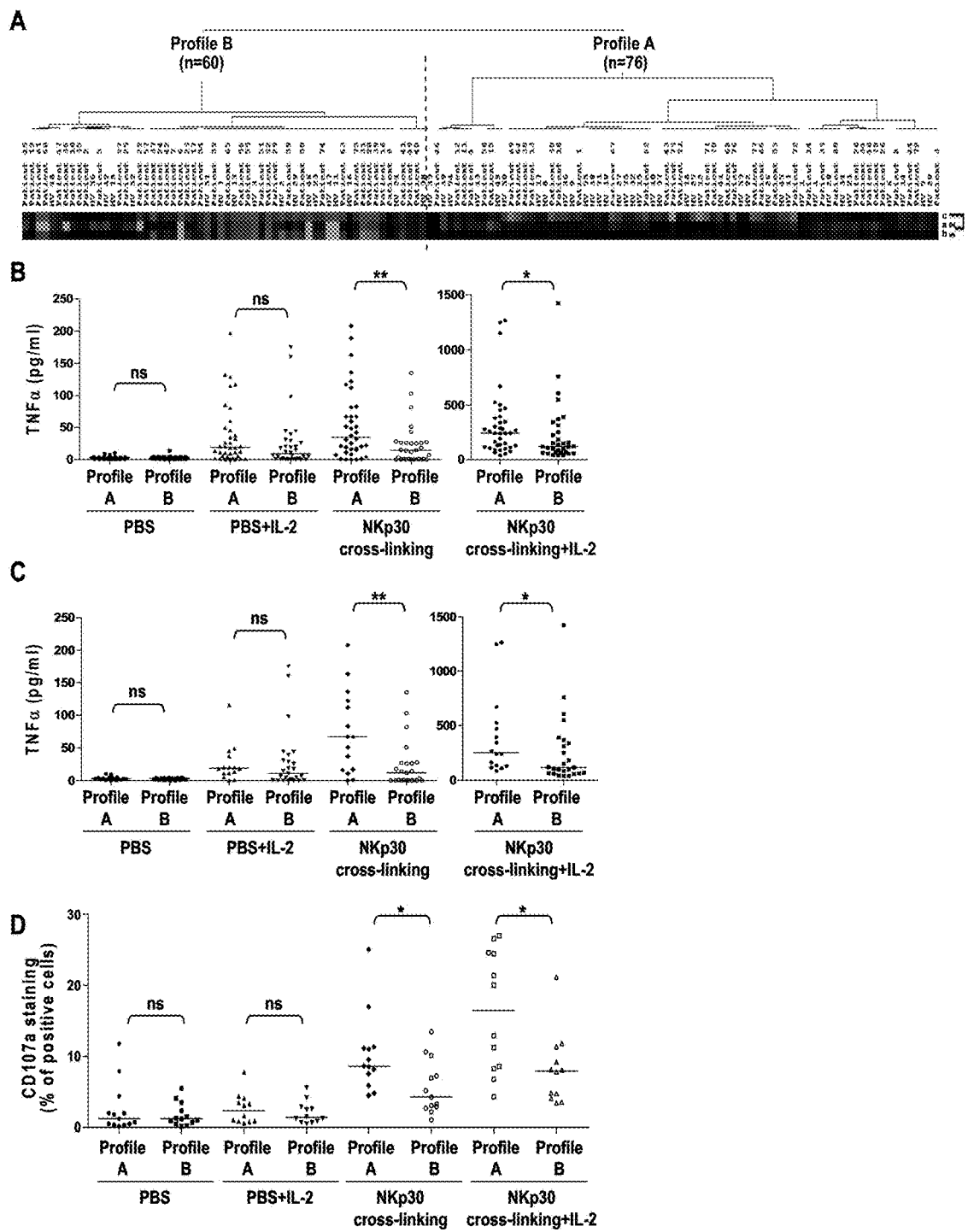

FIG. 22. Profile B individuals exhibit NKp30-dependent functional defects compared with profile A homologues.

(A) Clustering of NKp30 profiles based on the three distinct isoforms among GIST and matched HV.

Identical setting as in FIG. 20a but NKp30 profiles from HV-derived NK cells were examined in 56 sex, age and geography-matched HV.

(B-C) Profile B is associated with defective NKp30-dependent TNFα production in the whole cohort of individuals.

Cross-linking of NKp30 on circulating NK cells from n=56 HV and n=80 GIST resulted in cytokine production that was measured in ELISA at 24 hrs. TNFα release was compared between individuals (GIST+HV in (B), GIST in (C)) classified in profile A or B according to the unsupervised hierarchical clustering (FIG. 20A).

(D) Profile B exhibits defects in NKp30-dependent NK cell degranulation.

Id. as in (B-C) but CD107a expression was analyzed in the presence of immobilized anti-NKp30 and 1000 IU/ml of rhIL-2.

All experiments were performed in triplicates and twice for most of the individuals at two different time points.

*p<0.05. ns: non-significant.

Figure 23:
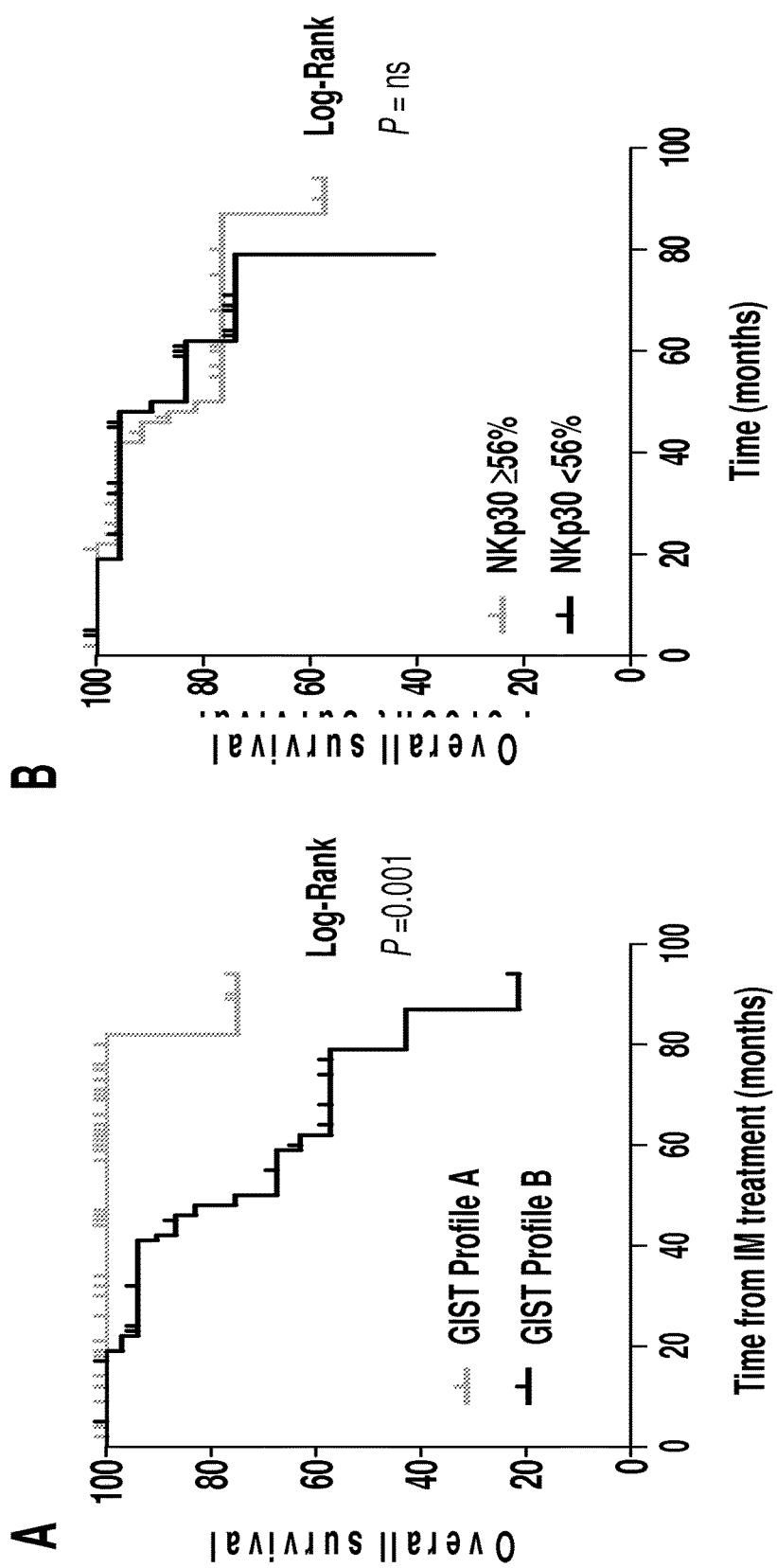

FIG. 23. NKp30 isoforms dictate the survival of GIST patients.

(A) Overall survival from initial imatinib mesylate (IM) treatment in profile A (n=44) versus B (n=36) GIST patients.

In univariate analysis using Kaplan-Meier method, profile B patients (defined in FIG. 20) were found to have an inferior overall survival (median survival: 80 months in profile B vs median not reached in profile A, Log-Rank test: p=0.001). In the Cox regression analysis, profile B GIST possessed a relative risk of death equal to 13.1 (95% CI [4.9-36.1], p=0.01).

(B) Overall survival as a function of NKp30 membrane expression in flow cytometry.

Similar analyses as in (A) but taking into account GIST presenting with NKp30 surface expression <56% (n=26) or > and equal to 56% (n=27) on circulating NK cells at the time of determination of the transcriptional profile (FIG. 20A). The threshold of NKp30 surface expression (56%) was defined as the median of the 80 GIST patients (FIG. 20C).

Figure 24:
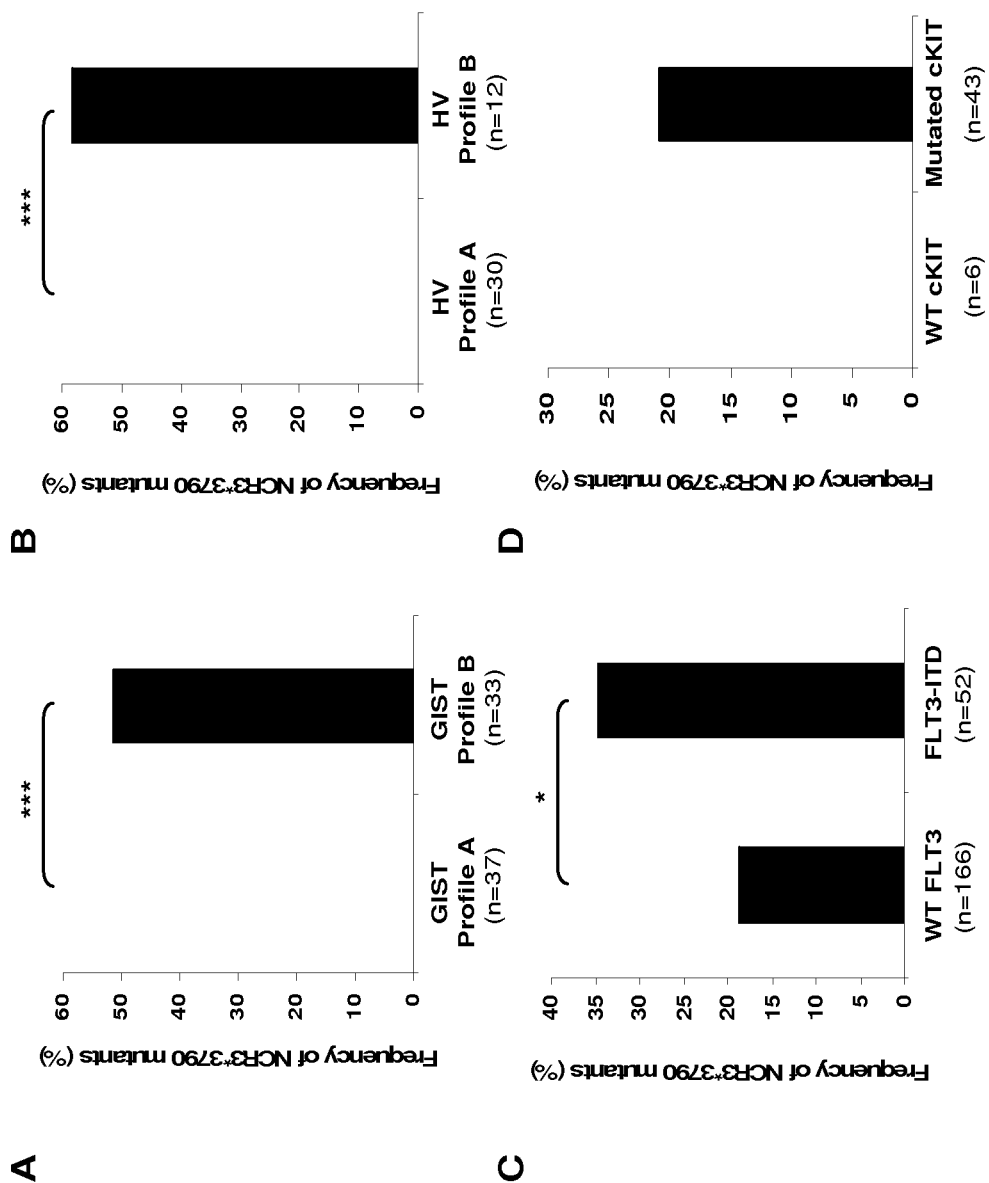

FIG. 24. The NCR3*3790 T/C SNP is associated with profile B and "monogenic" tyrosine kinase-driven malignancies.

(A) Frequency of the NCR3*3790 T/C SNP in profile A and B individuals. Genotyping of patients of the GIST cohort detailed in FIG. 20A and HV detailed in FIGS. 20B and 21A according to a procedure described in material and methods.

(B) Frequency of the NCR3*3790 T/C SNP in patients bearing an AML according to the FLT3 mutational status of the AML.

The mutational status of the tumors was determined as previously described[51]. (C) Frequency of the NCR3*3790 T/C SNP in patients bearing a GIST according to the KIT mutational status of the GIST.

The mutational status of the tumors was determined as previously described[52]. The mutational status of the tumor remained undetermined in 32.5% cases in the cohort of GIST described in FIG. 20.

DEFINITIONS

In order to facilitate review of the various embodiments, the following descriptions of terms are provided:

The term "cancer" as used herein refers to any type of malignancy (primary or metastases).

Typical cancer are X-rays, anthracycline, cis-platinum and/or oxali-platinum sensitive cancer such as breast cancer, stomach cancer, sarcoma (more particularly gastrointestinal stromal tumor or GIST), ovarian cancer, endometrium cancer, bladder cancer, cervix cancer, prostate cancer, rectum cancer, colon cancer, lung cancer, ORL cancer, paediatric tumors (neuroblastoma, glyoblastoma multiforme), lymphoma, leukaemia (acute and chronic myeloid leukemia (AML and CML), acute lymphoblastic leukemia (ALL)), myeloma, seminoma, Hodgkin and malignant hemopathies. Another typical cancer is a cancer sensitive to tyrosine kinase inhibitors (TKI) such as the Gastrointestinal stromal tumor (GIST).

The term "sensitivity to a treatment" refers to the level of response of a subject to a treatment, including but not limited to the ability to metabolize a therapeutic compound or substance, to the ability to convert a pro-drug to an active drug, to the pharmacokinetics (absorption, distribution, elimination) and to the pharmacodynamics (receptor-related) of a drug in an individual. The treatment may be a chemotherapy, including for example administration of an alkylating agent or of an anthracycline, such as doxycycline (DOX), oxali-platinum or cis-platinum; a therapy implying administration of a tyrosine kinase inhibitor (TKI) such as imatinib mesylate (ST1571) and sunitinib malate (SU11248); and/or the treatment may be radiotherapy using gamma or X-rays (XR) for example.

The term "prognosis of a cancer", as used herein, refers to the method consisting of assessing the course of a disease, in other words, the presumed fatal or positive health outcome of a disease.

Typically, a subject having an increased risk of developing a cancer has a NKp30 isoforms abnormal status or profile wherein the relative amount of the NKp30 intermediate isoform is relatively higher than a reference or mean value or than the (relative) amount(s) of the NKp30 short and/or long isoforms.

The sample to be tested contains nucleic acids and/or polypeptides. Examples of such samples include fluids, tissues, cell samples, organs, biopsies, etc.

The nature of the collected sample is not necessarily correlated to a particular type of cancer. The collected tissue may indeed be a cancerous tissue (preferably frozen rather than paraffin embedded) or a healthy tissue (for example blood, skin, stroma).

The tissue may be collected from a selected cancerous tissue.

The sample may also be obtained for example from a tissue selected from blood, plasma and bone marrow, independently of the optional abnormal or diseased status of said tissue.

Preferably, the sample comprises cells known to express NKp30 such as umbilical cord T lymphocytes and endometrial epithelial cells, preferably peripheral blood mononuclear cells (PBMC), in particular NK cells.

In a particular example, if the assay is performed on a subject afflicted with a cancer selected from a paediatric tumor, such as neuroblastoma and a GIST, a sample of blood (in particular a sample comprising a population of PBMC), stroma, skin or tumor tissue may be provided.

The invention may be used in various subjects, for example animals, particularly mammals, preferably humans, including adults, children and at the prenatal stage.

The term "subject" generally refers to a patient afflicted with a cancer, or to a subject who may develop a cancer.

The subject can also be a subject who is a potential bone marrow donor. Invention may be used to determine whether the donor subject has a normal NKp30 expression, in particular a normal NKp30 RNA transcript isoforms status or profile, or a normal expression or activity of at least one NKp30 protein isoform.

The subject can further be a candidate for an allogeneic bone marrow transplantation.

The term "abnormal" is herein associated with a deviation from normal characteristics. Normal characteristics can be found in a control, a standard for population, etc. For instance, where the abnormal condition is a disease condition such as a cancer, a few appropriate sources of normal characteristics might include an individual who is not suffering from the cancer, a standard population of individuals believed not to be suffering from the cancer, etc.

A population of individuals afflicted with a cancer but believed to have a favourable prognosis based on favorable clinical criteria known by the man of the art (such as the age of the individual, the stage of the cancer and/or or the histopathology of the cancer) may, in particular embodiments, be considered as a control or reference population.

The term "abnormal" usually refers to a condition that is associated with a disease. For instance, a certain abnormality (such as an abnormality in a NCR3 nucleic acid or in the expression or activity of at least one NKp30 protein isoform) can be described as being associated with an unfavourable prognosis of the cancer in a subject or with a resistance to a treatment of cancer.

Typically, the term "abnormal" may be used in reference to a NKp30 isoforms status or profile wherein the amount of the NKp30 intermediate isoform is higher than a reference or mean value or than the relative amount(s) of NKp30 short and/or long isoforms. An abnormal (relative) amount of the NKp30 intermediate isoform is for example an amount exceeding about 15%, preferably 20%, even more preferably 19%, of the total isoforms amount which include long, short and intermediate isoforms with variable extra-cellular domains. The corresponding percentages of long isoforms being inferior to about 20%, preferably about 15%, and the corresponding percentages of short isoforms being inferior to about 80%, preferably 77%, even more preferably 70% for short isoforms.

An abnormal nucleic acid, such as an abnormal NCR3 nucleic acid, is one that is different in some manner from a normal (wild type) nucleic acid. Such abnormality includes but is not necessarily limited to a mutation in the nucleic acid [such as a point mutation (e. g., a single nucleotide polymorphism, also named SNP) or short deletion, insertion or duplication of a few to several nucleotides], compared to a control or standard. It will be understood that these types of abnormalities can co-exist in the same nucleic acid or in the same cell or sample. In addition, it is understood that an abnormality in a nucleic acid may cause an abnormality in expression of the corresponding protein(s).

NKp30 protein herein relates to a protein encoded by the NCR3 gene.

As explained previously, the NCR3 gene presents six different alternative splice forms encoding six different proteins respectively named NKp30A, NKp30B, NKp30C, NKp30D, NKp30E, and NKp30F (FIG. 2)[24]. Three of the isoforms encode a potential variable Ig-like or Ig-like domain and the other three a potential constant Ig-type or Ig-like domain (partially deleted variable Ig-type domain). These two different extracellular domains can be linked to three different intracellular domains of 36 amino acids ("long tail" domain), 25 amino acids ("intermediate tail" domain), and 12 amino acids ("short tail" domain), depending on which exon 4 (FIG. 1) is expressed[24].

An abnormal NKp30 protein isoform is thus a protein isoform the sequence, configuration, maturation or expression of which is different from the normal wild-type protein isoform. Preferably the abnormal protein isoform is not functional or only partly functional.

The term preferably includes the expression of at least one abnormal NKp30 protein isoform, but also encompasses the abnormal expression of at least one normal NKp30 protein isoform, due for example to an abnormal transcription of the mRNA encoding a normal NKp30 protein (such abnormal transcription can be a decreased, or on the contrary increased, transcription compared to a control or standard level or amount, induced for example by an abnormal alternative splicing, by a cancer treatment and/or by the cancer itself). Similarly, the activity level of a NKp30 protein isoform may reflect an abnormal expression of at least one normal NKp30 protein isoform, or the expression of at least one abnormal NKp30 protein isoform.

Abnormal expression or activity of NKp30 protein isoform(s), such as abnormal NKp30 protein isoform(s) expression, refers to an expression or activity that is in some manner different from the expression or activity of the protein(s) in a normal (wild type) situation as explained further below, when compared to a control or standard.

It refers in particular to expression or activity of at least one NKp30 protein isoform, possibly two of six, three of six, four of six, five of six NKp30 protein isoform(s) or all NKp30 proteins isoforms encoded by NCR3 in a subject, that is in some manner different from expression or activity of the protein(s) in a normal (wild type) situation when compared to a control or standard.

Controls or standards appropriate for comparison to a sample, for the determination of abnormality, include samples believed to be normal (for example samples of a healthy subject) or corresponding to a population of patients suffering of a cancer but beneficing of favourable clinical criteria as explained previously, as well as laboratory values, even though possibly arbitrarily set, keeping in mind that such values may vary from laboratory to laboratory.

Laboratory standards and values may be set based on a known or determined population value and may be supplied in the format of a graph or table that permits easy comparison of measured, experimentally determined values.

The term abnormal NKp30 protein isoform includes but is not necessarily limited to: (1) a ponctual variation or mutation in the sequence of the protein such that one or more of the amino acid residues is different; (2) a short deletion or addition of one or a few amino acid residues to the sequence of the protein; (3) a longer deletion or addition of amino acid residues, such that an entire protein domain or sub-domain is removed or added; (4) expression of a decreased, or on the contrary increased, amount of the functional protein isoform, compared to a control or standard amount; (5) alteration of the cellular localization or targeting of the protein isoform; (6) alteration of the temporally regulated expression of the protein isoform (such that the protein is expressed when it normally would not be, or alternatively is not expressed when it normally would be); and (7) alteration of the localized (e. g, organ or tissue specific) expression of the protein isoform (such that the protein is not expressed where it would normally be expressed or is expressed where it normally would not be expressed), each compared to a control or standard.

The term "NKp30 protein isoform activity" encompasses any direct binding of NKp30 to one of its naturally occurring ligand, any indirect binding mediated or favoured by NKp30, as well as the effects of said direct or indirect bindings notably on the downstream effectors of the NKp30 pathway, such as CD3ζ, KARAP/DAP12, DAP10, FcRγ for example.

As used in the present application, the term "NCR3 gene" designates the Natural Cytotoxicity-triggering Receptor 3 gene on human chromosome 6p21.3 in the major histocompatibility complex (MHC) class Ill region, in close proximity to the TNF gene, as well as variants, analogs and fragments thereof, including alleles thereof (e.g., germline mutations) which are related to susceptibility to cancer. The NCR3 gene may also be referred to as NKp30 gene.

Recombinant nucleic acids may be prepared by conventional techniques, including chemical synthesis, genetic engineering, enzymatic techniques, or a combination thereof. Suitable NCR3 gene sequences may be found on gene banks, such as NCBI (Reference assembly: NC_000006.10 (31668740-31664650); RefSeq DNA: NM 147130; GeneID: 259197), Ensembl (Ensembl Gene ID: ENSG00000204475). The corresponding polypeptidic sequence is found under the reference NP_667341.1 (RefSeq peptide) in the NCBI gene Bank.

The term "NCR3 gene" includes any variant, fragment or analog of SEQ ID NO: 1 NC_000006.10 (31668933-31664651) or of any coding sequence as identified above.

A specific example of a NKp30 protein or polypeptide comprises all or part of a peptide selected from the group consisting of the Vega peptide ID: OTTHUMP00000014845 ["short tail-variable Ig-like domain" isoform (SHORT-WT)—SEQ ID NO: 2], Vega peptide ID: OTTHUMP00000014846 ["intermediate tail-variable Ig-like domain" isoform (INTER-WT)—SEQ ID NO: 3], Vega peptide ID: OTTHUMP00000014844 ["long tail-variable Ig-like domain" isoform (LONG-WT)—SEQ ID NO: 4], Vega peptide ID: none ["short tail-constant Ig-like domain" isoform (SHORT-DEL)—SEQ ID NO: 5], Vega peptide ID: OTTHUMP00000014847 ["intermediate tail-constant Ig-like domain" isoform (INTER-DEL)—SEQ ID NO: 6], and Vega peptide ID: none ["long tail-constant Ig-like domain" isoform (LONG-DEL)—SEQ ID NO: 7].

Polymorphisms can be referred to, for instance, by the nucleotide position at which the variation exists, by the change in amino acid sequence caused by the nucleotide variation, or by a change in some other characteristic of the nucleic acid molecule that is linked to the variation (e. g., an alteration of a secondary structure such as a stem-loop, or an alteration of the binding affinity of the nucleic acid for associated molecules, such as polymerases, RNases, and so forth). By way of example, the polymorphism disclosed herein in the region of the NCR3 gene can be referred to by its location in the NCR3 gene [e. g., based on the numerical position of the variant residues 3571 G/T (Reference SNP Cluster Report: rs3179003) or 3790 T/C (Reference SNP Cluster Report: rs986475], based on the numerical position of the variant amino acid in an NKp30 polypeptide, by the effect it has on the secondary structure of the NCR3 mRNA or by the effect it has on the tertiary structure of the NKp30 polypeptide (e.g., an alteration of the binding affinity of the polypeptide for ligands such as heparan sulfates and BAT3).

Detection/Diagnosis

Using the above mentioned observations, inventors now herein provides methods based on analyses of the NCR3 gene locus in a subject and/or on the monitoring of the NKp30 RNA transcript or protein isoforms in a subject.

Within the context of the present invention, the term "diagnosis" includes the detection, dosing, comparison, etc., at various stages, including early, pre-symptomatic stages, and late stages in a subject as defined above. Diagnosis typically includes the prognosis and characterization of a subject, to define most appropriate treatment (pharmacogenetics), etc.

A general object herein described resides in a method of assessing the prognosis of a cancer in a subject, the method comprising detecting, in particular in vitro or ex vivo, the presence of a mutated Natural Cytotoxicity-triggering Receptor 3 (NCR3) nucleic acid, an abnormal (relative) amount of at least one particular Natural Killer p30 (NKp30) RNA transcript isoform, and/or an abnormal expression or activity of at least one NKp30 protein isoform in a sample from the subject, the presence of said mutated NCR3 nucleic acid, abnormal (relative) amount of at least one particular NKp30 RNA transcript, or abnormal expression or activity of at least one NKp30 protein isoform being indicative of an unfavourable prognosis of the cancer in said subject.

Another general object herein described resides in a method of assessing the sensitivity of a subject to a treatment of cancer, such as a paediatric tumor, in particular neuroblastoma, which method comprises detecting, in vitro or ex vivo, the presence of (i) a mutated NCR3 nucleic acid, (ii) an abnormal (relative) amount of at least one particular NKp30 RNA transcript isoform, and/or (iii) an abnormal expression or activity of at least one particular NKp30 protein isoform in a sample from the subject, the presence of said mutated NCR3 nucleic acid, abnormal (relative) amount of at least one particular NKp30 RNA transcript isoform, or abnormal expression or activity of at least one particular NKp30 protein isoform being indicative of a resistance to said treatment. The detection step of the method of assessing the efficacy of a treatment of cancer in a subject is ideally performed prior to, during and/or after said treatment.

A further general object herein described resides in a method of assessing the efficacy of a treatment of cancer in a subject, such as GIST, which method comprises detecting, prior to, during and/or after said treatment, the presence of (i) a mutated NCR3 nucleic acid, (ii) an abnormal (relative) amount of at least one particular NKp30 RNA transcript isoform, and/or (iii) an abnormal expression or activity of at least one particular NKp30 protein isoform in a sample from the subject, the presence of said mutated NCR3 nucleic acid, abnormal (relative) amount of at least one particular NKp30 RNA transcript isoform, or abnormal expression or activity of at least one particular NKp30 protein isoform being indicative of a resistance to said treatment.

Further objects are methods as described above comprising a first step of providing a sample from the subject.

According to the present invention, the treatment towards which the sensitivity of a subject can be assessed is preferably selected from at least one of a chemotherapy, including for example administration of an alkylating agent, an anthracycline, such as DOX (doxorubicin, Idarubicine, 4 Epirubucine, mitoxanthrone), oxali-platinum and cis-platinum (PLAT); a therapy including administration of a tyrosine kinase inhibitor (TKI), such as imatinib mesylate (STI571) or sunitinib malate (SU11248); a therapy including administration of a farnesyl-transferase inhibitor (FTI); and a radiotherapy implying X-rays (XR) for example.

Diagnostic methods, which analyse and predict sensitivity or response to a treatment or drug as mentioned above, or side effects to a treatment or drug, may be used to determine whether a subject should be treated with a particular treatment drug. For example, if the method indicates a likelihood that a subject, in particular a subject with a normal NKp30 isoform expression profile, in particular a normal NKp30 RNA transcript isoform profile, will respond positively to a TKI, a FTI, and/or to an anthracycline, PLAT and/or XR, said treatment(s) may be administered to the individual. Conversely, if the method indicates that an individual or a subject, in particular a subject with an abnormal NKp30 isoforms expression profile, is likely to respond negatively to said treatment, an alternative course of treatment may be prescribed.

A negative response may be defined as either the absence of an efficacious response or the presence of toxic side effects. This means the treatment appears non efficient to prevent or treat a cancer. In other words, the subject in need of a treatment, or the cancer itself, appears resistant to said treatment. A poor response is a response significantly inferior to the response observed in patients who carry a wild-type NCR3 or express functional NKp30 protein isoform(s).

The presence of a mutated NCR3 nucleic acid, of an abnormal (relative) amount of at least one particular NKp30 RNA transcript isoform, and/or of an abnormal expression or activity of at least one NKp30 protein isoform is indicative of a resistance, i.e., a negative or poor response of the subject to a treatment of cancer, or, as explained previously, is indicative of the presence of toxic side effects.

The NCR3 mutation may be determined in the NCR3 genomic sequence or in the RNA.

The detected mutation may be an innate or acquired mutation.

The mutation in the NCR3 gene locus may be any form of mutation(s), deletion(s), rearrangement(s) and/or insertions in the coding and/or non-coding region of the locus, alone or in various combination(s). Mutations more specifically include point mutations. Deletions may encompass any region of one, two or more residues in a coding or non-coding portion of the gene locus, such as from one residue up to the entire gene or locus. Typical deletions affect smaller regions, such as domains (introns) or repeated sequences or fragments of less than about 20 consecutive base pairs, although larger deletions may occur as well. Insertions may encompass the addition of one or several residues in a coding or non-coding portion of the gene locus. Insertions may typically comprise an addition of between 1 and 20 base pairs in the gene locus. Rearrangement includes inversion of sequences. The NCR3 gene locus mutation may result in the creation of stop codons, frameshift mutations, amino acid substitutions, particular RNA splicing or processing, product instability, truncated polypeptide production, etc. The alteration may result in the production of at least one, possibly two, three, four, five or six NKp30 splicing variant(s) (or splice form(s)) with altered function, stability, targeting or structure. The alteration may also cause a reduction in protein isoform expression or, alternatively, an increase in said production.

In a particular embodiment of the method according to the present invention, the alteration in the NCR3 gene is selected from a point mutation, a deletion and an insertion in the NCR3 gene or corresponding expression product, more preferably a point mutation, even more preferably a single nucleotide polymorphism (SNP).

The present invention in particular now discloses mutated NCR3 human nucleic acid sequences.

A particular example of a mutated NCR3 human nucleic acid sequence comprises a point mutation, preferably a single nucleotide polymorphism (SNP) selected from a SNP leading to the substitution of a guanine (G) to the thymine (T) at position 3571 (3571 G/T) (position relative to ATG start codon) of Seq ID: 1 [NC_000006.10 (31668933-31664651), (Reference SNP Cluster Report: rs3179003)], and a SNP leading to the substitution of a cytosine (C) to the Thymine (T) at position 3790 (3790 T/C) (position relative to ATG start codon) of Seq ID: 1 [NC_000006.10 (31668933-31664651), (Reference SNP Cluster Report: rs986475)].

A particular method of determining or assessing the prognosis of a cancer in a subject, the sensitivity of a subject to a treatment of cancer or the efficacy, in a subject, of a treatment of cancer, comprises the detection of the presence, in a sample from the subject, of a mutated NCR3 sequence comprising a point mutation, preferably a single nucleotide polymorphism (SNP) selected from a SNP leading to the substitution of a guanine (G) to the thymine (T) at position 3571 (3571 G/T) (position relative to ATG start codon) of Seq ID NO: 1 [NC_000006.10 (31668933-31664651)], in a sample from the subject, the detection of the presence of a mutated NCR3 sequence comprising such a point mutation being indicative of an unfavourable prognosis of the cancer in said subject, or of a resistance of the subject to the treatment of cancer.

In a further embodiment, the present description provides a method of determining or assessing the prognosis of a cancer in a subject, the sensitivity of a subject to a treatment of cancer or the efficacy, in a subject, of a treatment of cancer, the method comprising detecting the presence, in a sample from the subject, of a mutated NCR3 nucleic acid sequence comprising a point mutation, preferably a SNP leading to the substitution of a cytosine (C) to the Thymine (T) at position 3790 (3790 T/C) (position relative to ATG start codon) of Seq ID NO: 1 [NC_000006.10 (31668933-31664651)], the detection of the presence of a mutated NCR3 sequence comprising such a point mutation being indicative of an unfavourable prognosis of the cancer in said subject, or of an unfavourable or negative response of the subject to the treatment of cancer.

The methods herein described may further comprise a step the aim of which is to determine whether the subject is homozygous or heterozygous for the polymorphism.

In the methods of this invention, any mutation or alteration in the NCR3 gene may be assessed in combination with other markers such as other mutations or alterations in any other gene or protein.

The presence of a mutated NCR3 nucleic acid in the sample can be detected through the genotyping of the sample. The detection can be performed by sequencing all or part of the NCR3 gene, using selective hybridization and/or amplification of all or part of the NCR3 gene. More preferably a NCR3 gene specific amplification is carried out before the mutation identification step.

In a particular embodiment herein described, the presence of a mutated NCR3 nucleic acid is detected by using restriction digestion, sequencing, selective hybridisation, in particular with a nucleic acid probe, for example a nucleic acid probe in suspension or present on a nucleic acid array, and/or selective amplification.

A specific embodiment comprises the detection of the presence of at least one SNP in the NCR3 gene sequence of a subject.

In a particular embodiment, the methods herein described comprise detecting the presence of an abnormal NCR3 RNA expression. Abnormal NCR3 expression includes the presence of a mutated RNA sequence, the presence of an abnormal RNA splicing or processing, the presence of an abnormal quantity of RNA, etc. These may be detected by various techniques known in the art, including restriction digestion, sequencing of all or part of the NCR3 RNA, selective hybridisation or selective amplification of all or part of said RNA or of the corresponding synthesized cDNA, for instance.

An abnormal RNA splicing can induce the transcription of an abnormal quantity of RNA encoding one or more particular splicing variants (or called herein "splice forms" or "RNA transcript isoforms") of NKp30 selected from the splice forms appearing on FIGS. 2 and 15, and/or can induce the transcription of an abnormal form, as herein defined, of at least one of said variants, possibly two, three, four, five or of all of said variants or RNA transcript isoforms.

The herein described methods may comprise a step of determining the NKp30 protein expression or activity by measuring and comparing, in a sample of a subject, the relative amounts of:

- long tail-constant or tail-variable Ig-like domain and intermediate tail-constant or tail-variable Ig-like domain RNA transcripts of NKp30,
- long tail-constant or tail-variable Ig-like domain and short tail-constant or tail-variable Ig-like domain RNA transcripts of NKp30,
- intermediate tail-constant or tail-variable Ig-like domain and short tail-constant or tail-variable Ig-like domain RNA transcripts of NKp30, or
- long tail-constant or tail-variable Ig-like domain, intermediate tail-constant or tail-variable Ig-like domain and short tail-constant or tail-variable Ig-like domain RNA transcripts of NKp30, or by comparing each amount of a particular isoform or each relatives amounts of at least two, preferably three distinct isoforms to control, reference or mean relative values.

In particular, an increased (relative) amount of the intermediate tail-constant or tail-variable Ig-like domain RNA transcript of NKp30 and a decreased (relative) amount of the long tail-constant or tail-variable Ig-like domain RNA transcript and/or of the short tail-constant or tail-variable Ig-like domain RNA transcript of NKp30 compared to control relative values, are indicative of an unfavourable prognosis of a cancer in a subject or of a resistance to a treatment of cancer.

In a further embodiment, the method comprises detecting the presence of an abnormal expression of at least one NKp30 polypeptide or protein isoform. Abnormal expression refers to the presence of a mutated polypeptide isoform sequence, the presence of an abnormal (relative) quantity of NKp30 polypeptide or protein isoform(s), the presence of an abnormal tissue distribution, etc.

These may be detected by various techniques known in the art, including by amplifying and/or binding to specific ligands (such as antibodies), for instance.

Other suitable methods may be used to detect or quantify abnormal NCR3 gene or RNA expression or sequence. They include allele-specific oligonucleotide (ASO), allele-specific amplification, Southern blot (for DNAs), Northern blot (for RNAs), single-stranded conformation analysis (SSCA), PFGE, fluorescent in situ hybridization (FISH), gel migration, clamped denaturing gel electrophoresis, heteroduplex analysis, RNase protection, chemical mismatch cleavage, ELISA, radio-immunoassays (RIA) and immuno-enzymatic assays (IEMA).

As explained previously, in a particular embodiment, the method comprises detecting or determining the presence of an abnormal NCR3 nucleic acid in a sample from the subject. This can be accomplished as explained previously by using restriction digestion, sequencing, selective hybridization and/or selective amplification of nucleic acids present in said sample.

Restriction digestion can be carried out using techniques and enzymes well known in the art.

Sequencing can be carried out using techniques well known in the art, using automatic sequencers. The sequencing may be performed on the complete NCR3 gene or, more preferably, on specific domains thereof, typically those known or suspected to carry deleterious mutations or other alterations.

Amplification is based on the formation of specific hybrids between complementary nucleic acid sequences that serve to initiate nucleic acid reproduction.

Amplification may be performed according to various techniques known in the art, such as by polymerase chain reaction (PCR), reverse transcription PCR (RT-PCR), ligase chain reaction (LCR), strand displacement amplification (SDA), nucleic acid sequence based amplification (NASBA) and Restriction fragment length polymorphism (RFLP).

These techniques can be performed using commercially available reagents and protocols. Preferred techniques use allele-specific PCR or PCR-SSCP. Amplification usually requires the use of specific nucleic acid primers, to initiate the reaction.

Nucleic acid primers, herein described, are useful for amplifying sequences from the NCR3 coding sequence (e.g., gene, or locus, or RNA), including surrounding regions.

Primers that can be used to amplify NCR3 target region may be designed based on the genomic or RNA sequence of NCR3 and, in particular, on the sequence of SEQ ID NO: 1.

Particular primers are complementary to and able to specifically hybridize with a portion of the NCR3 gene locus that flanks a target region of the NCR3 coding sequence.

The target region may be a region altered in certain subjects having a cancer, a predisposition to a cancer or an increase likelihood of developing a cancer.

In this regard, particular primers of this invention are specific for mutated sequences in a NCR3 gene or RNA. By using such primers, the detection of an amplification product indicates the presence of a mutation in the NCR3 gene locus. In contrast, the absence of amplification product indicates that the specific mutation is not present in the sample.

A typical nucleic acid primer usable in the methods herein disclosed is a primer that is complementary to and that hybridizes specifically to a mutated NCR3 sequence comprising a point mutation, typically a wild type NCR3 sequence comprising a point mutation, preferably a single nucleotide polymorphism (SNP) as defined previously.

Specific nucleic acid primers usable in the context of the present invention are disclosed below.

Examples of specific primers amplifying the region comprising the 3571 G/T polymorphism and allowing genotyping by sequencing are herein provided:

```
                                            (SEQ ID NO: 18)
    NCR3_Forward 5' CTGAACTTTCCCTTCCACCA 3', (SEQ ID NO: 19)
    NCR3_Reverse 5' GGTCCAGCCAGTAAAAACCA 3'.
```

These sequences may be used to amplify a fragment of 471 bp.

The TAQMAN Genotyping assay ID: C_25630865_10 can be used to genotype the 3571 G/T polymorphism.

Examples of specific primers amplifying the region comprising the 3790 T/C polymorphism and allowing genotyping by sequencing are herein provided:

```
                                            (SEQ ID NO: 18)
    NCR3_Forward 5' CTGAACTTTCCCTTCCACCA 3', (SEQ ID NO: 19)
    NCR3_Reverse 5' GGTCCAGCCAGTAAAAACCA 3'.
```

These sequences may be used to amplify a fragment of 471 bp.

The TAQMAN Genotyping assay ID: C_7514908_10 can be used to genotype the 3790 T/C polymorphism.

The target region may further be a region encoding a particular NKp30 RNA transcript.

Examples of nucleic acid primers amplifying such a target region are disclosed in the experimental section (SEQ ID NO: 20 to 30 and 48).

The presence of a particular NKp30 RNA transcript isoform may be detected in a method as herein disclosed by using selective amplification with a nucleic acid primer that allows amplification of the particular NKp30 RNA transcript isoform, or allows to discriminate between long, intermediate and short RNA transcript isoforms of NKp30 and/or between constant and variable Ig-like domain transcript isoforms.

Examples of specific primers amplifying particular NKp30 RNA transcript isoforms are described below:

Examples of specific primers amplifying the NKp30 RNA SHORT-WT transcript for quantification based on SYBR-GREEN detection are herein provided:

```
                                     (SEQ ID NO: 20)
NCR3_Forward 5' GTGAGGAATGGAACCCCAGAGT 3', (SEQ ID NO: 23)
NCR3_Reverse 5' CCGGAGAGAGTAGATTTGGCATATT 3'.
```

These sequences may be used to amplify a fragment of 323 bp.

Examples of specific primers amplifying the NKp30 RNA SHORT-DEL transcript for quantification based on SYBR-GREEN detection are herein provided:

```
                                     (SEQ ID NO: 21)
NCR3_Forward 5' GTGGTTCCAGGGAAGGAGGC 3', (SEQ ID NO: 23)
NCR3_Reverse 5' CCGGAGAGAGTAGATTTGGCATATT 3'.
```

These sequences may be used to amplify a fragment of 266 bp.

Examples of specific primers amplifying the NKp30 RNA INTER-WT transcript for quantification based on SYBR-GREEN detection are herein provided:

```
                                     (SEQ ID NO: 20)
NCR3_Forward 5' GTGAGGAATGGAACCCCAGAGT 3', (SEQ ID NO: 22 or 27)
NCR3_Reverse 5' TTCCCATGTGACAGTGGCATT 3'.
```

These sequences may be used to amplify a fragment of 319 bp.

Examples of specific primers amplifying the NKp30 RNA INTER-DEL transcript for quantification based on SYBR-GREEN detection are herein provided:

```
                                     (SEQ ID NO: 21)
NCR3_Forward 5' GTGGTTCCAGGGAAGGAGGC 3', (SEQ ID NO: 22 or 27)
NCR3_Reverse 5' TTCCCATGTGACAGTGGCATT 3'.
```

These sequences may be used to amplify a fragment of 262 bp.

Examples of specific primers amplifying the NKp30 RNA LONG-WT transcript for quantification based on SYBR-GREEN detection are herein provided:

```
                                     (SEQ ID NO: 20)
NCR3_Forward 5' GTGAGGAATGGAACCCCAGAGT 3', (SEQ ID NO: 24)
NCR3_Reverse 5' TGGACCTTTCCAGGTCAGACATT 3'.
```

These sequences may be used to amplify a fragment of 321 bp.

Examples of specific primers amplifying the NKp30 RNA LONG-DEL transcript for quantification based on SYBR-GREEN detection are herein provided:

```
                                     (SEQ ID NO: 21)
NCR3_Forward 5' GTGGTTCCAGGGAAGGAGGC 3', (SEQ ID NO: 24)
NCR3_Reverse 5' TGGACCTTTCCAGGTCAGACATT 3'.
```

These sequences may be used to amplify a fragment of 264 bp.

Examples of specific primers amplifying the NKp30 RNA SHORT-WT transcript for quantification based on TAQMAN PROBE detection are herein provided:

```
                                     (SEQ ID NO: 25)
NCR3_Forward 5' TTTCCTCCATGACCACCAGG 3', (SEQ ID NO: 28)
NCR3_Reverse 5' CGGAGAGAGTAGATTTGGCATATT 3', (SEQ ID NO: 30)
NCR3_Probe   5' AGCTGCACATCCGGGACGTGC 3',
```

NCR3 or NKP30 Probe (6-FAM/TAMRA):

```
                                     (SEQ ID NO: 48)
         5' TGGTGGAGAAAGAACATCCTCAGCTAGGG 3'.
```

These sequences may be used to amplify a fragment of 266 bp.

Examples of specific primers amplifying the NKp30 RNA SHORT-DEL transcript for quantification based on TAQMAN PROBE detection are herein provided:

```
                                     (SEQ ID NO: 26)
NCR3_Forward 5' GGTTCCAGGGAAGGAGGCT 3', (SEQ ID NO: 28)
NCR3_Reverse 5' CGGAGAGAGTAGATTTGGCATATT 3', (SEQ ID NO: 30)
NCR3_Probe   5' AGCTGCACATCCGGGACGTGC 3',
```

NCR3 or NKP30 Probe (6-FAM/TAMRA):

```
                                     (SEQ ID NO: 48)
         5' TGGTGGAGAAAGAACATCCTCAGCTAGGG 3'.
```

These sequences may be used to amplify a fragment of 263 bp.

Examples of specific primers amplifying the NKp30 RNA INTER-WT transcript for quantification based on TAQMAN PROBE detection are herein provided:

```
                                     (SEQ ID NO: 25)
NCR3_Forward 5' TTTCCTCCATGACCACCAGG 3',
```

```
                              (SEQ ID NO: 27 or 22)
NCR3_Reverse 5' TTCCCATGTGACAGTGGCATT 3', (SEQ ID NO: 30)
NCR3_Probe 5' AGCTGCACATCCGGGACGTGC 3',
```

NCR3 or NKP30 Probe (6-FAM/TAMRA):

```
                                          (SEQ ID NO: 48)
      5' TGGTGGAGAAAGAACATCCTCAGCTAGGG 3'.
```

These sequences may be used to amplify a fragment of 263 bp.

Examples of specific primers amplifying the NKp30 RNA INTER-DEL transcript for quantification based on TAQ-MAN PROBE detection are herein provided:

```
                                     (SEQ ID NO: 26)
NCR3_Forward 5' GGTTCCAGGGAAGGAGGCT 3', (SEQ ID NO: 27 or 22)
NCR3_Reverse 5' TTCCCATGTGACAGTGGCATT 3', (SEQ ID NO: 30)
NCR3_Probe 5' AGCTGCACATCCGGGACGTGC 3',
```

NCR3 or NKP30 Probe (6-FAM/TAMRA):

```
                                          (SEQ ID NO: 48)
      5' TGGTGGAGAAAGAACATCCTCAGCTAGGG 3'.
```

These sequences may be used to amplify a fragment of 260 bp.

Examples of specific primers amplifying the NKp30 RNA LONG-WT transcript for quantification based on TAQMAN PROBE detection are herein provided:

```
                                     (SEQ ID NO: 25)
NCR3_Forward 5' TTTCCTCCATGACCACCAGG 3', (SEQ ID NO: 29)
NCR3_Reverse 5' GGACCTTTCCAGGTCAGACATT 3', (SEQ ID NO: 30)
NCR3_Probe 5' AGCTGCACATCCGGGACGTGC 3',
```

NCR3 or NKP30 Probe (6-FAM/TAMRA):

```
                                          (SEQ ID NO: 48)
      5' TGGTGGAGAAAGAACATCCTCAGCTAGGG 3'.
```

These sequences may be used to amplify a fragment of 264 bp.

Examples of specific primers amplifying the NKp30 RNA LONG-DEL transcript for quantification based on TAQ-MAN PROBE detection are herein provided:

```
                                     (SEQ ID NO: 26)
NCR3_Forward 5' GGTTCCAGGGAAGGAGGCT 3', (SEQ ID NO: 29)
NCR3_Reverse 5' GGACCTTTCCAGGTCAGACATT 3', (SEQ ID NO: 30)
NCR3_Probe 5' AGCTGCACATCCGGGACGTGC 3',
```

NCR3 or NKP30 Probe (6-FAM/TAMRA):

```
                                          (SEQ ID NO: 48)
      5' TGGTGGAGAAAGAACATCCTCAGCTAGGG 3'.
```

These sequences may be used to amplify a fragment of 261 bp.

Hybridization detection methods are based on the formation of specific hybrids between complementary nucleic acid sequences that serve to detect specific sequences, in particular NCR3 nucleic acid sequence mutation(s) or specific NKp30 RNA transcript isoforms.

A particular detection technique involves the use of a nucleic acid probe specific for the wild-type or a mutated NCR3 gene or for a NKp30 RNA transcript isoform, followed by the detection of the presence of an hybrid. The probe may be in suspension or immobilized on a substrate or support (as in nucleic acid array technologies). The probe is typically labelled to facilitate detection of hybrids. Such nucleic acid probes are herein disclosed.

Typical hybridization detection methods comprises the following steps of contacting the sample from the subject with a nucleic acid probe specific for a NCR3 nucleic acid (preferably gene locus), in particular a mutated NCR3 nucleic acid, and assessing the formation of an hybrid.

In a particularly preferred embodiment, the method comprises contacting simultaneously the sample with a set of probes that are specific, respectively, for wild type NCR3 gene locus and for various abnormal or mutated forms thereof. In this embodiment, it is possible to detect directly the presence of various forms of mutations in the NCR3 gene locus in the sample. Also, various samples from various subjects may be treated in parallel.

The presence of a mutated NCR3 nucleic acid may thus be detected, in a method as herein disclosed, by using selective hybridisation with at least one nucleic acid probe, in particular a nucleic acid probe in suspension or present on a nucleotide array, that hybridizes with a specific NKp30 RNA transcript isoform, or allows to discriminate between long, intermediate and short RNA transcript isoforms of NKp30 and/or between constant and variable Ig-like domain transcript isoforms.

A particular method herein disclosed the aim of which is to assess the sensitivity/response of a subject to a treatment of a cancer, or to assess the prognosis of a cancer in a subject, can comprise a step of obtaining from the subject a test sample of DNA, preferably a sample of DNA suspected or known to comprise a NCR3 sequence. The method preferably comprises the following step of (a) contacting a test DNA sample from a subject with at least one nucleic acid probe, wherein said nucleic acid probe is complementary to and specifically hybridises with a mutated NCR3 sequence, such as one of those herein described, to form a hybridization sample, (b) maintaining the hybridization sample under conditions suitable for allowing specific hybridization of the NCR3 sequence with the at least one nucleic acid probe to occur, and (c) detecting whether there is specific hybridization of the NCR3 sequence with the at least one nucleic acid probe.

Specific hybridization of the NCR3 sequence with a nucleic acid probe may be used to indicate an unfavourable, or on the contrary a favourable, prognosis of the cancer in the subject.

Specific hybridization of the NCR3 sequence with a nucleic acid probe may further be used to identify the response (resistance or sensitivity) of a cancer to the treatment administered to the subject.

As explained previously, particular mutated NCR3 sequences, in particular a NCR3 sequence comprising the non-synonymous NCR3*3571 G/T (R174S-rs3179003) mutation, are associated with an unfavourable prognosis of the cancer, and with resistance to a treatment of a particular cancer, as well as other mutated NCR3 sequences, in particular a NCR3 sequence comprising the NCR3*3790 T/C (rs986475) mutation.

The treatment is preferably selected from a chemotherapy, in particular a chemotherapy including administration of an alkylating agent or an anthracycline, such as DOX, and/or oxali-platinum or cis-platinum (PLAT); a therapy including administration of a TKI such as imatinib mesylate (STI571) or sunitinib malate (SU11248); a therapy including administration of a FTI; and a radiotherapy preferably including X-rays (XR).

Typical stringent hybridisation conditions include temperatures above 30° C., preferably above 35° C., more preferably in excess of 42° C., and/or salinity of less than about 500 mM, preferably less than 200 mM. Hybridization conditions may be adjusted by the skilled person by modifying the temperature, salinity and/or the concentration of other reagents such as SDS, SSC, etc.

For purposes of the present disclosure, "stringent conditions" encompass conditions under which hybridization will only occur if there is less than 25% mismatch between the hybridization molecule and the target sequence.

Within the context of this invention, a probe refers to a polynucleotide sequence which is complementary to and capable of specific hybridisation with a (target portion of a) NCR3 gene or RNA, and which is suitable for detecting polynucleotide polymorphisms associated with NCR3 alleles as described previously. Probes are preferably perfectly complementary to the NCR3 gene, RNA, or target portion thereof. Probes typically comprise single-stranded nucleic acids of between 15 to 100 nucleotides in length, preferably of between 20 and 50 nucleotides in length. It should be understood that longer probes may be used as well. A preferred probe of this invention is a single stranded nucleic acid molecule of between 20 to 30 nucleotides in length, which can specifically hybridise to a region of a NCR3 nucleic acid (for example gene or RNA) that carries an alteration.

Nucleic acid probe specific for an abnormal (e.g., a mutated) NCR3 sequence (gene or RNA in particular), i.e., a nucleic acid probe that specifically hybridises to said abnormal NCR3 sequence and essentially does not hybridise to a normal (reference) NCR3 sequence, are herein usable. Specificity indicates that hybridisation to the target sequence generates a specific signal which can be distinguished from the signal generated through non-specific hybridisation. Perfectly complementary sequences are herein preferred. It should be understood, however, that certain mismatch may be tolerated, as long as the specific signal may be distinguished from non-specific hybridisation.

The sequence of the probe can be readily prepared based on any sequences of the NCR3 gene or RNA carrying a mutation, in particular a point mutation such as a SNP, linked to the sensitivity of a subject to a treatment of cancer, or to a favourable prognosis of a cancer in a subject.

It is also appropriate to generate probes and primers based on fragments or portions of these nucleic acid molecules, for instance regions that encompass the above identified polymorphisms in the NCR3 sequence.

A typical mutated NCR3 sequence indeed usable in the methods herein described comprises the wild type sequence of NCR3 and a point mutation, preferably a single nucleotide polymorphism (SNP) as described previously.

Nucleotide substitutions may be performed, as well as chemical modifications of the probe. Such chemical modifications may be accomplished to increase the stability of hybrids (e.g., intercalating groups) or to label the probe. Typical examples of labels include, without limitation, radioactive isotopes, enzyme substrates, cofactors, ligands, chemiluminescent or fluorescent agents, haptens, and enzymes.

Methods for labelling and guidance in the choice of labels appropriate for various purposes are discussed, e. g., in Sambrook etal. (In Molecular Cloning. A Laboratory Manual, CSHL, New York, 1989) and Ausubel et al. (In Current Protocols in Molecular Biology, John Wiley & Sons, New York, 1998).

The invention also concerns the use of a nucleic acid probe or a primer as herein described in a method of assessing the sensitivity of a subject to a treatment of cancer or in a method of assessing the prognosis of a cancer in a subject.

The methods disclosed herein of assessing the sensitivity of a subject to a treatment of cancer, of assessing the efficacy of a treatment of cancer, or of assessing the prognosis of a cancer in a subject, may further be performed, as indicated above, by detecting an abnormal expression or activity of at least one NKp30 protein isoform which may be innate or acquired, in a test sample from the subject, using a ligand identified for binding to such abnormal NKp30 protein.

Preferred methods according to the invention, comprise the steps of contacting the sample from the subject with a ligand identified for binding to a NKp30 protein isoform (a normal NKp30, e.g., a wild-type NKp30, or an abnormal NKp30) and assessing whether a binding occur or not between the subject NKp30 and said NKp30 ligand, for example by determining the formation of a complex between said subject NKp30 and said NKp30 ligand.

Particularly preferred methods herein disclosed comprise a step of determining the presence of a particular NKp30 protein isoform, by contacting the sample from the subject with a ligand identified for specifically binding to said particular NKp30 protein isoform.

A ligand is an agent that specifically binds to a defined target.

The term "specifically" means that less than 10%, preferably less than 5% of the agent bind a target different from said defined target. Thus, a NKp30 protein isoform-specific ligand binds substantially only a NKp30 protein, i.e., in the context of the present invention, a NKp30 protein isoform. Different types of ligands may be used, such as specific antibodies and other agents (and functional fragments thereof) that bind substantially only to the NKp30 protein isoform.

A preferred ligand herein disclosed is a ligand identified for specifically binding to a particular normal NKp30 protein isoform or to an abnormal NKp30 protein isoform.

Anti-NKp30 protein antibodies, in particular antibody specific for a particular NKp30 protein isoform, are herein disclosed and may be produced using standard procedures described in a number of texts, including Harlow and Lane (Antibodies, A Laboratory Manual, CSHL, New York, 1988). The determination that a particular ligand binds substantially only to a NKp30 protein isoform or to a particular NKp30 splicing variant, splice form or NKp30 RNA transcript isoform, may readily be made by using or adapting routine procedures. One suitable in vitro assay makes use of the Western blotting procedure (described in many standard texts, including Harlow and Lane (Antibodies, A Laboratory Manual, CSHL, New York, 1988)). Western blotting may be used to determine that a given NKp30 protein binding agent, such as an anti-NKp30 protein monoclonal antibody, binds substantially only to a particular NKp30 protein, i.e., in the context of the present invention, to a particular NKp30 protein isoform.

Within the context of this invention, an antibody designates a polyclonal antibody, a monoclonal antibody, as well as fragments or derivatives thereof having substantially the same antigen specificity.

Shorter fragments of antibodies can also serve as specific binding agents. For instance, FAbs, Fvs, and single-chain Fvs (SCFvs) that bind to a particular NKp30 would be NKp30-specific binding ligands.

These antibody fragments are defined as follows: (1) FAb, the fragment which contains a monovalent antigen-binding fragment of an antibody molecule produced by digestion of whole antibody with the enzyme papain to yield an intact light chain and a portion of one heavy chain; (2) FAb', the fragment of an antibody molecule obtained by treating whole antibody with pepsin, followed by reduction, to yield an intact light chain and a portion of the heavy chain; two FAb' fragments are obtained per antibody molecule; (3) (FAb') 2, the fragment of the antibody obtained by treating whole antibody with the enzyme pepsin without subsequent reduction; (4) F (Ab') 2, a dimer of two FAb' fragments held together by two disulfide bonds; (5) Fv, a genetically engineered fragment containing the variable region of the light chain and the variable region of the heavy chain expressed as two chains; and (6) single chain antibody ("SCA"), a genetically engineered molecule containing the variable region of the light chain, the variable region of the heavy chain, linked by a suitable polypeptide linker as a genetically fused single chain molecule. Methods of making these fragments are routine.

A particular antibody herein presented is specific for a NKp30 protein or polypeptide, typically a mutated NKp30 polypeptide, as defined previously and as herein exemplified.

Particular antibodies usable in the present invention may also be each specific for a particular wild-type NKp30 polypeptide isoform. Preferably the antibody comprises all or a distinctive part of a sequence selected from the extracellular domain of NKp30 (SEQ ID NO: 38 and 39) and from the intracellular domain of NKp30 (SEQ ID NO: 40 to 42). The NKp30 variable Ig-like extracellular domain is depicted in SEQ ID NO: 38. The amino acid peptide used to obtain specific anti-NKp30 variable Ig-like extracellular domain antibody is depicted in SEQ ID NO: 43. The NKp30 constant Ig-like extracellular domain is depicted in SEQ ID NO: 39. The amino acid peptide used to obtain specific anti-NKp30 constant Ig-like extracellular domain antibody is depicted in SEQ ID NO: 44. The NKp30 short intracellular domain is depicted in SEQ ID NO: 40. The amino acid peptide used to obtain specific anti-NKp30 short intracellular domain antibody is depicted in SEQ ID NO: 45. The NKp30 intermediate intracellular domain is depicted in SEQ ID NO: 41. The amino acid peptide used to obtain specific anti-NKp30 intermediate intracellular domain antibody is depicted in SEQ ID NO: 46. The NKp30 long intracellular domain is depicted in SEQ ID NO: 42. The amino acid peptide used to obtain specific anti-NKp30 long intracellular domain antibody is depicted in SEQ ID NO: 47.

Such sequences may further be conjugated to KLH as a carrier peptide.

Thus, in a specific embodiment, the sample is contacted with an antibody specific for an abnormal NKp30 protein or polypeptide and the formation of an immune complex is determined. Various methods for detecting an immune complex can be used, such as ELISA, radio-immunoassays (RIA) and immuno-enzymatic assays (IEMA).

Other ligands identified for binding to a particular NKp30 protein are for example heparane sulfates and BAT3.

Ligand may be detected using, in particular, a probe. The probe is preferably tagged.

In a particular embodiment, the present invention thus herein discloses a method for detecting the lack of immunogenicity of the tumor cells via NKp30 pathway, said method comprising contacting autologous tumor cells which have been treated with a TKI, an anthracycline, cis-platinum, oxali-platinum or X-rays and which express a NKp30 ligand, the absence of binding of said ligand being correlated to the lack of immunogenicity of the tumor cell.

Techniques well known from the man of the art such as ELISA binding assay or Western Blot (WB) may be applied in the above described methods.

Although non-specific binding may occur, binding to the target NKp30 polypeptide isoform occurs with a higher affinity and can be reliably discriminated from non-specific binding.

Contacting between the nucleic acids or proteins of the sample and the ligands or the probes previously described may be performed in any suitable device, such as a plate, tube, well, glass, etc. In specific embodiments, the contacting is performed on a nucleic acid array or on a specific probe or ligand array, such as a nucleic acid probe present on a nucleotide array.

The ligand, just like the probe previously described, may be in suspension or immobilized on a substrate or support.

The substrate may be a solid or semi-solid substrate such as any support comprising glass, plastic, nylon, paper, metal, polymers and the like. The substrate may be of various forms and sizes, such as a slide, a membrane, a bead, a column, a gel, etc.

The contacting may be made under any condition suitable for a complex to be formed between the reagent (ligand or probe) and the nucleic acids or polypeptides of the sample.

The sample may thus be contacted simultaneously, or in parallel, or sequentially, with various ligands or probes specific for different forms of a NCR3 nucleic acid, NKp30 RNA transcript, or NKp30 protein or polypeptide, such as wild-type, normal isoforms and various abnormal forms thereof.

The present invention further discloses methods comprising a step of determining the NKp30 activity.

NKp30 is mainly expressed in NK cells in vivo by considering three possible expression levels: (i) a clonal level, (ii) a subpopulation level, and (iii) the level of the total peripheral blood population. NKp30 signalling is critical for triggering secretion of pro-inflammatory cytokines (TNFα and IFNγ for example) and accelerating DC maturation.

In the present application, the abnormal NKp30 protein activity may thus also be correlated to the absence or presence of a secretion of, or to an alteration in the cellular level of a compound selected from, for example, TNFα and IFNγ. Such cellular level, in particular natural killer (NK) cell level, of TNFα and/or IFNγ may be measured in the methods herein disclosed by inventors comprising a step of determining the NKp30 protein activity. Such a measure may further be compared to a normal level.

An abnormal NKp30 activity may be detected by measuring the cellular level of IFNγ derived from purified NK cells) in a culture comprising NK cells and coated monoclonal antibody anti-NKp30, in the presence or absence of IL-2. The measured level is preferably compared to a reference level measured from a culture of NK cells in PBS (Phosphate Buffered Saline) in the presence or absence of IL-2).

An abnormal NKp30 activity may further be detected by measuring the cellular level of IFNγ (derived from purified NK cells) in a coculture comprising immature dendritic cells (DC) conditioned by TKI, and natural killer (NK) cells. DC are autologous cells from the subject to be tested or allogeneic cells. NK cells are preferably autologous cells. The coculture may be realized, in parallel, in the presence of at least one compound selected from NKp30 ligand and monoclonal antibody anti-NKp30, and in the absence of any of said compounds.

An abnormal NKp30 activity may further be detected by measuring the cellular level of IFNγ or TNFα (derived from PBMC) in a culture comprising peripheral blood mononuclear cells (PBMC) and coated monoclonal antibody anti-NKp30. The measured level is preferably compared to a reference level measured from a culture of PBMC without coated monoclonal antibody anti-NKp30.

The subject IFNγ or TNFα measured levels may be further compared to respective reference levels.

Inventors indeed discovered that an abnormal IFNγ or TNFα level (in particular a decreased value compared to known standards) is correlated to an abnormal NKp30 protein isoform expression or abnormal NKp30 proteins isoforms profile, in particular to the relative higher expression of the NKp30 intermediate isoform and decreased expression of the NKp30 short and/or long isoforms.

TNFα and IFNγ secretion may be determined by techniques well known in the art, such as ELISA, intracellular cytokine staining or cytokine secretion assay in flow cytometry.

The abnormal NKp30 protein isoform expression or activity may also be correlated to an abnormal transcription of normal NKp30 transcript isoform. The abnormal transcription can be an increased expression compared to a control or standard amount or level. It can also be an increased expression compared to a control or standard amount or level, for example induced by a cancer treatment or by the cancer itself.

The present invention provides a method comprising determining the NKp30 protein expression or activity by measuring the cellular level of mRNA encoding NKp30, an increased level compared to a control level being correlated to an abnormal NKp30 protein expression. The mRNA level may be measured, ex vivo or in vitro, on patient isolated PBMC, or patients isolated NK cells for example.

Such a method can include a step comprising the use of RT-PCR (Reverse Transcription-Polymerase Chain Transcription).

The methods described in the present application are thus, as indicated previously, preferably performed on a sample comprising cells expressing NKp30 in normal conditions, preferably selected from autologous PBMC and/or NK cells.

Inventors further herein describe a diagnostic method comprising the determination of the NCR3 mutational status and/or NKp30 isoforms status or profile of a subject who is a potential NK cells, stem cells or bone marrow donor subject and thus needs to have a normal expression or activity of NKp30 protein isoforms.

Such a diagnostic method may also be performed in a candidate for a NK cells, stem cells or bone marrow transplantation.

A kit for use in a method of assessing the sensitivity of a subject to a treatment of a cancer or the efficacy of a treatment of cancer in a subject, as defined previously, or for use in a method of assessing the prognosis of a cancer in a subject, is further herein provided. This kit comprises a nucleic acid probe, a primer and/or a ligand, such as an antibody, as described previously.

The kit may also comprise a container or support, reagents and/or a protocol for performing a hybridization, amplification or binding reaction, for example an antigen-antibody immune reaction.

The methods herein described may be performed in vivo, in vitro or ex vivo. They are preferably performed in vitro or ex vivo.

Screening Methods

The present application also provides novel methods for screening compounds or substances, preferably drug candidates or leads, useful for preventing or treating a cancer, in particular in a subject having a mutated NCR3 nucleic acid, an abnormal (relative) amount of at least one particular Natural Killer p30 (NKp30) RNA transcript isoform, and/or an abnormal expression or activity of at least one NKp30 protein isoform, comprising determining the ability of a test compound or substance to modulate the expression of NCR3 gene, and/or the expression or activity of a particular NKp30 protein isoform.

Preferred test compounds or substances screened using a method as described above are capable of restoring or enhancing a functional transcription of NCR3 gene and/or a functional expression or activity of at least one particular NKp30 protein isoform, in particular of at least one mutated or abnormal NKp30 protein isoform.

Compounds decreasing the NKp30 intermediate (INTER) protein isoform expression, and preferably further enhancing or increasing the NKp30 short (SHORT) and/or long (LONG) protein isoforms expressions are preferred. In other words, compounds favouring a normal or protective NKp30 isoforms profile wherein the relative expression of the NKp30 intermediate isoform is lower than the expression of the NKp30 short and/or long isoforms, are particularly preferred.

The screening methods herein disclosed preferably use NCR3 nucleic acid or NKp30 polypeptide or protein isoforms as well a molecules bypassing NKp30 signalling pathway and leading to DC maturation, as new targets. Such a maturation may be identified by an up-regulation of CD83, CD86 and HLADR. The methods include binding assays and/or functional assays, and may be performed in vitro, in cell systems, or in animals, etc.

The inventors in particular disclose a method of selecting a biologically active compound or substance, more particularly a compound or substance active in the prevention or treatment of cancer, said method comprising contacting in vitro a test compound or substance with a product selected from a NCR3 nucleic acid (gene or RNA for example), a NKp30 protein or polypeptide isoform, a molecule bypassing NKp30 signalling pathway and leading to DC maturation, and any fragment thereof, and determining the ability of said test compound or substance to bind said product.

In a further particular embodiment, the method comprises contacting a recombinant host cell expressing a NKp30 protein isoform according to the present invention or a molecule bypassing NKp30 signalling pathway and leading to DC maturation, with a test compound or substance, and determining the ability of said test compound or substance to bind respectively said NKp30 protein isoform or said molecule bypassing NKp30 signalling pathway and to modulate its activity.

In a particular embodiment, said NKp30 protein isoform can be an abnormal, preferably mutated, NKp30 protein isoform or a fragment thereof responsible of the NKp30 abnormal status or profile.

Binding to said nucleic acid, polypeptide or molecule provides an indication as to the ability of the test compound or substance to modulate the activity of said target, and thus to affect a pathway leading to a cancer in a subject.

The determination of binding may be performed by various techniques known from the man of the art, some of which were herein described previously, such as by labelling of the test compound or substance, by competition with a labelled control or reference ligand known or identified for binding to a particular NKp30 protein or polypeptide (wild-type or abnormal NKp30), such as a particular NKp30 isoform, or to particular NKp30 proteins or polypeptides, etc.

A further object herein described resides in a method of screening or selecting biologically active compounds or substances, more particularly compounds or substances active in the prevention or treatment of cancer, said method comprising contacting in vitro a test compound or substance with a herein described NCR3 gene, in particular a wild-type or mutated NCR3 gene, and determining the ability of said test compound or substance to modulate the expression of said NCR3 gene, in particular to modulate the alternative splicing thereof.

A biologically active compounds or substances may be a compound capable of restoring a functional transcription of NCR3 and/or a functional expression or activity of a particular NKp30 protein isoform.

It has been herein demonstrated by inventors (see experimental section) that trichostatin A (TSA) and 5-azacitidine (5AZA) in particular are able to modulate the wild-type NCR3 gene splicing in order to induce a significant (relative) over-representation of NKp30 INTER isoforms associated with an under-representation of NKp30 SHORT and LONG isoforms, compared to reference or mean representation values.

Inventors further herein discloses that antisense oligonucleotides[53] corresponding to SEQ ID NO: 49-51, used in combination, in particular are able to modulate the wild-type NCR3 gene splicing in order to induce a significant (relative) under-representation of NKp30 INTER isoforms associated with a relative over-representation of NKp30 SHORT and LONG isoforms, compared to reference or mean representation values.

Another method of selecting a biologically active compound or substance is further provided wherein said method comprises the steps of contacting in vitro a test compound or substance with a NKp30 protein isoform or with a molecule bypassing NKp30 signalling pathway and leading to DC maturation, and determining the ability of said test compound or substance to respectively modulate the activity of said NKp30 protein isoform or of said molecule bypassing the NKp30 signalling pathway.

A particular molecule bypassing NKp30 signalling pathway and leading to DC maturation usable in a method as presently disclosed may be selected from TLR3 ligands, such as double stranded RNA (for example Poly A:U and Poly I:C) and/or hypomethylated C and G enriched oligonucleotides (CpG oligonucleotides).

Another particular object of this invention resides in a method of screening or selecting compounds or substances active in the prevention or treatment of cancer, said method comprising contacting in vitro a test compound or substance with a polypeptide involved in the regulation of the activity of NKp30 such as IL-15, sushi IL-15Rα-IL-15 polypeptide, or binding site-containing fragment thereof and determining the ability of said test compound or substance to bind said polypeptide or fragment thereof.

In a further particular embodiment, the method comprises contacting a recombinant host cell expressing a polypeptide involved in the regulation of the activity of a NKp30 protein isoform with a test compound or substance, and determining the ability of said test compound or substance to bind said protein and to modulate the activity of said protein.

A further method herein disclosed comprises the steps of selecting biologically active compounds or substances, more particularly compounds or substance active in the prevention or treatment of cancer, said method comprising contacting in vitro a test compound or substance with a gene involved in the regulation of the activity of NKp30 and determining the ability of said test compound or substance to modulate the expression of said gene.

In a particular embodiment of the methods of screening, the modulation is an activation. In another particular embodiment of the methods of screening, the modulation is an inhibition.

The method of the present invention is suitable for screening many compounds or substances. These compounds or substances may be of various origin, nature and composition. A test compound or substance may be any organic or inorganic substance, such as a lipid, peptide, polypeptide, nucleic acid, small molecule, etc., in isolated or in mixture with other substances. The compounds or substances may be all or part of a combinatorial library of products, for instance.

In a particular embodiment, the present invention also discloses a method of screening or selecting a compound or substance useful for treating a cancer, preferably a compound or substance capable of restoring a functional expression of a mutated or abnormal NKp30 protein isoform and/or a functional transcription of NCR3 gene, said method comprising determining the ability of a test compound or substance to modulate, in particular to induce or increase, or on the contrary, to decrease, in vitro, in vivo or ex vivo the expression or activity of a particular NKp30 protein isoform or of a ligand thereof.

Inventors have demonstrated that ligands of particular NKp30 protein isoforms as well as molecules bypassing NKp30 signalling pathway, are able to increase the sensitivity of a subject to a cancer therapy as defined previously.

Preferred ligands may be used to upregulate a normal or protective NKp30 protein long and short isoforms profile expression relatively to the intermediate isoform profile expression and/or to increase the sensitivity of a subject to a cancer therapy as defined previously.

Preferred molecules bypassing NKp30 signalling pathway, herein identified, that may be used to upregulate a normal or protective NKp30 protein isoforms expression and/or to increase the sensitivity of a subject to a cancer therapy may be selected from NKp44, NKp46, NKG2D, an antibody directed against TRAIL on the NK cells, stem cells or bone marrow of a subject having a normal expression or activity of NKp30 protein isoforms.

The above screening methods may be performed in any suitable device, such as plates, for example multi-well plates, tubes, dishes, flasks, etc. Several test compounds or substances can be assayed in parallel.

Compositions and Uses

The use of a biologically active compound or substance, known or isolated with a screening method as previously described, capable of restoring or enhancing, i.e., increasing or favouring, a functional NKp30 protein isoform expression or activity, to prepare a pharmaceutical composition for treating or preventing a cancer in a subject, in particular a paediatric cancer, such as neuroblastoma, or a sarcoma, in particular a GIST, or a leukemia, in particular AML, is herein described.

The subject is preferably one having a mutated NCR3 nucleic acid, an abnormal (relative) amount of at least one particular Natural Killer p30 (NKp30) RNA transcript isoform, and/or an abnormal expression or activity of at least one particular NKp30 protein isoform, as explained previously.

It has been herein demonstrated by inventors that the functional NKp30 expression is typically associated to a normal or protective NKp30 isoforms status or profile wherein, in a subject, the relative amount of the NKp30 intermediate isoform is decreased and the relative expression of NKp30 short and/or long isoforms is increased when compared to reference or mean values.

In a particular embodiment, a normal or protective NKp30 isoforms status or profile is a profile wherein the (relative) amount of the NKp30 intermediate isoform is lower than the amount of the NKp30 short and/or long isoforms.

The substances obtained by the described screening method can also be used to prepare pharmaceutical compositions to enhance the sensitivity of a subject (as defined previously) to a cancer therapy as defined previously.

The compound or substance can be a known compound or substance or a compound or substance selected using a screening method according to the invention.

Examples of compounds herein usable to prepare a pharmaceutical composition for treating or preventing a cancer in a subject, can further be selected from the group consisting of a NKp30 RNA transcript isoform encoding a functional NKp30 protein isoform, a functional NKp30 protein isoform, a nucleic acid encoding a functional NKp30 protein isoform, a vector comprising such a nucleic acid or a recombinant host cell comprising such a vector or nucleic acid.

A compound or substance capable of restoring a functional NKp30 RNA transcription or a functional expression or activity of NKp30 protein isoforms may further be used to prepare a pharmaceutical composition for treating or preventing a cancer in a subject as defined previously.

Such a compound may be selected in the group consisting of histone deacetylase (HDAC) inhibitors such as valproic acid (VPA), suberoylanilide hydroxamic acid (SAHA), trichostatin A (TSA), sodium butyrate, MS-275, aclarubicin, sodium vanadate; DNA methyltransferases inhibitors such as 5-azacitidine, 5-aza-2'-deoxycytidine (decitabine); PKC inhibitors, such as Gö6983; imatinib mesylate (STI571); cytokinin kinetin; cycloheximide; dexamethasone; sodium oleate; estrogen; progesterone; oncostatin M (OSM); FK506; cyclosporin-A; staurosporine and any combination thereof.

Antisense oligonucleotides corresponding to SEQ ID NO: 49-51, are also examples of compounds usable, in combination, to prepare a pharmaceutical composition for treating or preventing a cancer in a subject as defined previously.

The NK cells, bone marrow and stem cells of a subject having a normal NKp30 protein expression or activity of NKp30 protein isoforms are examples of substances which can be used to prevent or treat a cancer in such a subject.

The use of a biologically active compound or substance bypassing NKp30 signalling pathway and leading to dendritic cell (DC) maturation to prepare a pharmaceutical composition for treating or preventing a cancer in a subject as defined previously, is herein disclosed.

Such a compound is preferably selected in the group consisting of IFNγ, TNFα and combination thereof.

The use of a biologically active compound or substance bypassing NKp30 signalling pathway and leading to natural killer (NK) cell activation to prepare a pharmaceutical composition for treating or preventing a cancer in a subject as defined previously, is further herein disclosed.

Such a compound is preferably selected in the group consisting of NKp44, NKp46, CD16 (FcγRIIIA), NKG2D and a TLR3 ligand.

TLR3 ligands is preferably a double stranded RNA which may be selected from Poly A:U and Polyl:C for example.

Inventors further herein provide a pharmaceutical composition comprising at least one of the above described compound or product known or selected with a method according to the present invention, and capable of restoring or enhancing the expression of a functional NKp30 protein isoform.

The pharmaceutical compositions herein provided may further advantageously comprise at least one compound or substance selected from a tyrosine kinase inhibitor (TKI), such as imatinib mesylate (STI571) and/or sunitinib malate (SU11248); a farnesyl-transferase inhibito (FTI) and an anthracycline, such as DOX, oxali-platinum and/or cis-platinum (PLAT), as a combined preparation, for simultaneous, separate or sequential use, in the prevention or treatment of said cancer.

A particular composition herein described comprises a tyrosine kinase inhibitor (TKI), a PKC inhibitor and/or a farnesyl-transferase inhibitor, alone or as combined preparation, for simultaneous, separate or sequential use in the prevention or treatment of said cancer.

Pharmaceutical compositions herein disclosed further comprise a pharmaceutically acceptable carrier or vehicle.

In a preferred embodiment, pharmaceutical compositions herein described, in particular pharmaceutical compositions which do not comprise a chemotherapeutic product, are administered before any treatment comprising the administration of a chemotherapy or radiotherapy, in NKp30 mutated individuals. The administration of the pharmaceutical composition(s) may be performed in a single administration or in repeated administrations, before and/or during any subsequent treatment, for example one day before any subsequent treatment and every 3 weeks during said treatment.

The pharmaceutical compositions, comprising a TLR3 ligand, are preferably administered before and/or pending any chemotherapy or radiotherapy.

The administration of the pharmaceutical compositions herein provided may be performed by any method known to those skilled in the art, preferably by the oral route or by injection (preferably via systemic route). The administered doses may be adapted by those skilled in the art.

Typically, in terms of treatments, administration doses may be for example:

for 4-Epirubicine (anthracycline): 100 mg/m$^2$ every 3 weeks;

for Oxaliplatinum: around 600-1000 mg/m² every 3 weeks;

for nucleic acid compounds, doses may range for example for Poly A:U from 30-50 mg/week, during 6 weeks.

In the context of a prophylactic treatment, pharmaceutical compositions according to the invention are preferably administered every 3 weeks.

It is understood that repeated treatments may be performed, possibly in combination with other active agents, therapy or any pharmaceutically acceptable vehicle (eg., buffers, isotonic saline solutions, in the presence of stabilisers, etc.).

The invention also resides in method of treating or preventing a cancer in a subject through activation of a functional expression or activity of at least one NKp30 protein isoform.

More particularly, methods of treating a subject who carry mutated alleles of the NCR3 gene, express an abnormal NKp30 protein isoform or exhibit an abnormal NKp30 protein isoform activity, including combined therapy are herein provided.

Subjects may thus be treated for example through gene therapy, protein replacement therapy or through the administration of NKp30 protein isoform mimetics and/or activators of a normal or protective NKp30 protein isoforms status or profile wherein the relative expression of the NKp30 intermediate isoform is lower than the (relative) expression of the NKp30 short and/or long isoforms. At least one of said methods may further be combined to a cancer therapy as defined previously.

The invention also resides in method of treating or preventing cancer in a subject through activation of a functional expression or activity of at least one NKp30 protein isoform using a product as herein described previously.

Diagnostic methods, as herein described, aimed at assessing the sensitivity of a subject to a treatment of cancer or at detecting innate or acquired NKp30 qualitative or quantitative deficiencies in cancer patients may be applied to a subject selectable for such a treatment, in particular to a subject who is a candidate for or will undergo a cancer treatment, in particular a chemotherapeutic treatment, and/or an allogeneic bone marrow transplantation. Concerning the subject who is a candidate for or who will undergo an allogeneic bone marrow transplantation, it is preferable to select an appropriate bone marrow donor subject regarding the NKp30 isoforms expression status or profile. An appropriate bone marrow donor subject is indeed a subject having a functional or normal expression or activity of NKp30 protein isoforms as herein defined.

Other characteristics and advantages of the invention are given in the following experimental section (with reference to FIGS. 1 to 24), which should be regarded as illustrative and not limiting the scope of the present application.

EXPERIMENTAL SECTION

A. Preliminary Assay (Cohort of 41 Patients/37 Healthy Volunteers)

Inventors herein demonstrate that a deficiency in the transcriptional regulation of NCR3 gene (quantitative and qualitative modulation of the expression of NKp30 isoforms at the NK cell surface) affect the control of tumoral growth via diminution of the DC activation by NK cells through NKp30 and production of IFNγ, necessary for the establishment of a long term T cells dependent anti-tumoral response[41].

Inventors have first genotyped 21 single nucleotide polymorphisms (SNPs) distributed in NCR3 gene in 41 GIST patients and 37 healthy volunteers. The preliminary results revealed that two mutations in NCR3 gene are associated with the control of GISTs.

Materials and Methods

Patients and Healthy Volunteers (HV).

The cohort was first composed of 41 GIST patients treated by TKI (tyrosine kinase inhibitors) therapies and followed in Institut Gustave Roussy (IGR). GIST patients were enrolled in the EORTC Phase III trial 62005 or in the French Sarcoma Group (IGR and CLB mostly) Phase III clinical trial (BFR14), assessing dose and duration of Imatinib mesylate (IM) respectively. BRF14 was an open-label, multicentric trial randomizing treatment interruption versus maintenance after 3 years (actually 1 year initially) in patients with metastatic or unresectable malignant GIST in relapse[54]. EORTC 62005 trial was a randomized study comparing 400 vs 800 mg daily of IM in GIST patients[55].

An informed written consent was obtained from patients according to the local ethical committee for the clinical and the immunological studies (Comite Consultatif de Protection des Personnes se prêtant à la Recherche Biomédicale, Kremlin-Bicêtre). Heparinized blood was drawn from patients after 2, 6, 12 months of imatinib mesylate (IM) therapy. About 37 healthy volunteers were used as controls for the immunological parameters.

Patients' characteristics including age, sex, lymphocytes and NK cell counts, dose and duration of therapy with IM have been described (Menard et al.[42]).

Tumor response was assessed by computed tomography (CT) scan and the response was classified according to the RECIST criteria every 3 months after the beginning of treatment. Non progressive disease encompassed stable disease and objective partial or complete responses. Median follow up of the patients was 47 months (range 6-75 months).

The preliminary cohort of 19 neuroblastoma patients managed at IGR, Center Léon Bérard and surrounding anticancer centers, was composed of metastatic and localized tumors. The classification of patients with good or bad clinical prognostic was based on stage of disease, age, and amplification of the MYCN oncogene[12].

RNA Extraction and RT-PCR.

Total cellular RNA was isolated from PBMC and NK cell lines with the RNeasy kit (Qiagen). First strand cDNA was synthesized from 5 μg of total RNA using SuperScript™ II Reverse Transcriptase and random primers (Promega) according to Invitrogen's instructions.

For the "GIST patients and Healthy Volunteers" cohort, real time quantitative PCR amplifications were conducted using FastStart DNA Master SYBRGreen I Mix according to the manufacturer's instructions, with 0.3 μM primers, 2 mM MgCl2 and cDNAs, in a 20 μl final reaction volume. Thermocycling was performed using a LightCycler (Roche Molecular System) initiated by 10 min incubation at 95° C., followed by 38 cycles (95° C., 1 s; 65° C., 10 s; 72° C., 20 s). NKp30 mRNA expression level was normalized by dividing its relative mRNA amount with the corresponding GAPDH mRNA amount.

The specific primers used in the real time quantitative PCR were designed with Primer3 (v.0.4.0) software (http://frodo.wi.mit.edu/).

The following primers were used: NKp30Fex2: 5'-GTGAGGAATGGAACCCCAGAGT-3' (SEQ ID NO: 20); NKp30Fex2del: 5'-GTGGTTCCAGGGAAGGAGGC-3' (SEQ ID NO: 21); NKp30Rex4I: 5'-TTCCCATGTGACA- GTGGCATT-3' (SEQ ID NO: 22 or 27); NKp30Rex4II: 5'-CCGGAGAGAGTAGATTTGGCATATT-3' (SEQ ID NO: 23); NKp30Rex4III: 5'-TGGACCTTTCCAGGTCAGACATT-3' (SEQ ID NO: 24).

The primer pairs "NKp30Fex2/NKp30Rex4II" were used to amplify the NKP30 SHORT-WT transcripts; "NKp30Fex2del/NKp30Rex4II" for SHORT-DEL transcripts; "NKp30Fex2/NKp30Rex4I" for INTER-WT transcripts; "NKp30Fex2del/NKp30Rex4I" for INTER-DEL transcripts; "NKp30Fex2/NKp30Rex4III" for LONG-WT transcripts; "NKp30Fex2del/NKp30Rex4III" for LONG-DEL transcripts.

As explained below in part. B, inventors later discovered that primer pairs (above identified) which have been used, although NKp30 specific, were only able to discriminate between LONG, SHORT and INTERMEDIATE isoforms (i.e., NKp30 isoforms distinguished according to their respective intra-cellular domains) but not between constant ("DEL") and variable ("WT") isoforms (i.e., NKp30 isoforms distinguished according to their respective extra-cellular domains). As will be apparent, the above results allow the identification of the NKp30 intermediate isoform as the key isoform for assessing, in particular, the prognostic of a cancer in a subject. The above described study (part A) has however been completed by inventors in a second time (part B), on a cohort doubling the patients number and confirming the strategic value of said NKp30 intermediate isoform. The added described results using the TaqMan method are however more specific, as will be explained below in part B.

For the neuroblastoma cohort, a more sensible quantification system was used. The PCR primers and TaqMan probes for the six NKP30 transcripts and the β2M housekeeping transcript were designed with the Primer Express software v1.0 (Applied Biosystems). The following primers and probes were used: NKP30 EC-WT: 5'-TTTCCTCCATGACCACCAGG-3' (SEQ ID NO: 25); NKP30 EC-DEL: 5'-GGTTCCAGGGAAGGAGGCT-3' (SEQ ID NO: 26); NKP30 EX4I: 5'-TTCCCATGTGACAGTGGCATT-3' (SEQ ID NO: 27 or 22); NKP30EX4I: 5'-CGGAGAGAGTAGATTTGGCATATT-3' (SEQ ID NO: 28); NKP30EX4I: 5'-GGACCTTTCCAGGTCAGACATT-3' (SEQ ID NO: 29); NKP30Probe (6-FAM/TAMRA): 5'-AGCTGCACATCCGGGACGTGC-3' (SEQ ID NO: 30); B2MFor: 5' GATGAGTATGCCTGCCGTGT 3' (SEQ ID NO: 31); B2MRev: 5' AATTCATCCAATCCAAATGCG 3' (SEQ ID NO: 32); B2MProbe (6-FAM/TAMRA): 5' AACCATGTGACTTTGTCACAGCCCAA 3' (SEQ ID NO: 33).

One microliters of first-strand cDNA was mixed with 12.5 µL of 2× TaqMan Universal PCR Master Mix (Applied Biosystems) and 0.75 µL of NKP30 primers (10 µM) and probe (5 µM) or 0.5 µL of β2M primers (10 µM) and probe (5 µM) in a final volume of 25 µL. Temperature cycling and real time fluorescence measurement were done using an ABI prism 7700 Sequence Detection System (Applied Biosystems). The PCR conditions were as follows: initial incubation at 50° C. for 2 min, denaturation at 95° C. for 10 min, followed by 45 cycles at 95° C. for 15 s, and 60° C. (for NKP30 SHORT-, INTER- and LONG-WT, and β2M transcripts) or 62° C. (for NKP30 SHORT-, INTER- and LONG-DEL transcripts) for 1 min. The real time PCR (RT-PCR) data were analyzed using the $2^{-\Delta\Delta C_T}$ method, according to the manufacturer's directions.

It is to note that inventors have further produced another NKP30Probe (6-FAM/TAMRA) allowing the signal revelation, said probe being more specific than the one corresponding to the above described SEQ ID NO: 30, i.e., able to discriminate between potential DNA contaminants and cDNA in the context of the above described applied RT-PCR method. Said new probe, herein identified as SEQ ID NO: 48, has been used on the enlarged cohort as will be apparent from the below experimental part description (part B).

Cloning.

The synthesized first-strand NK92 cDNA was amplified by PCR with the HotStarTAQ DNA polymerase (Qiagen) in 50 µl reactions, using a Hybaid apparatus.

HPLC-purified primers used for the cloning system were designed with Primer3 v0.4.0 software, for SHORT-WT and SHORT-DEL: KPNI-NKp30 5'-GG<u>GGTACC</u>CCGACATGGCCTGGATGCTGTT-3' (SEQ ID NO: 34) and EcoRI-SHORT 5'-G<u>GAATTC</u>CTGGTGGAAGGGAAAGTTCAG-3' (SEQ ID NO: 35); for INTER-WT and INTER-DEL: KPNI-NKp30 and EcoRI-INTER 5'-G<u>GAATTC</u>CTTTTGAAGAGGACTAGGGACATC-3' (SEQ ID NO: 36); for LONG-WT and LONG-DEL: KPNI-NKp30 and EcoRI-LONG 5'-G<u>GAATTC</u>CATTTCTCAGGACAATCAGG-3' (SEQ ID NO: 37).

Underlined sequences are restriction enzyme recognition sites for the DNA cloning in expression plasmid vectors. Thermocycling started with a single denaturation step for 15 min at 95° C., following 30 cycles of denaturation for 40 sec at 95° C., annealing for 30 sec at 67° C. for SHORT, INTER and LONG primers, and extension at 72° C. for 1 min. One final extension step was added for 10 min at 72° C. PCR products were isolated on agarose gel, purified using the QIAquick Gel Extraction kit (Qiagen), and digested with restriction enzymes, KpnI and EcoRI (Ozyme). The digested fragments were ligated to pcDNA3.1 mammalian expression vector (Invitrogen) and later also to pIRES2 mammalian bicistronic expression vector (CLONTECH). The nucleotide sequences were analyzed by ABI PRISM 310 genetic analyzer (Applied Biosystems).

Genotyping.

DNA was extracted from peripheral blood mononuclear cells (PBMC) separated by Ficoll-Hypaque density gradient. To identify NCR3 mutations, inventors performed sequencing analysis of three defined PCR products.

Three primer pairs were designed with the PRIMER3 program (NCR3Frag1: 5'-GATGGGTCTGGGTACTGGTG-3' (SEQ ID NO: 14) and 5'-GGGATCTGAGCAGTGAGGTC-3' (SEQ ID NO: 15); NCR3Frag2: 5'-ATCCTGTGCTCTCTGGGTGT-3' (SEQ ID NO: 16) and 5'-CTGTACCAGCCCCTAGCTGA-3' (SEQ ID NO: 17); NCR3Frag3: 5'-CTGAACTTTCCCTTCCACCA-3' (SEQ ID NO: 18) and 5'-GGTCCAGCCAGTAAAAACCA-3' (SEQ ID NO: 19).

PCR amplification was carried out with AmpliTaq (PE Biosystems) in 50 µl reactions, using a Hybaid apparatus. Thermocycling started with a single denaturation step for 5 min at 95° C., following 40 cycles of denaturation for 40 sec at 95° C., annealing for 30 sec (64° C. for NCR3Frag1 primers, 60° C. for NCR3Frag2 primers, and 64° C. for NCR3Frag3 primers) and extension at 72° C. for 10 sec. One final extension step was added for 10 min at 72° C. Before starting the sequencing reaction, the PCR products were purified with the QIAquick PCR purification kit (Qiagen) and quantified by 2% agarose gel electrophoresis. Sequencing reaction was performed with the CEQ 8000 kit and a CEQ 8000 automated fluorescent sequencer (Beckman Coulter).

Clustering Analysis.

Unsupervised hierarchical clustering investigated was applied to data log-transformed and median-centred using the Cluster and TreeView programs (average linkage clustering using Pearson's correlation as similarity metric)[56].

Modulation of NCR3 Alternative Splicing by HDAC and Demethylating Agents.

NK92 cells were seeded ($5.10^5$ NK/well) in 96 wells plates and incubated with 5-azacitidine (2 µM) and IL-2 (50 UI/ml) for 36 h at 37° C.

YTS cells were seeded ($5.10^5$ NK/well) in 96 wells plates and incubated with trichostatine A (100 nM) for 45 h at 37° C.

NK Cell Flow Cytometry Analyses.

NK cells were stained with the following antibodies: CD3-APC (clone UCHT) purchased from BD Pharmingen; NKp30-PE (clone AF29-4D12) from Miltenyi, CD56-PC5 (clone N901), from Beckman-Coulter. Fluorescence was acquired on a FACScalibur cytometer and subsequently analyzed with the CellQuest Pro software.

Assessment of In Vitro NK Cell Effector Functions.

For NKp30 cross-linking experiments, NK cells were purified (purity>95%) with the human NK cells Easy Sep kit (Stem Cell Technologies, Paris, France) and seeded ($2.10^5$ NK/well) in 96 wells-Maxisorp plates (Nunc, Roskilde, Denmark) coated with 2.5 µg/ml of mouse IgG2a anti-NKp30 (clone 210847, R&D Systems, Lille, France) or isotype control for 7 hours. After a 20 hr- NKp30 cross-linking, supernatants were harvested, stored at −80° C., and then assessed for their IFN-γ concentration using commercial ELISA kits following manufacturer's instructions (BD Biosciences/Pharmingen, Le Pont de Claix, France). Alternatively, NK cells were incubated for 7 hrs with 2 µl of anti-CD107a-PE (clone H4A3, Pharmingen) in AIMV supplemented with 10 µM monensin and CD3/CD56 staining was performed at the end of the cross-linking.

Statistical Analyses.

The non parametric Mann-Whitney test was used for comparison of the different groups. Results were considered as significant at 95% confidence when $p<0.05$. All the statistical analyses were performed with the GraphPad Prism software version 5.

Specific Aims of the Preliminary Study

Aim 1: Prevalence and Predictive Value of NKp30 Isoforms in Response to Treatment in GIST Patients.

A series of >40 gastrointestinal sarcoma (GIST)-bearing patients treated with imatinib mesylate and >30 age and sex-matched healthy volunteers (HV) were examined for their transcriptional pattern of expression of each of the individual NKp30 isoforms.

In parallel, the NKp30 expression levels and functions (degranulation and IFNγ/TNFα production upon cross-linking with anti-NKp30 antibodies) on purified peripheral blood mononuclear cells (PBMC) have been assayed.

Correlations between the mRNA profiling, protein expression and function of NKp30 were examined among i) HV and GIST patients, ii) between progressors and non progressors in patients treated with imatinib mesylate.

Aim 2: Prognostic Value of NKp30 Isoforms in Neuroblastoma Patients.

Certain human malignancies (such as neuroblastoma) may be controlled by NK cells. Based on this assumption, inventors have investigate whether the protective pattern of NKp30 mRNA expression validated in GIST patients also apply for other malignancies treated with conventional treatments. A preliminary cohort of 19 neuroblastoma patients was studied (profiling of NKp30 mRNA in PBMC cells in patients with a good clinical prognostic versus patients with a bad clinical prognostic).

Aim 3: Pharmacological Modulations of the NKp30 Isoforms.

Epigenetic regulations allow for modulations of alternative splicing. Using histone deacetylase (HDAC) and DNA methyltransferase inhibitors, inventors have studied potential alterations in the various proportions of each individual NKp30 splicing variant in vitro on NK cell lines with defined patterns.

Results

1. Prevalence and Predictive Value of NKp30 Isoforms in Response to Treatment in GIST Patients.

Figure 1:
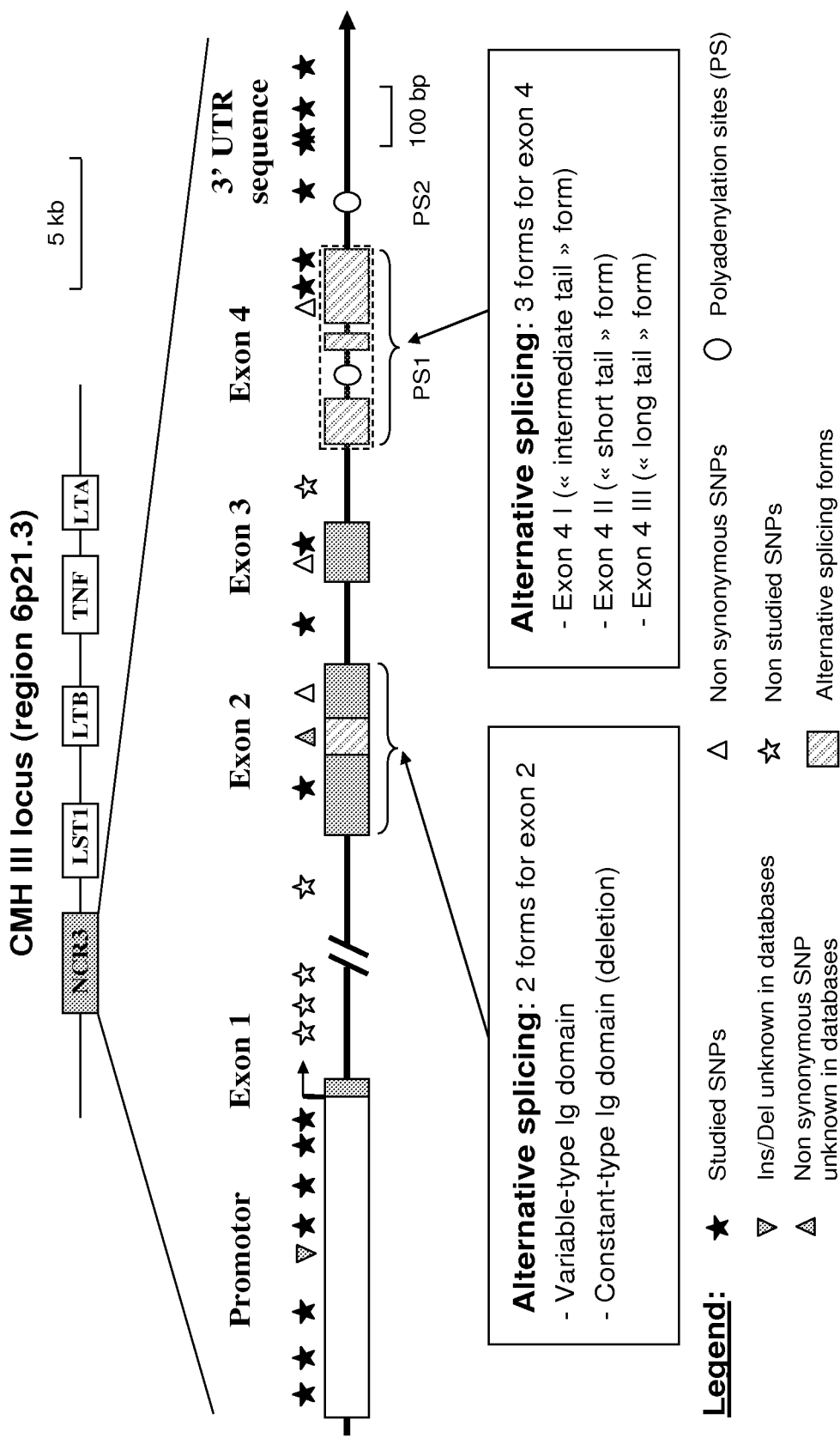
FIG. 1. Localization and structure of NCR3 gene

According to the available databases, the human NCR3 gene is expressed as six differentially spliced transcripts: two types of extracellular domains exist (a variable Ig-like domain and a constant Ig-like domain), each of them being linked to one of the three distinct intracellular domains (short, intermediate and long tail)[24] (FIG. 1).

To investigate the clinical and functional relevance of the six NKp30 isoforms, inventors first analyzed the NKp30 transcriptional profile of 41 GIST patients (all treated with imatinib mesylate—standard care—for at least 2 months) and 37 HV.

Specific primers were designed for each NKp30 isoforms in order to quantify the 6 transcripts using RT-PCR method (SHORT-WT: variable Ig-like domain/short tail; INTER-WT: variable Ig-like domain/intermediate tail; LONG-WT: variable Ig-like domain/long tail; SHORT-DEL: constant Ig-like domain/short tail; INTER-DEL: constant Ig-like domain/intermediate tail; LONG-DEL: constant Ig-like domain/long tail) (FIG. 2). As explained above, it appeared, in a second time, that said above described primers, used in the SYBRGreen assay, were in fact specific for the three distinct intra-cellular domains but not able to discriminate between the variable and constant extra-cellular domains isoforms. The below added results confirm the relevance of the first used primers to discriminate between LONG, SHORT and INTERMEDIATE isoforms. Inventors in addition discovered that the first used antibodies, although NKp30 specific, were not surely able to identify constant domains isoforms but were surely able to detect variable extra-cellular domains isoforms. The below added results are now more relevant because they were obtained while using the above described primers identified by SEQ ID NO: 25, 27 (or 22), 28, 29, 31, 32, 33 and 48, which are able to specifically identify the SHORT, LONG and INTERMEDIATE variable extra-cellular domain ("WT") isoforms. As they were used on very important (doubled) patients cohort, they are now usable to control the exact relative amounts of each isoform in order to assess, in particular, the prognosis of a cancer in a subject.

The expression of the NKp30 isoforms was assessed from the cDNA of PBMC. The comparison of the proportions of the six NKp30 isoforms in GIST patients and HV revealed on the first cohort of 41 patients an over-representation of the SHORT-DEL isoform associated with an under-representation of the INTER-DEL isoform in GIST patients (FIG. 3A).

By considering the intracellular domain [sum of WT (variable Ig-like domain) variants and DEL (constant Ig-like domain) variants for the three SHORT-, INTER- and LONG-intracellular domains], the GIST patient profile was first mainly characterized by an over-representation of SHORT isoforms and an under-representation of INTER isoforms compared with HV (FIG. 3B).

The NKp30 transcriptional profile stability in four GIST patients during the course of treatment was controlled (FIG. 4). The majority of patients displayed a stable NKP30 profile.

Using a hierarchical clustering approach based on the six NKP30 isoforms, inventors first segregated the patients' cohort in 2 groups (FIG. 5). Patients in group B exhibited an accelerated time to progression (35% relapse at 45 months). In contrast, only 16% of patients in group A did relapse at 45 months of imatinib mesylate. Interestingly, 50% of HV were segregated in the unfavourable group B.

Inventors characterized the NKP30 transcriptional profiles associated to groups A and B (FIG. 6): the group A was characterized, in this specific example, by a INTER$^{High}$/SHORT$^{Low}$/LONG$^{Low}$ profile (called "profile A"), and the group B was characterized by a INTER$^{Low}$/SHORT$^{High}$/LONG$^{High}$ profile (called "profile B"), as well for GIST patients (FIG. 6A-B) as for healthy volunteers (FIG. 6C-D).

2. Functional Relevance of the Transcriptional Profiles of NKp30 Isoforms in GIST Patients and HV.

The comparison of the NKp30 cell surface expression in FACS analyses on NK cells purified from HV and GIST patients displaying the profile A versus profile B did not reveal significant differences (FIG. 7). Interestingly, the functional characterization of these two profiles revealed an association between the INTER$^{Low}$/SHORT$^{High}$/LONG$^{High}$ profile B and a low production of IFNγ by NK cell upon NKp30 cross-linking in vitro (on purified NK cells) (FIG. 8).

No association was detected between the cytotoxic functions of these NK cells and the NKp30 profiles (data not shown).

3. Association Between NCR3 Mutations and the Transcriptional Profiles of NKp30 Isoforms in GIST Patients and HV.

The NKp30 INTER$^{Low}$/SHORT$^{High}$/LONG$^{High}$ transcriptional profile of group B is associated with the non synonymous NCR3*3571 G/T (R174S-rs3179003) mutation (13% of mutated individuals in group B versus 0% in group A).

The NKp30 INTER$^{High}$/SHORT$^{Low}$/LONG$^{Low}$ profile of group A is associated with the NCR3*3790 T/C (rs986475) mutation localised in the 3' untranslated region of NCR3 gene (58% of mutated individuals in group A versus 3% in group B) (FIG. 9). Interestingly, the NCR3*3790 C mutation disrupts a site of polyadenylation in NCR3 gene (FIG. 10). The consequences in NCR3*3790 CC patients are an exclusive transcription of INTER isoforms (data not shown).

4. Prognostic Value of NKp30 Isoforms in Neuroblastoma Patients.

To investigate the clinical relevance of the six NKp30 isoforms in neuroblastoma, inventors analyzed the NKp30 transcriptional profile of 19 patients at diagnostic with a good or bad clinical prognostic.

The expression of the NKp30 isoforms was assessed from the cDNA of PBMC.

The comparison of the proportions of the six NKp30 isoforms in neuroblastoma patients revealed a trend of an over-representation of the SHORT and LONG isoforms associated with an under-representation of the INTER isoforms in neuroblastoma patients with a bad prognostic compared to neuroblastoma patients with a good prognostic (FIG. 11).

Using a hierarchical clustering approach based on the six NKP30 isoforms, inventors segregated the patients' cohort in 2 groups (FIG. 12). Five of seven patients with a good clinical prognostic were segregated in the group 2 characterized by the NKp30 INTER$^{High}$/SHORT$^{Low}$/LONG$^{Low}$ profile (FIG. 13). In this specific example, the protective pattern of NKp30 mRNA expression validated in non-progressor GIST patients (profile A) appeared to apply for neuroblastoma patients with a good clinical prognostic.

5. Modulation of the Alternative Splicing of NCR3 Gene with Drugs.

Several approaches modulating alternative splicing may be used to operate a switch from NKp30 INTER$^{Low}$/SHORT$^{High}$/LONG$^{High}$ (identified as profile B following the first results obtained in the present study (part A.)) towards NKp30 INTER$^{High}$/SHORT$^{Low}$/LONG$^{Low}$ (identified as profile A following the first results obtained in the present study (part A.)). Inventors have tested several families of drugs belonging to the histone deacetylase (HDAC) and DNA methyltransferase inhibitors.

The YTS and NK92 NK cell lines were used as model since both exhibit a NKp30 INTER$^{Low}$/SHORT$^{High}$/LONG$^{High}$ (identified as profile B in part A).

Preliminary results indicated that the trichostatin A (TSA) and the 5-azacitidine (5AZA) could induce a significant over-representation of INTER isoforms associated with an under-representation of SHORT and LONG isoforms in YTS and NK92 cell lines, respectively (FIG. 14).

B. Additional Study (Cohort of 80 Patients/56 Healthy Volunteers)

Material and Methods

Cloning of Spliceoforms in Expression Vectors and Transfections.

The synthesized first-strand NK92 cDNA was amplified by PCR with the HotStarTAQ DNA polymerase (Qiagen) in 50 μl reactions, using a Hybaid apparatus. HPLC-purified primers used for the cloning system were designed with Primer3 v0.4.0 software (http://frodo.wi.mit.edu/), for NKp30b: KPNI-N Kp30 5'-GG<u>GGTACC</u>CCGACA TGGC-CTGGATGCTGTT-3' (SEQ ID NO: 34) and EcoRI-NKp30b 5'-GG<u>AATTC</u>CTGGTGGAAGGGAAA GTTCAG-3' (SEQ ID NO: 35); for NKp30c: KPNI-NKp30 and EcoRI-NKp30c 5'-GG<u>AATTC</u>CTTTTGAA GAG-GACTAGGGACATC-3' (SEQ ID NO: 36); for NKp30a: KPNI-NKp30 and EcoRI-NKp30a 5'-G G<u>AATTC</u>CATTTCTCAGGACAATCAGG-3' (SEQ ID NO: 37). Underlined sequences are restriction enzyme recognition sites for the DNA cloning in expression plasmid vectors.

Thermocycling started with a single denaturation step for 15 min at 95° C., following 30 cycles of denaturation for 40 sec at 95° C., annealing for 30 sec at 67° C. for NKp30a, b and c primers, and extension at 72° C. for 1 min. One final extension step was added for 10 min at 72° C. PCR products were isolated on agarose gel, purified using the QIAquick Gel Extraction kit (Qiagen), and digested with restriction enzymes, KpnI and EcoRI (Ozyme).

The digested fragments were ligated to pIRES bicistronic mammalian expression vector (Clontech). The nucleotide sequences were analyzed by ABI PRISM 310 genetic analyzer (Applied Biosystems).

Functional Studies Using the NKL Clones.

DC/NK cross talks. 0.5×10$^5$ immature monocyte-derived DC cultured in GM-CSF+IL-4 as previously described[17] were admixed at a 1:3 ratio with 1.5×10$^5$ NKL clones expressing either NKp30a (LONG), b (SHORT), or c (INTERMEDIATE) isoform for 24 hrs. Supernatants were harvested to monitor the cytokine levels using commercial ELISA (human IFNγ, human TNFα kits (BD Biosciences/Pharmingen, Le Pont de Claix, France). Tumor/NK mixed cultures. 10$^5$ HEK 293 (kindly provided by E. Vivier, CIML, Marseille, France) or GIST 882 (kindly provided by J. A. Fletcher, Harvard Medical School, Boston, Mass.) or Mel 888 were admixed at a 1:1 E:T ratio with 10$^5$ NKL clones expressing either NKp30a (LONG), b (SHORT), or c (IN- TERMEDIATE) isoform for 24 hrs. Supernatants were harvested to monitor the cytokine levels using commercial ELISA (as stated above). Cross-linking NKp30 and measuring degranulation and cytokine production. See description below.

Cohorts of Patients and Normal Volunteers.

The immunomonitoring studies of NK cell responses prospectively examined GIST patients enrolled onto the EORTC Phase III trial 62005 and GIST patients included in the French Sarcoma Group Phase III clinical trial (BFR14), assessing dose and duration of IM respectively (n=80). An informed written consent was obtained from patients according to the local ethical committee for the clinical and the immunological studies. Heparinized blood was drawn from patients during treatment (between 2-94 months of IM therapy, mean=28±3 months). Patients' characteristics are depicted in Table 1.

TABLE 1

Characteristics of patients in NKp30 profile A and B groups

|  | Profile A (n = 44) | Profile B (n = 36) | P value |
|---|---|---|---|
| Gender (male/female) | 22/22 | 17/19 | NS[a] |
| Age | 56 ± 13 | 59 ± 13 | NS[b] |
| Primary tumor site |  |  | NS[a] |
| Stomach | 45% | 42% |  |
| Small bowel | 34% | 41% |  |
| Others | 21% | 17% |  |
| Metastatic site(s) |  |  | NS[a] |
| Liver | 58% | 44% |  |
| Peritoneum | 27% | 34% |  |
| Both | 15% | 22% |  |
| c-kit mutation[c] |  |  | NS[a] |
| Exon 11 | 55% | 53% |  |
| Exon 9 | 5% | 3% |  |
| Wild-type | 13% | 5% |  |
| Not done | 27% | 39% |  |
| Response to IM |  |  | NS[a] |
| Objective response | 59% | 72% |  |
| Stable disease | 35% | 25% |  |
| Non evaluable | 6% | 3% |  |
| Follow up (months) | 52 ± 26 | 49 ± 22 | NS[a] |

[a]Chi-square test,
[b]Mann Withney test,
[c]Assessed as reported in Emile, et al.[52],
NS: non significant Tumor response was assessed by computed tomography (CT) scan and the response was classified according to the RECIST criteria every 3 months after the beginning of treatment.

Non progressive disease encompassed stable disease and partial or complete responses. N=56 healthy volunteers (sex and age-matched with GIST patients) were used as controls for the immunological parameters.

Cohort of AML Patients.

Two hundred and eighteen patients aged 45 years (±12.6) with de novo AML according to standard FAB[57] and WHO criteria[58], available FLT3 mutational status were analyzed. The mutational status of the tumors was determined as previously described[51]. All were treated by induction chemotherapy combining daunorubicin or idarubicin and ara-cytin. Patients under 60 years (n=193) were allocated to autologous Stem Cell Transplantation (ASCT) or intensive chemotherapy with high-dose aracytin, others (n=25) to chemotherapy with intermediate-dose aracytin.

Assessment of NKp30-Dependent Cytokine Secretion and Degranulation on Bulk NK Cells.

PBMC of GISTs patients and HV were obtained by Ficoll-Hypaque (Amersham Pharmacia, Orsay, France) density cushion centrifugation. For NKp30 cross-linking experiments, NK cells were purified (purity >95%) with the human NK cells Easy Sep kit (Stem Cell Technologies, Paris, France) and seeded ($10^5$ NK/well) in 96 wells-Maxisorp plates (Nunc, Roskilde, Denmark) coated with 2.5 µg/ml of mouse IgG2a anti-NKp30 (clone 210847, R&D Systems, Lille, France) or isotype control for 7 hours. Otherwise, NK cells were activated with 1000 IU of rIL-2 (Chiron, USA) for 40 hrs. Then, supernatants of NK cells were assessed for their TNFa levels using commercial ELISA kits (BD Biosciences/Pharmingen, Le Pont de Claix, France). Degranulation was assessed by flow cytometry as previously described[17]. Briefly, NK cells were incubated for 7 hrs with 2 µl of anti-CD107a-PE (clone H-4A3, Pharmingen) in AIMV supplemented with 10 µM monensin and CD3/CD56 staining was performed at the end of the cross-linking.

RT-PCR of the Isoforms and Non Hierarchical Clustering.

Total cellular RNA was isolated from PBMC and NK cell lines with the RNeasy kit (Qiagen). First strand cDNA was synthesized from 5 µg of total RNA using SuperScript™ II Reverse Transcriptase and random primers (Promega) according to Invitrogen's instructions. The PCR primers and TaqMan probes for the six NKP30 transcripts and the β2M housekeeping transcript were designed with the Primer Express software v1.0 (Applied Biosystems). The following primers and probes were used : NKP30-EC-WT: 5'-TTTC-CTCCATGACCACCAGG-3' (SEQ ID NO: 25); NKP30 EX4I: 5'-TTCCCATGTGACAGTGGCATT-3' (SEQ ID NO: 22or 27); NKP30EX4II: 5'-CGGAGAGAGTAGATT TGGCATATT-3' (SEQ ID NO: 28); NKP30EX4III: 5'-GGACCTTTCCAGGTCAGACATT-3' (SEQ ID NO: 29); NKP30Probe (6-FAM/TAMRA): 5'-TGGTGGA-GAAAGAACATCCTCAGCTAGGG-3' (SEQ ID NO: 48); B2MFor: 5'-GATGAGTATGCCTGCCGTGT 3' (SEQ ID NO: 31); B2MRev: 5'-AATTCATCCAATCCAAATGCG-3' (SEQ ID NO: 32); B2MProbe (6-FAM/TAMRA): 5'-AAC-CATGTGACTTTGTCACAGCCCAA-3'(SEQ ID NO: 33).One microliter of first-strand cDNA was mixed with 12,5 µL of 2X TaqMan Universal PCR Master Mix (Applied Biosystems) and 0.75 µL of NKP30 primers (10 µM) and probe (5 µM) or 0,5 µL of β2M primers (10 µM) and probe (5 µM) in a final volume of 25 µL. Temperature cycling and real time fluorescence measurement were done using a StepOnePlus System (Applied Biosystems). The PCR conditions were as follows: initial incubation at 50° C. for 2 min, denaturation at 95° C. for 10 min, followed by 45 cycles at 95° C. for 15 s, and 60° C. (for NKP30a (LONG), b (SHORT) and c (INTERMEDIATE), and β2transcripts) for 1 min. The real time PCR data were analyzed using the $2^{-\Delta C_T}$ method, according to the manufacturer's directions. The proportions of the distinct NKp30 isoforms were determined as the ratio of the relative quantities of each isoform and the total quantity of the three a, b and c isoforms. Unsupervised hierarchical clustering was applied to data log-transformed and median-centred using the Cluster and TreeView programs (average linkage clustering using Pearson's centered correlation as similarity metric)[56.]

Genotyping of NCR3 Exon 4 3'UTR Region.

The TAQMAN Genotyping assay ID: C_7514908_10 was used to genotype the 3790 T/C polymorphism. Briefly, 10 ng of genomic DNA was mixed with 5 µL of 2x TaqMan Genotyping Master Mix (Applied Biosystems) and 0.25 µL of 40x genotyping assay in a final volume of 10 µL.

Temperature cycling and real time fluorescence measurement were done using an StepOnePlus System (Applied Biosystems).

Statistical analyses. The Fisher's exact test and the non parametric Mann-Whitney test were used for comparison of the different groups. These statistical analyses were performed with the GraphPad Prism software version 5. The survival curves were plotted according to the Kaplan-Meier method, and compared using the log-rank test. Independent risk factors for overall and progression free survival were determined using Cox proportional hazards regression model. For survival analysis, the SPSS17.0 software was used.

Results

Expression Cloning of the Three NCR3/NKp30 Exon 4 Isoforms

To elucidate the potential functions of distinct isoforms encoded by NCR3/NKp30 exon 4 (FIG. 1), inventors cloned the three distinct NCR3/NKp30 splice variants into pIRES expression vectors (FIG. 15). These three transcripts, which use exons 4I, 4II, and 4III, have been named NKp30c (INTERMEDIATE), NKp30b (SHORT) and NKp30a (LONG), respectively[23] (SEQ ID NO: 8, 9 and 10). The NKp30a and NKp30b transcripts share the 276 nt at the 3' end, yet diverge in the 5' splice site of their last exon, with the fourth exon of NKp30b (exon 4I) extending into intron 3 of NKp30a by 55 nt. The NKp30a and NKp30b transcripts possess stop codons at position 31664825 and 31664952 respectively, and share a common polyadenylation signal (polyadenylation signal 2) at position 31664690 and a common polyadenylation site at position 31664671 using the NCBI Reference Sequence: NC_000006.10 (SEQ ID NO: 1). The fourth exon of NKp30c (exon 4I) extends into intron 3 of NKp30a and NKp30b and possesses a separate stop codon at position 31665070, and polyadenylation signal and site at positions 31665049 and 31665031 respectively[24]. cDNA constructs encoding the three distinct NKp30 splice variants (displayed in SEQ ID NO: 8, 9 and 10) were stably transfected into Jurkat or NKL cell lines 5' of a polycistronic reporter gene encoding the green fluorescent protein GFP. After selection in G418, surface NKp30 expression was determined by immunofluorescence and cytofluorometry, comparing it with GFP fluorescence or non-transfected cells. All transfected cells expressed comparable levels of GFP and NKp30 (FIG. 16). In addition, the three NKp30-transfected cell lines did not differ in the expression of other NK cell receptors (NKG2D, NKp44, NKp46, KIR, CD25, FIG. 17) from parental cells, allowing for their subsequent functional comparison.

To analyze the differential function of each NKp30 isoform, inventors monitored cytokine release from transfected Jurkat and NKL cells after NKp30 engagement. Cells expressing either NKp30a and NKp30b produced large amounts of IL-2 (FIG. 18A) and IFNγ (FIG. 18B) respectively, whereas cells expressing the NKp30c isoform failed to secrete cytokines in response to NKp30 triggering (FIGS. 18A and B). NKL-NKp30c cells also failed to recognize immature dendritic cells (DC), which is in contrast to NKL-NKp30a or NKL-NKp30b cells that readily secreted IFNγ and TNFα in coculture with DC[39] (FIG. 18C). Similar results were obtained using HEK 293, Mel 888 and GIST 882 tumor cells that express variable levels of NKp30 ligands (data not shown) (FIG. 18D). Cytotoxicity assays revealed that NKL-NKp30a (but not NKL-NKp30b nor NKL-NKp30c) cells exhibited degranulation in direct or redirected killing assays (FIG. 19). Thus, NKp30a appears to be the only isoform that can trigger NK effector functions at the level of cytotoxicity. Altogether, expression cloning thus revealed that NKp30 isoforms significantly differ in their effector functions in vitro and that NKp30c constitutes a functionally deficient isoform, in spite of the fact that this latter molecule appears stable and can be correctly expressed at the cell surface.

Differential Expression Patterns of the NCR3/NKp30 Gene in a Cohort of 80 GIST Patients To investigate the differential expression profile of the three NKp30 isoforms in peripheral NK cells, we performed quantitative RT-PCRs using specific primers for NKp30a, b or c normalized to β2 microglobulin on bulk peripheral blood mononuclear cells (PBMC) from GIST patients or healthy volunteers (HV). Unsupervised hierarchical clustering was applied to log-transformed and median-centered data, using the Cluster and TreeView programs. In FIG. 20, each row represents one NKp30 isoform and each column represents one GIST patient. Red and green colors indicate expression levels above and below the median, respectively. Forty-four out of eighty (55%) of GIST patients exhibited a transcriptional profile where NKp30a and NKp30b were the most predominant isoforms (designated "profile A") (FIGS. 20A and 20B). Conversely, "profile B" individuals presented with a high proportion of the NKp30c isoform (FIGS. 20A and 20B). As expected from the high specificity of the cell distribution of NKp30 expression [26], the results of the RT-PCR revealing the differential expression profile of each NKp30 soform were comparable in PBMC versus bulk NK cells (FIG. 21). It is noteworthy that intra-individual variations over time did not appear significant (as shown on 3-4 different time points during the course of the disease on four representative individuals, FIG. 4).

To interpret the two profiles obtained in patients, inventors compared them with the relative transcription yields of each isoform obtained in a cohort of 56 HV matched in sex, age and geographic origin. Clearly, PBMC or NK cells from HV predominantly express the NKp30a and b isoforms, like profile A GIST (FIG. 20B).

Moreover, profile A and profile B individuals exhibited comparable levels of NKp30 membrane expression, as determined by comparative cytofluorometric analysis of NK cells stained with an antibody specific for the common extracellular portion of NKp30 (FIG. 20C).

Classification of the NKp30 expression profiles from 56 HV using the clustering established for GIST patients, indicates that GIST patients and HV differ in the proportion of individuals with predominant NKp30c expression. While 53% of GIST patients bear profile B, only 30% HV fall into this category (Fisher's exact test: p=0.02) (FIG. 22A).

Altogether, these results indicate the existence of stable phenotypes in the preferential exon 4 usage of NKp30 and that predominant expression of the non-functional NKp30c isoform (profile B) is more frequent in GIST than in the control cohort.

Defective Secretion of TNFα by NK Cells from Profile B (NKp30c) GIST Patients

Next, inventors comparatively assessed TNFα release by purified NK cells from individuals displaying <<profile A>>(n=76) versus <<profile B>> (n=60), after in vitro cross-linking of NKp30. NK cells from GIST patients and HV with profile B exhibited a significant decrease in TNFα production, as compared to profile A individuals (FIG. 22B), in accordance with the functional defects observed in transfected NKL cell lines overexpressing NKp30c (see above). This differential response was obtained when NKp30 was triggered, both in the absence or presence of IL-2 (FIG. 22B). However, there was no difference between profile A and profile B individuals when their NK cells were stimulated with IL-2 alone (in the absence of NKp30-specific antibodies) and TNFα secretion was measured (FIG. 22B). Similar differences in the NKp30-dependent response were obtained when HV were excluded from the analysis and only GIST patients with profiles A and B were compared among each other (FIG. 22C). Importantly, NK cells from profile B patients exhibited a reduced NKp30-driven degranulation compared to profile A patients (FIG. 22D). Hence, interindividual variations in NKp30 splicing affect TNFα secretion and NK cell degranulation. Individuals with profile B that predominantly express the non-functional NKp30c isoform exhibit an overt, yet selective defect in NKp30-driven NK effector functions.

Poor Prognosis of Profile B (NKp30c) GIST Patients

Inventors performed a prospective analysis of the overall survival of GIST patients, which were all treated with the KIT tyrosine kinase inhibitor, imatinib mesylate (IM). The mean clinical follow up of 80 GIST patients was 51 months (±24). The profiles A and B were not significantly different in any of the classical parameters dictating GIST prognosis (Table 1). Thus, the proportion of patients with tumors bearing the exon 11 mutation of the c-KIT protooncogene that is associated with long term survival was 55% and 53% in profile A and profile B respectively (Fisher's exact test: p=ns)[8]. Profile B patients were found to have an inferior overall survival from initial IM treatment in univariate analysis (median survival: 80 months in profile B vs median not reached in profile A, Log-Rank test: p=0.001) (FIG. 23A). In multivariate analysis using Cox model, profile B was retained as the sole independent prognostic factor for overall survival (RR=13.1, 95% CI [4.9-36.1], p=0.01). In contrast, NK cell NKp30 expression levels had no impact on overall survival within the same cohort of patients (FIG. 23B). Altogether, these data indicate that preferential expression of the dysfunctional NKp30c isoform (profile B) predicts dismal therapeutic outcome in GIST patients.

NCR3*3790 T/C (rs986475) Associated with Profile B (NKp30c) Patients

Next, inventors attempted to correlate the preferential expression of NKp30 splice variants with the single nucleotide polymorphism (SNP) genotypes of this gene. Splicing variation, leading to a loss of the polyadenylation signal 2 allowing transcription of NKp30a/b, has been proposed to drive elective NKp30c transcription. Indeed, a SNP (NCR3*3790 T/C, rs986475) located in the polyadenylation signal 2 of the NCR3 gene (FIG. 1) might ablate the transcription of NKp30a/b due to single nucleotide substitutions within the AAUAAA motif, which in turn affect polyadenylation and cleavage efficiencies[59]. Accordingly, our data indicate that NCR3*3790 can control alternative splicing of the NKp30 exon 4. Indeed, 51% among those patients presenting with a profile B pattern (over-representing NKp30c) exhibited a NCR3*3790 TC or CC genotype (versus 0% in GIST patients exhibiting a profile A, Fisher's exact test: p<0.0001) (FIG. 24A). Similarly, about 58% of HV presenting a profile B pattern harbored the NCR3*3790 TC or CC genotype (FIG. 24B). In conclusion, NCR3*3790 T/C is one of the factors that can lead to the aberrant usage of exon 4I that gives rise to the expression of the defective NKp30c isoform.

Gain-of-Function Mutations in c-Kit and FLT3 are Associated with NCR3*3790 T/C in GIST and AML Patients Oncogene driven-DNA damage response may elicit membrane expression of NCR ligands required for NK cell recognition, and this may constitute a mechanism of immune mediated tumor suppression[60]. Therefore, defective NK cell functions might predispose to the development of certain malignancies. In an attempt to match subtle NK cell dysfunctions with defined, oncogene-driven malignancies, inventors chose to determine the frequency of the NCR3*3790 T/C SNP in GIST patients carrying distinct c-kit/PDGFRα mutations (note that some 14% of GIST patients do not carry any mutation in c-kit/PDGFRα), as well as in patients with acute myeloid leukaemia (AML) carrying the FLT3 internal tandem duplication gene variant (FLT3-ITD) (which drives oncogenesis in approximately 15% of AML)[61]. Inventors found a significant association between the presence of the NCR3*3790 T/C SNP and FLT3-ITD in AML. 34.6% (18/52) of AML bearing a FLT3-ITD presented with NCR3*3790 mutant variant versus 18.7% (31/166) in AML lacking the FLT3-ITD oncogene (Fisher's exact test: p=0.01) (FIG. 24C). As for GIST, 21% (n=43) of GIST bearing a detectable c-kit or PDGFRα mutation presented with a NCR3*3790 SNP, while 0% (n=6) of GIST patient lacking detectable c-kit or PDGFRα mutation exhibited this NCR3*3790 SNP (FIG. 24D). These results suggest that a polymorphism affecting NKp30 isoform expression (and by extension NK cell function) may interact genetically in two malignancies driven by the activating mutation of oncogenic receptor tyrosine kinases.

Discussion

Although described in 1999[24], the spliceoforms of NKp30 have never been a matter of investigations. Here inventors describe for the first time, on an important cohort of 80 patients and 56 healthy volunteers, the pathophysiological relevance of NCR3/NKp30 exon 4 spliceoforms during the development of gastrointestinal sarcoma and underscore the protective function of the NKp30a/b isoforms during the course of a targeted treatment.

Alternative splicing is emerging as a major mechanism of functional regulation in the human genome, specifically for neuronal genes and immune-related genes. The use of alternative splicing can be controlled by cells in a developmental, tissue-specific or pathology-dependent manner. Cells use known phosphorylation pathways, relocalization and synthesis of splicing factors to modulate their alternative splicing patterns[62,63]. The human NCR3 gene has several alternatively spliced forms that may code for proteins with at least three unique carboxy termini. cDNA selection followed by human spleen cDNA library screening revealed the three alternate forms of human NCR3/NKp30 exon 4 whose cDNA were sequenced and submitted to GenBank (accession number AF031136-38)[24,25]. Early studies revealed that NKp30 mRNA is expressed in spleen, tonsil, B and NK cell lines and with a different splicing pattern in liver. Indeed, all three principle splice forms of NCR3/NKp30 i.e hNKp30c (INTERMEDIATE) (AF031137), hNKp30b (SHORT) (AF031136), hNKp30a (LONG) (AF031138) were expressed in the human tonsil and NK cells and included the complete exon 2. However, human liver RT-PCR revealed a unique pattern indicating the absence of hNKp30a but the presence of hNKp30b in two isoforms at the level of exon 2 (a complete exon 2 or a 75 bp-deleted exon 2). Using an immunostaining with an anti-NKp30 peptide antibody, Sivakamasundari et al. (2000) could reveal the presence of the NKp30 protein in the germinal center of the lymphoid follicles in tonsils compatible with human NK cells[25]. In 2005, a detailed transcriptional analysis of the 6 isoforms of the human NKp30 gene has been performed both in fetal and adult tissues[32]. It was noteworthy that the V-type Ig domain-containing forms (NKp30a, b and c) were the more highly expressed forms with NKp30c being the most ubiquitous and abundant one (except in fetal brain). Interestingly, NKp30a and b were the predominant spliceoforms of the brain[32].

The mechanisms that control the coordinated expression of the various NKp30 isoforms in NK cells remain unclear. Interestingly, this expression pattern was found similar in different NK cell subsets distinguished on the basis of CD56 expression level and CD27 (ND, not shown). Moreover, GIST therapy with imatinib mesylate did not appear to modulate the pattern of NKp30 expression overtime, spanning several years in some cases (FIG. 4). Pharmacologic compounds such as histone deacetylase inhibitors (trichostatin A, valproic acid, sodium butyrate, suberoylanilide hydroxamic acid), antisense oligonucleotides corresponding to SEQ ID NO: 49-51 (as explained previously), or DNA methyltransferase inhibitors (5-azacytidine, 5-aza-2-deoxycytidine) known to interfere in the alternative splicing of genes may represent valuable tools to control/switch the pattern associated with NK cell defective functions.

Sequences of Interest

```
Nucleotide sequence of NCR3 gene
                                      (SEQ ID NO: 1)
>ref|NC_000006.10|NC_000006:c31668933-31664651
Homo sapiens chromosome 6, reference assembly,
complete sequence.

CCACAAGCTGGCCCCTTGGCCTCCTAGAGACCCTGACATCTCCTCCAG

CAGCATCTGTCCTCTCTCCTCAGGGAGGCAAGCATTTGATGCTCGAGG

TCCCTGGCAGTTGTGGTCCTTGGCAAGTGATGTGTGAGTCCCGTGTGT

CATAGGAAGCTCCCCATCCCCATCTGGTGACCAAAGGCCTGGCTACAA

GTAGTGAGTCCTTCCTCCTCCACCCAGACCTCACTGCTCAGATCCCCT

TCGCCAACTGGGACATCTTCCGACATGGCCTGGATGCTGTTGCTCATC

TTGATCATGGTCCATCCAGGTGACAGGGCGTGCGCTCAGGACCCCAAG

GAGTGTGGGTGGGAGGAGGGAGATCCAGGAGGCTGGACTAGATGCTAT

AGGGAACGGGCTTGGTGGGGGCTGAAACACACGGCTCTGAGGGAGGAG

TGGGACTGCTCCAAAGGTGACACTCAGTGGACTCCCCCAATTCACAGT

CTCTCTGTGTCACCCACTGTGAGGCTTTTTAGTTTGAGAGATCCAAGT

AAATCTATGATAAATTTCTTGGTGAAACTTTTTTTTTTTTTTTTGA

GACTGAGTCTCGCTCTGTCGCCTGGCTGGAGTGCCGTGGTGCGATTTT

GGCTCACTGCAACCTCTGCCTCCCATGTTCAGGTGATTCTCCTGCCTC

AGCCTCCTGAGTAGCTGGGACTACACGCACGCACGACCACACCTGGCT

AATTTTTTTTTTTTGAGACGGAGTCTTGCTCTGTCACCTAGGCTGG

AGTGCAGTGGCATGATCTTGGCTCACTGCAACCTCTGCCTCCTAGATT

CAAGCAATTCTCCTGCCTCAGCCTCCTGTAGCTGGGATTACACGGGCT

GGTCTTGAACTCCTGACCTCAGGTGATCTGCCTGCCTCGGCCTCCTAA

AGTGCGGGATTACAGGCCTGAGCCACTGCGCCCAGCCATTTTTGTAT

TTTTAGTAGAGATGGGGTTTTGCTATGTTGGCCAGGTTGGTCTCAAAC

TCCTGATCTCAAGTGATCTGCCTGCCTCGGTCTCCCAAATTACTGGAA

TTATAGGCATGAGCCACTGCGCCCGCCTGGTGGTGAAACTTTTTTTTT

GAGACAGTTTCATTCTGTTGTCCAGTCTAGAGTACAGTGGCGGTATCT

CAGCTCACTGCAGCCTCCACCTCCTGGGTAAAAATGATTCTCCTGTCT

CAGCCTCCCAAGTAGCTAGGATTACAGGTGCATGCCATTACTGCTGGC

TAACTTGTGTATTTTTAGTAGAGACGAGGTTTCACCATGTTGGCCAGG

CTGGTCTCAAACTCCTGACCTCAGGTGATCCACTCGCCTTGGCCTCCC

AAAGTGTTGGGATTATAGGCGTGAGCCACTGCACCCGGCCGAAACTGT

TTTTAATGAACTGAGAGACCTTAACTATCAGGCATATTATTAACTAAA

TGCAGGAGTTCTCAAAATGTGGATTTCTGGGAACCTAGAACAAATTCT

TAGGCCCCACTCCAGACCTACTGAGTCAAAAACTCGGGGGGTAGGCCC

AGGAATCTGTTCTAGCAGATGCTCCAGGTAATTTCCATACACACTCAA

GTTTGAGAACCACTGAAATAGAATGACTTGTAAATTTCCCTAAGTAGA

TAATTTAATCAGGGATTTTAATATTTGGTTTAATTCATCAACATGGAC

GGGTTAAATAGGAATCTCAACCAATTAAGGCCACGTCTTCACCTGGAG

ATTTAATTAGTTACTTTCTTTAACGAAAACCAAGAGTGGCTGGGTGCA

CTTTGGGAGGCCGAGGCAGGTGGATCACTTGAGATCAGGAGTTTGAGA

CCAGCCTGGTCCGAGGTGGGTGGATCACTTGAGGTCAGGAGTTTGAGA

CCAGATGGTGAAACCCTGTCTCGACTGAAAATACAAAAATTAGCCAGT

CGTGGTGGTGGGTGCCTGTAGTCCCAGCTACTTGGGAGGCTGAGGCAC

CAGGATCGCTTGAACCCAGGGGACGGAGTTTGCAGTGAGCCAAGATTG

CACCACTGCATTCCAGCCTGGGCAACAGAGCAAGACCCCATCTCAAAA

AAAGAAAAAGAAAAAGAGGAAGGATGGCTTACTGTACAATGCCATTT

GTACTAAAATAATACCTGGATAATATAATGAGTGATATTAGTTAACTA

GGCAGCTGCATTCATTAATGAGCTTAATTTCACCATGATGGTTTACAT

TTCAGCTAGACAAGTTACTACTGAACTGGCTGGAGAATGATGGCAGAG

GGTGAGAGTGAGAGTTGGTATAGGAAGAATTTGAAAAATGATTTTTAT

TTTTTATTTTTTGAGATGGAGTCTTGCTTTGTCGCCCAGGCTGGAGTG

CAATGGCGCAATCTTGGCTCACTGCAACCTCTGCCTCCCGGGTTCAAG

CGATTCTCCTGCCTCAGCCTCCCGAGTAGCTGGGATTACAGGTGCACA

CCACCATGCCCGGCTAATTTTTGTATTTTTTAGTAGAGACGGGGTTT

CACCATGTTGGCCAGGATGGTCTCGATCTCCTGACCTGGTGATCCGCC

CACCTCGGCCTCCCAAAGTGCTGGGATTACAGGCGTGAGCCACTGCAC

CCAGCCGAAAAATGATTTAATAAGCAATGTTAAGAAATCAGATTGGTT

AAGAGGGAAGGGTTTAATGAGGCACCCAAAGTATCTATTCCCATGCAC

CCTATGCCTGGAGAAAGCTGGGATGTTCTACTCCAAGCTCTGTTGTCT

TTTCTCTTTGGAATAACTGGGGAGGTGTTTCTCTGGGTCTTCCTTCTG

CCCCCAGGATCCTGTGCTCTCTGGGTGTCCCAGCCCCCTGAGATTCGT

ACCCTGGAAGGATCCTCTGCCTTCCTGCCCTGCTCCTTCAATGCCAGC

CAAGGGAGACTGGCCATTGGCTCCGTCACGTGGTTCCGAGATGAGGTG

TTCCAGGGAAGGAGGTGAGGAATGGAACCCCAGAGTTCAGG

GGCCGCCTGGCCCCACTTGCTTCTTCCCGTTTCCTCCATG

ACCACCAGGCTGAGCTGCACATCCGGGACGTGCGAGGCCATGACGCC

AGCATCTACGTGTGCAGAGTGGAGGTGCTGGGCCTTGGTGTCGGGACA
```

-continued

```
GGGAATGGGACTCGGCTGGTGGTGGAGAAAGGTGAGATGCTGGGAGGT

GGTGTCTCCTCCTGGCTGGAGGCCCCAAGAGGCAATGTCCTTGGGAGG

CAGGGATGCTCCTCTGAGGCCCCTTCCCTCCCTGAGCCTGTGTGCACT

TCTTCCCCAACCCCCGTCTCCATTGCCCCATGCAGAACATCCTCAGCT

AGGGGCTGGTACAGTCCTCCTCCTTCGGGCTGGATTCTATGCTGTCAG

CTTTCTCTCTGTGGCCGTGGGCAGCACCGTCTATTACCAGGGCAAATG

TGAGTAATGGAGCCAGGGGCAATAGTGGACGGGATGGGAGGGGCAGTA

AGAGAGTGGGAGGAGGGAGGACAGAGACCAGGAAGAGGAGAGCCTCGG

GACTGCAACACTGAGCAGCTCCTGTCCTCTCTCTGACCAGGCCACTGT

CACATGGGAACACACTGCCACTCCTCAGATGGGCCCCGAGGAGTGATT

CCAGAGCCCAGATGTCCCTAGTCCTCTTCAAAAGACCCCAATAAATCT

GCCCCACCACTAACTCCTCATGAGTCTCAAGTGTTTTCTTCTCCATTC

TCCAGATGCCAAATCTACTCTCTCCGGATTCCCCCAACTCTGAACTTT

CCCTTCCACCAGGTCTGACCTGGAAAGGTCCAAGAAGGCAGCTGCCGG

CTGTGGTCCCAGCGCCCCTCCCACCACCATGTGGGAGCTCAGCACATC

TGCTTCCCCCAGTCCCAGGAGGCTGAGCCTGATTGTCCTGAGAAATGG

GAAGGATCAGATATGACTCCTCCTTGGCAACTGCCCTTTCCTGCCAGG

CCCACACATACCCTCTTCTGGCTGTTAGGGGAGCTTGGGTCCCTGAAC

ACTGTCATTCACCCAATAAATTACTATTTGACCCCAGAGTGGGTGGAA

GGGTGAGCCATGTGTTTTTTTATTTTAATTTTTAAAAAATTTAAAAA

ATTCCCTATTCAAAGGTCAAAAAGCCACATAAGTTTTGATGATGATCA

ATTTGAACGGAGGCTCGAGATGGACTGAGAGGACTGAGACACAGAAGT

GGGGGGACCATGGTTTTTACTGGCTGGACCACAGGGGACCCTGTCCAC

CCGCC
```
Notes:
Exonic sequences are in bold. The start codon and the stop codons are underlined. The deletion in exon 2 is in italics.

Peptidic Sequences of the Six NKP30 Isoforms:

"short tail-variable Ig-like domain" isoform
(SHORT-WT) - SEQ ID NO: 2
(Vega peptide ID: OTTHUMP00000029163)
MAWMLLLILIMVHPGSCALWVSQPPEIRTLEGSSAFLPCSFNASQGRL
AIGSVTWFRDEVVPGKEVRNGTPEFRGRLAPLASSRFLHDHQAELHIR
DVRGHDASIYVCRVEVLGLGVGTGNGTRLVVEKEHPQLGAGTVLLLRA
GFYAVSFLSVAVGSTVYYQGKYAKSTLSGFPQL "intermediate tail-variable Ig-like domain"
isoform (INTER-WT) - SEQ ID NO: 3
(Vega peptide ID: OTTHUMP00000029164)
MAWMLLLILIMVHPGSCALWVSQPPEIRTLEGSSAFLPCSFNASQGRL
AIGSVTWFRDEVVPGKEVRNGTPEFRGRLAPLASSRFLHDHQAELHIR
DVRGHDASIYVCRVEVLGLGVGTGNGTRLVVEKEHPQLGAGTVLLLRA
GFYAVSFLSVAVGSTVYYQGKCHCHMGTHCHSSDGPRGVIPEPRCP "long tail-variable Ig-like domain" isoform
(LONG-WT) - SEQ ID NO: 4
(Vega peptide ID: OTTHUMP00000029162)
MAWMLLLILIMVHPGSCALWVSQPPEIRTLEGSSAFLPCSFNASQGRL
AIGSVTWFRDEVVPGKEVRNGTPEFRGRLAPLASSRFLHDHQAELHIR
DVRGHDASIYVCRVEVLGLGVGTGNGTRLVVEKEHPQLGAGTVLLLRA
GFYAVSFLSVAVGSTVYYQGKCLTWKGPRRQLPAVVPAPLPPPCGSSA
HLLPPVPGG -continued "short tail-constant Ig-like domain" isoform
(SHORT-DEL) - SEQ ID NO: 5
(no Vega peptide ID)
MAWMLLLILIMVHPGSCALWVSQPPEIRTLEGSSAFLPCSFNASQGRL
AIGSVTWFRDEVVPGKEAELHIRDVRGHDASIYVCRVEVLGLGVGTGN
GTRLVVEKEHPQLGAGTVLLLRAGFYAVSFLSVAVGSTVYYQGKYAKS
TLSGFPQL "intermediate tail-constant Ig-like domain"
isoform (INTER-DEL) - SEQ ID NO: 6
(Vega peptide ID: OTTHUMP00000029165)
MAWMLLLILIMVHPGSCALWVSQPPEIRTLEGSSAFLPCSFNASQGRL
AIGSVTWFRDEVVPGKEAELHIRDVRGHDASIYVCRVEVLGLGVGTGN
GTRLVVEKEHPQLGAGTVLLLRAGFYAVSFLSVAVGSTVYYQGKCHCH
MGTHCHSSDGPRGVIPEPRCP "long tail-constant Ig-like domain" isoform
(LONG-DEL) - SEQ ID NO: 7
(no Vega peptide ID)
MAWMLLLILIMVHPGSCALWVSQPPEIRTLEGSSAFLPCSFNASQGRL
AIGSVTWFRDEVVPGKEAELHIRDVRGHDASIYVCRVEVLGLGVGTGN
GTRLVVEKEHPQLGAGTVLLLRAGFYAVSFLSVAVGSTVYYQGKCLTW
KGPRRQLPAVVPAPLPPPCGSSAHLLPPVPGG
Notes:
Amino acids in gold flank the following domains: (from the left to the right) signal peptide, extra-cellular domain, trans-membrane domain, intracellular domain.
The deleted extra-cellular region characterizing the constant Ig-like domain is underlined in isoforms comprising a variable Ig-like domain.

Nucleotidic Sequences of the Six NKP30 Transcripts:

"short tail-variable Ig-like domain" transcript
(SHORT-WT) - SEQ ID NO: 8
(Vega peptide ID: OTTHUMT00000076211)
ATGGCCTGGATGCTGTTGCTCATCTTGATCATGGTCCATCCAGGATCC
TGTGCTCTCTGGGTGTCCCAGCCCCCTGAGATTCGTACCCTGGAAGGA
TCCTCTGCCTTCCTGCCCTGCTCCTTCAATGCCAGCCAAGGGAGACTG
GCCATTGGCTCCGTCACGTGGTTCCGAGATGAGGTGGTTCCAGGGAAG
GAGGTGAGGAATGGAACCCCAGAGTTCAGGGGCCGCCTGGCCCCACTT
GCTTCTTCCCGTTTCCTCCATGACCACCAGGCTGAGCTGCACATCCGG
GACGTGCGAGGCCATGACGCCAGCATCTACGTGTGCAGAGTGGAGGTG
CTGGGCCTTGGTGTCGGGACAGGGAATGGGACTCGGCTGGTGGTGGAG
AAAGAACATCCTCAGCTAGGGGCTGGTACAGTCCTCCTCCTTCGGGCT
GGATTCTATGCTGTCAGCTTTCTCTCTGTGGCCGTGGGCAGCACCGTC
TATTACCAGGGCAAATATGCCAAATCTACTCTCTCCGGATTCCCCCAA
CTCTGA "intermediate tail-variable Ig-like domain"
transcript (INTER-WT) - SEQ ID NO: 9
(Vega peptide ID: OTTHUMT00000076212)
ATGGCCTGGATGCTGTTGCTCATCTTGATCATGGTCCATCCAGGATCC
TGTGCTCTCTGGGTGTCCCAGCCCCCTGAGATTCGTACCCTGGAAGGA
TCCTCTGCCTTCCTGCCCTGCTCCTTCAATGCCAGCCAAGGGAGACTG
GCCATTGGCTCCGTCACGTGGTTCCGAGATGAGGTGGTTCCAGGGAAG
GAGGTGAGGAATGGAACCCCAGAGTTCAGGGGCCGCCTGGCCCCACTT
GCTTCTTCCCGTTTCCTCCATGACCACCAGGCTGAGCTGCACATCCGG
GACGTGCGAGGCCATGACGCCAGCATCTACGTGTGCAGAGTGGAGGTG
CTGGGCCTTGGTGTCGGGACAGGGAATGGGACTCGGCTGGTGGTGGAG
AAAGAACATCCTCAGCTAGGGGCTGGTACAGTCCTCCTCCTTCGGGCT
GGATTCTATGCTGTCAGCTTTCTCTCTGTGGCCGTGGGCAGCACCGTC
TATTACCAGGGCAAATATGCCACTGTCACATGGGAACACACTGCCACTCC
TCAGATGGGCCCCGAGGAGTGATTCCAGAGCCCAGATGTCCCTAG "long tail-variable Ig-like domain" transcript
(LONG-WT) - SEQ ID NO: 10
(Vega peptide ID: OTTHUMT00000076210)
ATGGCCTGGATGCTGTTGCTCATCTTGATCATGGTCCATCCAGGATCC
TGTGCTCTCTGGGTGTCCCAGCCCCCTGAGATTCGTACCCTGGAAGGA
TCCTCTGCCTTCCTGCCCTGCTCCTTCAATGCCAGCCAAGGGAGACTG
GCCATTGGCTCCGTCACGTGGTTCCGAGATGAGGTGGTTCCAGGGAAG
GAGGTGAGGAATGGAACCCCAGAGTTCAGGGGCCGCCTGGCCCCACTT
GCTTCTTCCCGTTTCCTCCATGACCACCAGGCTGAGCTGCACATCCGG
GACGTGCGAGGCCATGACGCCAGCATCTACGTGTGCAGAGTGGAGGTG
CTGGGCCTTGGTGTCGGGACAGGGAATGGGACTCGGCTGGTGGTGGAG
AAAGAACATCCTCAGCTAGGGGCTGGTACAGTCCTCCTCCTTCGGGCT
GGATTCTATGCTGTCAGCTTTCTCTCTGTGGCCGTGGGCAGCACCGTC
TATTACCAGGGCAAATGTCTGACCTGGAAAGGTCCAAGAAGGCAGCTG -continued
```
CCGGCTGTGGTCCCAGCGCCCCTCCCACCACCATGTGGGAGCTCAGCA
CATCTGCTTCCCCCAGTCCCAGGAGGCTGA
```

"short tail-constant Ig-like domain" transcript
(SHORT-DEL) - SEQ ID NO: 11
(No Vega peptide ID)
```
ATGGCCTGGATGCTGTTGCTCATCTTGATCATGGTCCATCCAGGATCC
TGTGCTCTCTGGGTGTCCCAGCCCCCTGAGATTCGTACCCTGGAAGGA
TCCTCTGCCTTCCTGCCCTGCTCCTTCAATGCCAGCCAAGGGAGACTG
GCCATTGGCTCCGTCACGTGGTTCCGAGATGAGGTGGTTCCAGGGAAG
GAGGCTGAGCTGCACATCCGGGACGTGCGAGGCCATGACGCCAGCATC
TACGTGTGCAGAGTGGAGGTGCTGGGCCTTGGTGTCGGGACAGGGAAT
GGGACTCGGCTGGTGGTGGAGAAAGAACATCCTCAGCTAGGGGCTGGT
ACAGTCCTCCTCCTTCGGGCTGGATTCTATGCTGTCAGCTTTCTCTCT
GTGGCCGTGGGCAGCACCGTCTATTACCAGGGCAAATATGCCAAATC
TACTCTCTCCGGATTCCCCCAACTCTGA
```

"intermediate tail-constant Ig-like domain"
transcript (INTER-DEL) - SEQ ID NO: 12
(Vega peptide ID: OTTHUMT00000076213)
```
ATGGCCTGGATGCTGTTGCTCATCTTGATCATGGTCCATCCAGGATCC
TGTGCTCTCTGGGTGTCCCAGCCCCCTGAGATTCGTACCCTGGAAGGA
TCCTCTGCCTTCCTGCCCTGCTCCTTCAATGCCAGCCAAGGGAGACTG
GCCATTGGCTCCGTCACGTGGTTCCGAGATGAGGTGGTTCCAGGGAAG
GAGGCTGAGCTGCACATCCGGGACGTGCGAGGCCATGACGCCAGCATC
TACGTGTGCAGAGTGGAGGTGCTGGGCCTTGGTGTCGGGACAGGGAAT
GGGACTCGGCTGGTGGTGGAGAAAGAACATCCTCAGCTAGGGGCTGGT
ACAGTCCTCCTCCTTCGGGCTGGATTCTATGCTGTCAGCTTTCTCTCT
GTGGCCGTGGGCAGCACCGTCTATTACCAGGGCAAATGCCACTGTCAC
ATGGGAACACACTGCCACTCCTCAGATGGGCCCCGAGGAGTGATTCCA
GAGCCCAGATGTCCCTAG
```

"long tail-constant Ig-like domain" transcript
(LONG-DEL) - SEQ ID NO: 13
(No Vega peptide ID)
```
ATGGCCTGGATGCTGTTGCTCATCTTGATCATGGTCCATCCAGGATCC
TGTGCTCTCTGGGTGTCCCAGCCCCCTGAGATTCGTACCCTGGAAGGA
TCCTCTGCCTTCCTGCCCTGCTCCTTCAATGCCAGCCAAGGGAGACTG
GCCATTGGCTCCGTCACGTGGTTCCGAGATGAGGTGGTTCCAGGGAAG
GAGGCTGAGCTGCACATCCGGGACGTGCGAGGCCATGACGCCAGCATC
TACGTGTGCAGAGTGGAGGTGCTGGGCCTTGGTGTCGGGACAGGGAAT
GGGACTCGGCTGGTGGTGGAGAAAGAACATCCTCAGCTAGGGGCTGGT
ACAGTCCTCCTCCTTCGGGCTGGATTCTATGCTGTCAGCTTTCTCTCT
GTGGCCGTGGGCAGCACCGTCTATTACCAGGGCAAATGTCTGACCTGG
AAAGGTCCAAGAAGGCAGCTGCCGGCTGTGGTCCCAGCGCCCCTCCCA
CCACCATGTGGGAGCTCAGCACATCTGCTTCCCCCAGTCCCAGGAGGC
TGA
```
Notes:
The start codon is underlined. The original stop codon is in bold.

Primer Sequences

Specific Primers Amplifying 3 Regions of NCR3 Gene Comprising the 3571 G/T and 3790 T/C Polymorphismes and Allowing Genotyping by Sequencing:

```
NCR3_Forward NCR3Frag1 (SEQ ID NO: 14):
5' GATGGGTCTGGGTACTGGTG 3'

NCR3_Reverse NCR3Frag1 (SEQ ID NO: 15):
5' GGGATCTGAGCAGTGAGGTC 3'

NCR3_Forward NCR3Frag2 (SEQ ID NO: 16):
5' ATCCTGTGCTCTCTGGGTGT 3'

NCR3_Reverse NCR3Frag2 (SEQ ID NO: 17):
5' CTGTACCAGCCCCTAGCTGA 3'

NCR3_Forward NCR3Frag3 (SEQ ID NO: 18):
5' CTGAACTTTCCCTTCCACCA 3'

NCR3_Reverse NCR3Frag3 (SEQ ID NO: 19):
5' GGTCCAGCCAGTAAAAACCA 3'
```

Specific Primers Amplifying the Six NKp30 RNA Transcripts for Quantification Based on SYBRGREEN Detection:

```
NCR3_Forward NKp30Fex2 (SEQ ID NO: 20):
5' GTGAGGAATGGAACCCCAGAGT 3'

NCR3_Forward NKp30Fex2del (SEQ ID NO: 21):
5' GTGGTTCCAGGGAAGGAGGC 3'

NCR3_Reverse NKp30Rex4I (SEQ ID NO: 22 or 27):
5' TTCCCATGTGACAGTGGCATT 3'

NCR3_Reverse NKp30Rex4II (SEQ ID NO: 23):
5' CCGGAGAGAGTAGATTTGGCATATT 3'

NCR3_Reverse NKp30Rex4III (SEQ ID NO: 24):
5' TGGACCTTTCCAGGTCAGACATT 3'
```

Specific Primers Amplifying the Six NKp30 RNA Transcripts for Quantification Based on TAQMAN PROBE Detection:

```
NCR3_Forward NKP30 EC-WT (SEQ ID NO: 25):
5' TTTCCTCCATGACCACCAGG 3'

NCR3_Forward NKP30 EC-DEL (SEQ ID NO: 26):
5' GGTTCCAGGGAAGGAGGCT 3'

NCR3_Reverse NKP30 EX4I (SEQ ID NO: 27 or 22):
5' TTCCCATGTGACAGTGGCATT 3'

NCR3_Reverse NKP30EX4II (SEQ ID NO: 28):
5' CGGAGAGAGTAGATTTGGCATATT 3'

NCR3_Reverse NKP30EX4III (SEQ ID NO: 29):
5' GGACCTTTCCAGGTCAGACATT 3'

NKP30Probe (6-FAM/TAMRA) (SEQ ID NO: 30):
5' AGCTGCACATCCGGGACGTGC 3'

B2M_Forward B2Mfor (SEQ ID NO: 31):
5' GATGAGTATGCCTGCCGTGT 3'

B2M_Reverse B2MRev (SEQ ID NO: 32):
5' AATTCATCCAATCCAAATGCG 3'

B2MProbe (6-FAM/TAMRA) (SEQ ID NO: 33):
5' AACCATGTGACTTTGTCACAGCCCAA 3'
```

HPLC-Purified Primers Used for the Cloning of Six NKP30 Isoforms:

```
NCR3_Forward KPNI-NKp30 (SEQ ID NO: 34):
5' GGGGTACCCCGACATGGCCTGGATGCTGTT 3'

NCR3_Reverse EcoRI-SHORT (SEQ ID NO: 35):
5' GGAATTCCTGGTGGAAGGGAAAGTTCAG 3'

NCR3_Reverse EcoRI-INTER (SEQ ID NO: 36):
5' GGAATTCCTTTTGAAGAGGACTAGGGACATC 3'

NCR3_Reverse EcoRI-LONG (SEQ ID NO: 37):
5' GGAATTCCATTTCTCAGGACAATCAGG 3'
```

Peptidic Sequences of the NKp30 Extracellular and Intracellular Domains and Amino Acid Peptides Used to Obtain Specific Anti-NKp30 Antibodies:

Variable Ig-like extracellular domain of NKp30 isoforms - SEQ ID NO: 38
GSCALWVSQPPEIRTLEGSSAFLPCSFNASQGRLAIGSVTWFRDEVVP GKEVRNGTPEFRGRLAPLASSRFLHDHQAELHIRDVRGHDASIYVCRV EVLGLGVGTGNGTRLVVEKE Constant Ig-like extracellular domain of NKp30 isoforms - SEQ ID NO: 39
GSCALWVSQPPEIRTLEGSSAFLPCSFNASQGRLAIGSVTWFRDEVVP GKEAELHIRDVRGHDASIYVCRVEVLGLGVGTGNGTRLVVEKE

```
Short intracellular domain of NKp30
isoforms - SEQ ID NO: 40
YAKSTLSGFPQL

Intermediate intracellular domain of NKp30
isoforms - SEQ ID NO: 41
CHCHMGTHCHSSDGPRGVIPEPRCP Long intracellular domain of NKp30
isoforms - SEQ ID NO: 42
CLTWKGPRRQLPAVVPAPLPPPCGSSAHLLPPVPGG Peptide used to obtain specific anti-NKp30
variable Ig-like extracellular domain
antibody - SEQ ID NO: 43
VRNGTPEFRGRLAPLASSRFLHDHQ Peptide used to obtain specific anti-NKp30
constant Ig-like extracellular domain
antibody - SEQ ID NO: 44
EVVPGKEAELHIRD Peptide used to obtain specific anti-NKp30
short intracellular domain antibody -
SEQ ID NO: 45
YAKSTLSGFPQL Peptide used to obtain specific anti-NKp30
intermediate intracellular domain antibody -
SEQ ID NO: 46
CHCHMGTHCHSSDGPRGVIPEPRCP Peptide used to obtain specific anti-NKp30
long intracellular domain antibody -
SEQ ID NO: 47
CLTWKGPRRQLPAVVPAPLPPPCGSSAHLLPPVPGG
Notes:
The deleted extra-cellular region characterizing the constant
Ig-like domain is underlined in the variable Ig-like domain.
The sequences of peptides used to obtain specific anti-NKp30
antibodies are in bold in the sequences of NKp30 extracellular
and intracellular domains.

NKP30Probe (6-FAM/TAMRA):
                                        (SEQ ID NO: 48)
5' TGGTGGAGAAAGAACATCCTCAGCTAGGG 3'

Sequence (Target: polyadenylation signal 1)
                                        (SEQ ID NO: 49)
5' GGGGCAGATTTATTGGGGTC 3'

Sequence (Target: polyadenylation site 1)
                                        (SEQ ID NO: 50)
5' CTCATGAGGAGTTAGTGGT 3'

Sequence INTER blocking antisense oligonucleotide
                                        (SEQ ID NO: 51)
5' GTGACAGTGGCCTGGTCAGA 3'
```

REFERENCES

1. Raut, C. P., Morgan, J. A. & Ashley, S. W. Current issues in gastrointestinal stromal tumors: incidence, molecular biology, and contemporary treatment of localized and advanced disease. *Curr Opin Gastroenterol* 23, 149-58 (2007).
2. Fletcher, C. D. et al. Diagnosis of gastrointestinal stromal tumors: a consensus approach. *Int J Surg Pathol* 10, 81-9 (2002).
3. Joensuu, H. et al. Management of malignant gastrointestinal stromal tumours. *Lancet Oncol* 3, 655-64 (2002).
4. Hirota, S. et al. Gain-of-function mutations of c-kit in human gastrointestinal stromal tumors. *Science* 279, 577-80 (1998).
5. Rubin, B. P. et al. KIT activation is a ubiquitous feature of gastrointestinal stromal tumors. *Cancer Res* 61, 8118-21 (2001).
6. Heinrich, M. C. et al. PDGFRA activating mutations in gastrointestinal stromal tumors. *Science* 299, 708-10 (2003).
7. Corless, C. L. et al. PDGFRA mutations in gastrointestinal stromal tumors: frequency, spectrum and in vitro sensitivity to imatinib. *J Clin Oncol* 23, 5357-64 (2005).
8. Heinrich, M. C. et al. Kinase mutations and imatinib response in patients with metastatic gastrointestinal stromal tumor. *J Clin Oncol* 21, 4342-9 (2003).
9. Rubin, B. P., Heinrich, M. C. & Corless, C. L. Gastrointestinal stromal tumour. *Lancet* 369, 1731-41 (2007).
10. Van Glabbeke, M. et al. Initial and late resistance to imatinib in advanced gastrointestinal stromal tumors are predicted by different prognostic factors: a European Organisation for Research and Treatment of Cancer-Italian Sarcoma Group-Australasian Gastrointestinal Trials Group study. *J Clin Oncol* 23, 5795-804 (2005).
11. Matthay, K. K. Neuroblastoma: a clinical challenge and biologic puzzle. *CA Cancer J Clin* 45, 179-92 (1995).
12. Vasudevan, S. A., Nuchtern, J. G. & Shohet, J. M. Gene profiling of high risk neuroblastoma. *World J Surg* 29, 317-24 (2005).
13. Cerwenka, A. & Lanier, L. L. Natural killer cells, viruses and cancer. *Nat Rev Immunol* 1, 41-9 (2001).
14. Kim, S., Iizuka, K., Aguila, H. L., Weissman, I. L. & Yokoyama, W. M. In vivo natural killer cell activities revealed by natural killer cell-deficient mice. *Proc Natl Acad Sci USA* 97, 2731-6 (2000).
15. Terme, M., Ullrich, E., Delahaye, N. F., Chaput, N. & Zitvogel, L. Natural killer cell-directed therapies: moving from unexpected results to successful strategies. *Nat Immunol* 9, 486-94 (2008).
16. Borg, C. et al. Novel mode of action of c-kit tyrosine kinase inhibitors leading to NK cell-dependent antitumor effects. *J Clin Invest* 114, 379-88 (2004).
17. Menard, C. et al. Natural killer cell IFN-gamma levels predict long-term survival with imatinib mesylate therapy in gastrointestinal stromal tumor-bearing patients. *Cancer Res* 69, 3563-9 (2009).
18. Sun, J. C., Beilke, J. N. & Lanier, L. L. Adaptive immune features of natural killer cells. *Nature* 457, 557-61 (2009).
19. Cooper, M. A. et al. Cytokine-induced memory-like natural killer cells. *Proc Natl Acad Sci USA* 106, 1915-9 (2009).
20. Gruen, J. R. et al. A transcription map of the major histocompatibility complex (MHC) class I region. *Genomics* 36, 70-85 (1996).
21. Horton, R. et al. Gene map of the extended human MHC. *Nat Rev Genet* 5, 889-99 (2004).
22. Gruen, J. R. & Weissman, S. M. Human MHC class III and IV genes and disease associations. *Front Biosci* 6, D960-72 (2001).
23. Nalabolu, S. R., Shukla, H., Nallur, G., Parimoo, S. & Weissman, S. M. Genes in a 220-kb region spanning the TNF cluster in human MHC. *Genomics* 31, 215-22 (1996).
24. Neville, M. J. & Campbell, R. D. A new member of the Ig superfamily and a V-ATPase G subunit are among the predicted products of novel genes close to the TNF locus in the human MHC. *J Immunol* 162, 4745-54 (1999).
25. Sivakamasundari, R., Raghunathan, A., Zhang, C. Y., Chowdhury, R. R. & Weissman, S. M. Expression and 25. cellular localization of the protein encoded by the 1C7 gene: a recently described component of the MHC. *Immunogenetics* 51, 723-32 (2000).
26. Pende, D. et al. Identification and molecular characterization of NKp30, a novel triggering receptor involved in natural cytotoxicity mediated by human natural killer cells. *J Exp Med* 190, 1505-16 (1999).
27. Ferlazzo, G. et al. Human dendritic cells activate resting natural killer (NK) cells and are recognized via the NKp30 receptor by activated NK cells. *J Exp Med* 195, 343-51 (2002).
28. Bottino, C., Castriconi, R., Morena, L. & Moretta, A. Cellular ligands of activating NK receptors. *Trends Immunol* 26, 221-6 (2005).
29. Tang, Q. et al. Umbilical cord blood T cells express multiple natural cytotoxicity receptors after IL-15 stimulation, but only NKp30 is functional. *J Immunol* 181, 4507-15 (2008).
30. Ponnampalam, A. P., Gargett, C. E. & Rogers, P. A. Identification and hormonal regulation of a novel form of NKp30 in human endometrial epithelium. *Eur J Immunol* 38, 216-26 (2008).
31. Xie, T. et al. Analysis of the gene-dense major histocompatibility complex class III region and its comparison to mouse. *Genome Res* 13, 2621-36 (2003).
32. Hollyoake, M., Campbell, R. D. & Aguado, B. NKp30 (NCR3) is a pseudogene in 12 inbred and wild mouse strains, but an expressed gene in *Mus caroli*. *Mol Biol Evol* 22, 1661-72 (2005).
33. Backman-Petersson, E., Miller, J. R., Hollyoake, M., Aguado, B. & Butcher, G. W. Molecular characterization of the novel rat NK receptor 1C7. *Eur J Immunol* 33, 342-51 (2003).
34. Augugliaro, R. et al. Selective cross-talk among natural cytotoxicity receptors in human natural killer cells. *Eur J Immunol* 33, 1235-41 (2003).
35. Nowbakht, P. et al. Ligands for natural killer cell-activating receptors are expressed upon the maturation of normal myelomonocytic cells but at low levels in acute myeloid leukemias. *Blood* 105, 3615-22 (2005).
36. Fernandez, N. C. et al. Dendritic cells directly trigger NK cell functions: cross-talk relevant in innate anti-tumor immune responses in vivo. *Nat Med* 5, 405-11 (1999).
37. Zitvogel, L. Dendritic and natural killer cells cooperate in the control/switch of innate immunity. *J Exp Med* 195, F9-14 (2002).
38. Lucas, M., Schachterle, W., Oberle, K., Aichele, P. & Diefenbach, A. Dendritic cells prime natural killer cells by trans-presenting interleukin 15. *Immunity* 26, 503-17 (2007).
39. Vitale, M. et al. NK-dependent DC maturation is mediated by TNFalpha and IFNgamma released upon engagement of the NKp30 triggering receptor. *Blood* 106, 566-71 (2005).
40. Martin-Fontecha, A. et al. Induced recruitment of NK cells to lymph nodes provides IFN-gamma for T(H)1 priming. *Nat Immunol* 5, 1260-5 (2004).
41. Adam, C. et al. DC-NK cell cross talk as a novel CD4+ T-cell-independent pathway for antitumor CTL induction. *Blood* 106, 338-44 (2005).
42. Mavoungou, E., Held, J., Mewono, L. & Kremsner, P. G. A duffy binding-like domain is involved in the NKp30-mediated recognition of *Plasmodium falciparum*-parasitized erythrocytes by natural killer cells. *J Infect Dis* 195, 1521-31 (2007).
43. Delahaye, N. F., Barbier, M., Fumoux, F. & Rihet, P. Association analyses of NCR3 polymorphisms with *P. falciparum* mild malaria. *Microbes Infect* 9, 160-6 (2007).
44. Korbel, D. S., Newman, K. C., Almeida, C. R., Davis, D. M. & Riley, E. M. Heterogeneous human NK cell responses to *Plasmodium falciparum*-infected erythrocytes. *J Immunol* 175, 7466-73 (2005).
45. Bloushtain, N. et al. Membrane-associated heparan sulfate proteoglycans are involved in the recognition of cellular targets by NKp30 and NKp46. *J Immunol* 173, 2392-401 (2004).
46. Warren, H. S., Jones, A. L., Freeman, C., Bettadapura, J. & Parish, C. R. Evidence that the cellular ligand for the human NK cell activation receptor NKp30 is not a heparan sulfate glycosaminoglycan. *J Immunol* 175, 207-12 (2005).
47. Hershkovitz, O. et al. Altered Glycosylation of Recombinant NKp30 Hampers Binding to Heparan Sulfate: a Lesson for the Use of Recombinant Immuno-Receptors as an Immunological Tool. *Glycobiology* (2007).
48. Pogge von Strandmann, E. et al. Human leukocyte antigen-B-associated transcript 3 is released from tumor cells and engages the NKp30 receptor on natural killer cells. *Immunity* 27, 965-74 (2007).
49. Byrd, A., Hoffmann, S. C., Jarahian, M., Momburg, F. & Watzl, C. Expression analysis of the ligands for the Natural Killer cell receptors NKp30 and NKp44. *PLoS ONE* 2, e1339 (2007).
50. Kim, H. R. et al. Anti-cancer activity and mechanistic features of a NK cell activating molecule. *Cancer Immunol Immunother* (2009).
51. Kiyoi, H. et al. Prognostic implication of FLT3 and N-RAS gene mutations in acute myeloid leukemia. *Blood* 93, 3074-80 (1999).
52. Emile, J. F. et al. Length analysis of polymerase chain reaction products: a sensitive and reliable technique for the detection of mutations in KIT exon 11 in gastrointestinal stromal tumors. *Diagn Mol Pathol* 11, 107-12 (2002).
53. Du, L. & Gatti, R. A. Progress toward therapy with antisense-mediated splicing modulation. *Curr Opin Mol Ther* 11, 116-23 (2009).
54. Blay, J. Y. et al. Prospective multicentric randomized phase III study of imatinib in patients with advanced gastrointestinal stromal tumors comparing interruption versus continuation of treatment beyond 1 year: the French Sarcoma Group. *J Clin Oncol* 25, 1107-13 (2007).
55. Verweij, J. et al. Progression-free survival in gastrointestinal stromal tumours with high-dose imatinib: randomised trial. *Lancet* 364, 1127-34 (2004).
56. Eisen, M. B., Spellman, P. T., Brown, P. O. & Botstein, D. Cluster analysis and display of genome-wide expression patterns. *Proc Natl Acad Sci USA* 95, 14863-8 (1998).
57. Bennett, J. M. et al. Proposed revised criteria for the classification of acute myeloid leukemia. A report of the French-American-British Cooperative Group. *Ann Intern Med* 103, 620-5 (1985).
58. Harris, N. L. et al. World Health Organization classification of neoplastic diseases of the hematopoietic and lymphoid tissues: report of the Clinical Advisory Committee meeting-Airlie House, Virginia, November 1997. *J Clin Oncol* 17, 3835-49 (1999).

59. Sheets, M. D., Ogg, S. C. & Wickens, M.P. Point mutations in AAUAAA and the poly (A) addition site: effects on the accuracy and efficiency of cleavage and polyadenylation in vitro. *Nucleic Acids Res* 18, 5799-805 (1990).
60. Gasser, S., Orsulic, S., Brown, E. J. & Raulet, D. H. The DNA damage pathway regulates innate immune system ligands of the NKG2D receptor. *Nature* 436, 1186-90 (2005).
61. Nakao, M. et al. Internal tandem duplication of the flt3 gene found in acute myeloid leukemia. *Leukemia* 10, 1911-8 (1996).
62. Ladd, A. N. & Cooper, T. A. Finding signals that regulate alternative splicing in the post-genomic era. *Genome Biol* 3, reviews0008 (2002).
63. Stamm, S. Signals and their transduction pathways regulating alternative splicing: a new dimension of the human genome. *Hum Mol Genet* 11, 2409-16 (2002).

The invention claimed is:

1. A method of treating a human subject having a gastrointestinal stromal tumor (GIST), the method comprising
measuring the relative amount of NKp30c, NKp30b, and NKp30a RNA transcript isoforms in a natural killer (NK) cell sample or in a peripheral mononuclear cell sample comprising NK cells obtained from the human subject;
detecting a higher amount of NKp30c RNA transcript isoform than NKp30b and NKp30a RNA transcript isoforms in said NK cell sample or said peripheral mononuclear cell sample comprising NK cells; and
administering to the human subject having a higher amount of NKp30c RNA transcript isoform a pharmaceutical composition comprising trichostatin A (TSA) or 5-azacitidine.

2. The method of claim 1, wherein the relative amounts of NKp30 RNA transcript isoforms are measured by selective amplification with nucleic acid primers that amplify NKp30c, NKp30b and/or NKp30a RNA transcript isoforms, or with a nucleic acid primer that discriminates between NKp30c, NKp30b and/or NKp30a RNA transcript isoforms of NKp30 and/or between constant and variable Ig-like domain transcript isoforms.

3. The method of claim 2, wherein said primers amplify NKp30c, NKp30b and/or NKp30a RNA transcript isoforms and are SEQ ID NO: 25; SEQ ID NO: 22 or SEQ ID NO: 27; SEQ ID NO: 28; and SEQ ID NO: 29.

4. The method of claim 1, wherein treating further comprises administering a chemotherapeutic agent, a tyrosine kinase inhibitor (TKI) and/or a farnesyl-transferase inhibitor (FTI) simultaneously, separately or sequentially.

5. The method of claim 2, wherein the relative amounts of NKp30 RNA transcript isoforms are measured by polymerase chain reaction (PCR), reverse transcription PCR (RT-PCR), ligase chain reaction, or strand displacement amplification.

6. The method of claim 5, wherein the relative amounts of NKp30 RNA transcript isoforms are measured by RT-PCR using primers SEQ ID NO: 25; SEQ ID NO: 22 or SEQ ID NO: 27; SEQ ID NO: 28; and SEQ ID NO: 29.

* * * * *

UNITED STATES PATENT AND TRADEMARK OFFICE
CERTIFICATE OF CORRECTION

PATENT NO. : 9,593,376 B2
APPLICATION NO. : 12/994192
DATED : March 14, 2017
INVENTOR(S) : Laurence Zitvogel et al.

It is certified that error appears in the above-identified patent and that said Letters Patent is hereby corrected as shown below:

In the Specification

Column 39,
Line 40, "NKP30EX4I:" should read --NKP30EX4II:--.
Line 41, "NKP30EX4I:" should read --NKP30EX4III:--.
Line 62, "$2^{-\Delta\Delta C_T}$" should read --$2^{-\Delta\Delta C_T}$--.

Column 46,
Line 16, "H-4A3," should read --H4A3,--.

Column 48,
Line 28, "soform" should read --isoform--.

Column 51,
Line 55, " CAAGCAATTCTCCTGCCTCAGCCTCCTGTAGCTGGGATTACACGGCT "
should read -- CAAGCAATTCTCCTGCCTCAGCCTCCTGTAGCTGGGATTACAAGC GCGCACCACCACACCCAACTAATTTTTGTATTTTAGTAGAGACAGGGTTTTAC CATGTTGGCCGGGCT --.

Column 52,
Line 60, " TTCCAGGGAAGGAGGTGAGGAATGGAACCCCAGAGTTCAGG"
should read -- GTTCCAGGGAAGGAGGTGAGGAATGGAACCCCAGAGTTCAGG --.

Column 53,
Line 39, " GGGGGGACCATGGTTTTTACTGGCTGGACCACAGGGGACCCTGTCCAC"
should read -- GGGGGGACCATGGTTTTTACTGGCTGGACCACAGGGGACCCTGT CCAC --.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 51

<210> SEQ ID NO 1
<211> LENGTH: 4281
<212> TYPE: DNA
<213> ORGANISM: Homo sapiens

<400> SEQUENCE: 1
ccacaagctg gcccttggc ctcctagaga ccctgacatc tcctccagca gcatctgtcc      60
tctctcctca gggaggcaag catttgatgc tcgaggtccc tggcagttgt ggtccttggc     120
aagtgatgtg tgagtcccgt gtgtcatagg aagctcccca tccccatctg gtgaccaaag     180
gcctggctac aagtagtgag tccttcctcc tccacccaga cctcactgct cagatcccct     240
tcgccaactg ggacatcttc cgacatggcc tggatgctgt tgctcatctt gatcatggtc     300
catccaggtg acagggcgtg cgctcaggac cccaaggagt gtggtggga ggagggagat      360 ccaggaggct ggactagatg ctataggaa cgggcttggt ggggctgaa acacacggct       420 ctgagggagg agtgggactg ctccaaaggt gacactcagt ggactccccc aattcacagt     480
ctctctgtgt cacccactgt gaggcttttt agtttgagag atccaagtaa atctatgata     540
aatttcttgg tgaaactttt ttttttttt ttttgagact gagtctcgct ctgtcgcctg      600
gctggagtgc cgtggtgcga ttttggctca ctgcaacctc tgcctcccat gttcaggtga     660
ttctcctgcc tcagcctcct gagtagctgg gactacacgc acgcacgacc acacctggct     720 aattttttt tttttgaga cggagtcttg ctctgtcacc taggctggag tgcagtggca      780
tgatcttggc tcactgcaac ctctgcctcc tagattcaag caattctcct gcctcagcct     840
cctgtagctg ggattacaag cgcgcaccac cacacccaac taatttttgt attttagta     900 gagacaggt tttaccatgt tggccggct ggtcttgaac tcctgacctc aggtgatctg      960
cctgcctcgg cctcctaaag tgcggggatt acaggcctga gccactgcgc ccagccattt    1020
ttgtattttt agtagagatg gggttttgct atgttggcca ggttggtctc aaactcctga    1080
tctcaagtga tctgcctgcc tcggtctccc aaattactgg aattataggc atgagccact    1140
gcgcccgcct ggtggtgaaa cttttttttt gagacagttt cattctgttg tccagtctag    1200
agtacagtgg cggtatctca gctcactgca gcctccacct cctgggtaaa aatgattctc    1260
ctgtctcagc ctcccaagta gctaggatta caggtgcatg ccattactgc tggctaactt    1320
gtgtattttt agtagagacg aggtttcacc atgttggcca ggctggtctc aaactcctga    1380
cctcaggtga tccactcgcc ttggcctccc aaagtgttgg gattataggc gtgagccact    1440
gcacccggcc gaaactgttt ttaatgaact gagagacctt aactatcagg catattatta    1500
actaaatgca ggagttctca aaatgtggat ttctgggaac ctagaacaaa ttcttaggcc    1560
ccactccaga cctactgagt caaaaactcg ggggtaggc ccaggaatct gttctagcag     1620
atgctccagg taatttccat acacactcaa gtttgagaac cactgaaata gaatgacttg    1680
taaatttccc taagtagata atttaatcag ggatttaat atttggttta attcatcaac    1740
```

-continued

```
atggacgggt taaataggaa tctcaaccaa ttaaggccac gtcttcacct ggagatttaa    1800
ttagttactt tctttaacga aaaccaagag tggctgggtg cactttggga ggccgaggca    1860
ggtggatcac ttgagatcag gagtttgaga ccagcctggt ccgaggtggg tggatcactt    1920
gaggtcagga gtttgagacc agatggtgaa accctgtctc gactgaaaat acaaaaatta    1980
gccagtcgtg gtggtgggtg cctgtagtcc cagctacttg ggaggctgag gcaccaggat    2040
cgcttgaacc caggggacgg agtttgcagt gagccaagat tgcaccactg cattccagcc    2100
tgggcaacag agcaagaccc catctcaaaa aaagaaaaaa gaaaagagg aaggatggct     2160 tactgtacaa tgccatttgt actaaaataa tacctggata atataatgag tgatattagt    2220
taactaggca gctgcattca ttaatgagct taatttcacc atgatggttt acatttcagc    2280
tagacaagtt actactgaac tggctggaga atgatggcag agggtgagag tgagagttgg    2340
tataggaaga atttgaaaaa tgattttat ttttttatttt ttgagatgga gtcttgcttt    2400
gtcgcccagg ctggagtgca atggcgcaat cttggctcac tgcaacctct gcctcccggg    2460
ttcaagcgat tctcctgcct cagcctcccg agtagctggg attacaggtg cacaccacca    2520
tgcccggcta atttttgtat tttttagta gagacggggt ttcaccatgt tggccaggat     2580
ggtctcgatc tcctgacctg gtgatccgcc cacctcggcc tcccaaagtg ctgggattac    2640
aggcgtgagc cactgcaccc agccgaaaaa tgatttaata agcaatgtta agaaatcaga    2700
ttggttaaga gggaagggtt taatgaggca cccaaagtat ctattcccat gcaccctatg    2760
cctggagaaa gctgggatgt tctactccaa gctctgttgt cttttctctt tggaataact    2820
ggggaggtgt ttctctgggt cttccttctg ccccccaggat cctgtgctct ctgggtgtcc    2880 cagcccctg agattcgtac cctggaagga tcctctgcct tcctgccctg ctccttcaat     2940
gccagccaag ggagactggc cattggctcc gtcacgtggt tccgagatga ggtggttcca    3000
gggaaggagg tgaggaatgg aaccccagag ttcaggggcc gcctggcccc acttgcttct    3060
tcccgtttcc tccatgacca ccaggctgag ctgcacatcc gggacgtgcg aggccatgac    3120
gccagcatct acgtgtgcag agtggaggtg ctgggccttg gtgtcgggac agggaatggg    3180
actcggctgg tggtggagaa aggtgagatg ctgggaggtg gtgtctcctc ctggctggag    3240
gccccaagag gcaatgtcct tgggaggcag ggatgctcct ctgaggcccc ttccctccct    3300
gagcctgtgt gcacttcttc cccaaccccc gtctccattg ccccatgcag aacatcctca    3360 gctagggggct ggtacagtcc tcctccttcg ggctggattc tatgctgtca gctttctctc    3420 tgtgccgtg gcagcaccg tctattacca gggcaaatgt gagtaatgga gccagggca      3480 atagtggacg ggatgggagg ggcagtaaga gagtgggagg agggaggaca gagaccagga    3540
agaggagagc ctcgggactg caacactgag cagctcctgt cctctctctg accaggccac    3600
tgtcacatgg gaacacactg ccactcctca gatgggcccc gaggagtgat tccagagccc    3660
agatgtccct agtcctcttc aaaagacccc aataaatctg ccccaccact aactcctcat    3720
gagtctcaag tgttttcttc tccattctcc agatgccaaa tctactctct ccggattccc    3780
ccaactctga actttccctt ccaccaggtc tgacctggaa aggtccaaga aggcagctgc    3840
cggctgtggt cccagcgccc ctcccaccac catgtgggag ctcagcacat ctgcttcccc    3900
cagtcccagg aggctgagcc tgattgtcct gagaaatggg aaggatcaga tatgactcct    3960
ccttggcaac tgccctttcc tgccaggccc acacataccc tcttctggct gttagggag    4020 cttgggtccc tgaacactgt cattcaccca ataaattact atttgacccc agagtgggtg    4080
```

-continued

```
gaagggtgag ccatgtgttt ttttatttt aatttttaaa aaatttaaaa aattccctat      4140
tcaaaggtca aaaagccaca taagttttga tgatgatcaa tttgaacgga ggctcgagat      4200
ggactgagag gactgagaca cagaagtggg gggaccatgg tttttactgg ctggaccaca      4260
gggggaccct gtccacccgc c                                                4281
```

<210> SEQ ID NO 2
<211> LENGTH: 177
<212> TYPE: PRT
<213> ORGANISM: Homo sapiens
<220> FEATURE:
<221> NAME/KEY: PEPTIDE
<222> LOCATION: (1)..(177)
<223> OTHER INFORMATION: "short tail-variable Ig-like domain" isoform
   (SHORT-WT) (Vega peptide ID : OTTHUMP00000029163)

<400> SEQUENCE: 2

Met Ala Trp Met Leu Leu Leu Ile Leu Ile Met Val His Pro Gly Ser
1               5                   10                  15

Cys Ala Leu Trp Val Ser Gln Pro Pro Glu Ile Arg Thr Leu Glu Gly
            20                  25                  30

Ser Ser Ala Phe Leu Pro Cys Ser Phe Asn Ala Ser Gln Gly Arg Leu
        35                  40                  45

Ala Ile Gly Ser Val Thr Trp Phe Arg Asp Glu Val Val Pro Gly Lys
    50                  55                  60

Glu Val Arg Asn Gly Thr Pro Glu Phe Arg Gly Arg Leu Ala Pro Leu
65                  70                  75                  80

Ala Ser Ser Arg Phe Leu His Asp His Gln Ala Glu Leu His Ile Arg
                85                  90                  95

Asp Val Arg Gly His Asp Ala Ser Ile Tyr Val Cys Arg Val Glu Val
            100                 105                 110

Leu Gly Leu Gly Val Gly Thr Gly Asn Gly Thr Arg Leu Val Val Glu
        115                 120                 125

Lys Glu His Pro Gln Leu Gly Ala Gly Thr Val Leu Leu Leu Arg Ala
    130                 135                 140

Gly Phe Tyr Ala Val Ser Phe Leu Ser Val Ala Val Gly Ser Thr Val
145                 150                 155                 160

Tyr Tyr Gln Gly Lys Tyr Ala Lys Ser Thr Leu Ser Gly Phe Pro Gln
                165                 170                 175

Leu

<210> SEQ ID NO 3
<211> LENGTH: 190
<212> TYPE: PRT
<213> ORGANISM: Homo sapiens
<220> FEATURE:
<221> NAME/KEY: PEPTIDE
<222> LOCATION: (1)..(190)
<223> OTHER INFORMATION: "intermediate tail-variable Ig-like domain"
   isoform (INTER-WT) (Vega peptide ID : OTTHUMP00000029164)

<400> SEQUENCE: 3

Met Ala Trp Met Leu Leu Leu Ile Leu Ile Met Val His Pro Gly Ser
1               5                   10                  15

Cys Ala Leu Trp Val Ser Gln Pro Pro Glu Ile Arg Thr Leu Glu Gly
            20                  25                  30

Ser Ser Ala Phe Leu Pro Cys Ser Phe Asn Ala Ser Gln Gly Arg Leu
        35                  40                  45

Ala Ile Gly Ser Val Thr Trp Phe Arg Asp Glu Val Val Pro Gly Lys

```
                 50                  55                  60
Glu Val Arg Asn Gly Thr Pro Glu Phe Arg Gly Arg Leu Ala Pro Leu
 65                  70                  75                  80

Ala Ser Ser Arg Phe Leu His Asp His Gln Ala Glu Leu His Ile Arg
                 85                  90                  95

Asp Val Arg Gly His Asp Ala Ser Ile Tyr Val Cys Arg Val Glu Val
                100                 105                 110

Leu Gly Leu Gly Val Gly Thr Gly Asn Gly Thr Arg Leu Val Val Glu
                115                 120                 125

Lys Glu His Pro Gln Leu Gly Ala Gly Thr Val Leu Leu Leu Arg Ala
                130                 135                 140

Gly Phe Tyr Ala Val Ser Phe Leu Ser Val Ala Val Gly Ser Thr Val
145                 150                 155                 160

Tyr Tyr Gln Gly Lys Cys His Cys His Met Gly Thr His Cys His Ser
                165                 170                 175

Ser Asp Gly Pro Arg Gly Val Ile Pro Glu Pro Arg Cys Pro
                180                 185                 190

<210> SEQ ID NO 4
<211> LENGTH: 201
<212> TYPE: PRT
<213> ORGANISM: Homo sapiens
<220> FEATURE:
<221> NAME/KEY: PEPTIDE
<222> LOCATION: (1)..(201)
<223> OTHER INFORMATION: "long tail-variable Ig-like domain" isoform
      (LONG-WT) (Vega peptide ID : OTTHUMP00000029162)

<400> SEQUENCE: 4

Met Ala Trp Met Leu Leu Ile Leu Ile Met Val His Pro Gly Ser
 1               5                   10                  15

Cys Ala Leu Trp Val Ser Gln Pro Pro Glu Ile Arg Thr Leu Glu Gly
                 20                  25                  30

Ser Ser Ala Phe Leu Pro Cys Ser Phe Asn Ala Ser Gln Gly Arg Leu
                 35                  40                  45

Ala Ile Gly Ser Val Thr Trp Phe Arg Asp Glu Val Val Pro Gly Lys
 50                  55                  60

Glu Val Arg Asn Gly Thr Pro Glu Phe Arg Gly Arg Leu Ala Pro Leu
 65                  70                  75                  80

Ala Ser Ser Arg Phe Leu His Asp His Gln Ala Glu Leu His Ile Arg
                 85                  90                  95

Asp Val Arg Gly His Asp Ala Ser Ile Tyr Val Cys Arg Val Glu Val
                100                 105                 110

Leu Gly Leu Gly Val Gly Thr Gly Asn Gly Thr Arg Leu Val Val Glu
                115                 120                 125

Lys Glu His Pro Gln Leu Gly Ala Gly Thr Val Leu Leu Leu Arg Ala
                130                 135                 140

Gly Phe Tyr Ala Val Ser Phe Leu Ser Val Ala Val Gly Ser Thr Val
145                 150                 155                 160

Tyr Tyr Gln Gly Lys Cys Leu Thr Trp Lys Gly Pro Arg Arg Gln Leu
                165                 170                 175

Pro Ala Val Val Pro Ala Pro Leu Pro Pro Cys Gly Ser Ser Ala
                180                 185                 190

His Leu Leu Pro Pro Val Pro Gly Gly
                195                 200
```

<210> SEQ ID NO 5
<211> LENGTH: 152
<212> TYPE: PRT
<213> ORGANISM: Homo sapiens
<220> FEATURE:
<221> NAME/KEY: PEPTIDE
<222> LOCATION: (1)..(152)
<223> OTHER INFORMATION: "short tail-constant Ig-like domain" isoform
      (SHORT-DEL) (no Vega peptide ID)

<400> SEQUENCE: 5

Met Ala Trp Met Leu Leu Ile Leu Ile Met Val His Pro Gly Ser
1               5                   10                  15

Cys Ala Leu Trp Val Ser Gln Pro Pro Glu Ile Arg Thr Leu Glu Gly
            20                  25                  30

Ser Ser Ala Phe Leu Pro Cys Ser Phe Asn Ala Ser Gln Gly Arg Leu
        35                  40                  45

Ala Ile Gly Ser Val Thr Trp Phe Arg Asp Glu Val Val Pro Gly Lys
    50                  55                  60

Glu Ala Glu Leu His Ile Arg Asp Val Arg Gly His Asp Ala Ser Ile
65                  70                  75                  80

Tyr Val Cys Arg Val Glu Val Leu Gly Leu Gly Val Gly Thr Gly Asn
                85                  90                  95

Gly Thr Arg Leu Val Val Glu Lys Glu His Pro Gln Leu Gly Ala Gly
            100                 105                 110

Thr Val Leu Leu Leu Arg Ala Gly Phe Tyr Ala Val Ser Phe Leu Ser
        115                 120                 125

Val Ala Val Gly Ser Thr Val Tyr Tyr Gln Gly Lys Tyr Ala Lys Ser
    130                 135                 140

Thr Leu Ser Gly Phe Pro Gln Leu
145                 150

<210> SEQ ID NO 6
<211> LENGTH: 165
<212> TYPE: PRT
<213> ORGANISM: Homo sapiens
<220> FEATURE:
<221> NAME/KEY: PEPTIDE
<222> LOCATION: (1)..(165)
<223> OTHER INFORMATION: "intermediate tail-constant Ig-like domain"
      isoform (INTER-DEL) (Vega peptide ID : OTTHUMP00000029165)

<400> SEQUENCE: 6

Met Ala Trp Met Leu Leu Ile Leu Ile Met Val His Pro Gly Ser
1               5                   10                  15

Cys Ala Leu Trp Val Ser Gln Pro Pro Glu Ile Arg Thr Leu Glu Gly
            20                  25                  30

Ser Ser Ala Phe Leu Pro Cys Ser Phe Asn Ala Ser Gln Gly Arg Leu
        35                  40                  45

Ala Ile Gly Ser Val Thr Trp Phe Arg Asp Glu Val Val Pro Gly Lys
    50                  55                  60

Glu Ala Glu Leu His Ile Arg Asp Val Arg Gly His Asp Ala Ser Ile
65                  70                  75                  80

Tyr Val Cys Arg Val Glu Val Leu Gly Leu Gly Val Gly Thr Gly Asn
                85                  90                  95

Gly Thr Arg Leu Val Val Glu Lys Glu His Pro Gln Leu Gly Ala Gly
            100                 105                 110

Thr Val Leu Leu Leu Arg Ala Gly Phe Tyr Ala Val Ser Phe Leu Ser
        115                 120                 125

```
Val Ala Val Gly Ser Thr Val Tyr Tyr Gln Gly Lys Cys His Cys His
    130                 135                 140
Met Gly Thr His Cys His Ser Ser Asp Gly Pro Arg Gly Val Ile Pro
145                 150                 155                 160
Glu Pro Arg Cys Pro
                165

<210> SEQ ID NO 7
<211> LENGTH: 176
<212> TYPE: PRT
<213> ORGANISM: Homo sapiens
<220> FEATURE:
<221> NAME/KEY: PEPTIDE
<222> LOCATION: (1)..(176)
<223> OTHER INFORMATION: "long tail-constant Ig-like domain" isoform
      (LONG-DEL) (no Vega peptide ID)

<400> SEQUENCE: 7

Met Ala Trp Met Leu Leu Ile Leu Ile Met Val His Pro Gly Ser
1               5                   10                  15

Cys Ala Leu Trp Val Ser Gln Pro Pro Glu Ile Arg Thr Leu Glu Gly
                20                  25                  30

Ser Ser Ala Phe Leu Pro Cys Ser Phe Asn Ala Ser Gln Gly Arg Leu
            35                  40                  45

Ala Ile Gly Ser Val Thr Trp Phe Arg Asp Glu Val Val Pro Gly Lys
50                  55                  60

Glu Ala Glu Leu His Ile Arg Asp Val Arg Gly His Asp Ala Ser Ile
65                  70                  75                  80

Tyr Val Cys Arg Val Glu Val Leu Gly Leu Gly Val Gly Thr Gly Asn
                85                  90                  95

Gly Thr Arg Leu Val Val Glu Lys Glu His Pro Gln Leu Gly Ala Gly
                100                 105                 110

Thr Val Leu Leu Leu Arg Ala Gly Phe Tyr Ala Val Ser Phe Leu Ser
            115                 120                 125

Val Ala Val Gly Ser Thr Val Tyr Tyr Gln Gly Lys Cys Leu Thr Trp
    130                 135                 140

Lys Gly Pro Arg Arg Gln Leu Pro Ala Val Val Pro Ala Pro Leu Pro
145                 150                 155                 160

Pro Pro Cys Gly Ser Ser Ala His Leu Leu Pro Pro Val Pro Gly Gly
                165                 170                 175

<210> SEQ ID NO 8
<211> LENGTH: 534
<212> TYPE: DNA
<213> ORGANISM: Homo sapiens

<400> SEQUENCE: 8
atggcctgga tgctgttgct catcttgatc atggtccatc caggatcctg tgctctctgg    60
gtgtcccagc cccctgagat tcgtaccctg gaaggatcct ctgccttcct gccctgctcc   120
ttcaatgcca gccaagggag actggccatt ggctccgtca cgtggttccg agatgaggtg   180
gttccaggga aggaggtgag gaatggaacc ccagagttca ggggccgcct ggccccactt   240
gcttcttccc gtttcctcca tgaccaccag gctgagctgc acatccggga cgtgcgaggc   300
catgacgcca gcatctacgt gtgcagagtg gaggtgctgg ccttggtgt cgggacaggg   360 aatgggactc ggctggtggt ggagaaagaa catcctcagc tagggctgg tacagtcctc   420 ctccttcggg ctggattcta tgctgtcagc tttctctctg tggccgtggg cagcaccgtc   480
```
tattaccagg gcaaatatgc caaatctact ctctccggat tcccccaact ctga    534

<210> SEQ ID NO 9
<211> LENGTH: 573
<212> TYPE: DNA
<213> ORGANISM: Homo sapiens

<400> SEQUENCE: 9
atggcctgga tgctgttgct catcttgatc atggtccatc caggatcctg tgctctctgg    60
gtgtcccagc ccctgagat tcgtaccctg aaggatcct ctgccttcct gccctgctcc    120
ttcaatgcca gccaagggag actggccatt ggctccgtca cgtggttccg agatgaggtg    180
gttccaggga aggaggtgag gaatggaacc ccagagttca ggggccgcct ggccccactt    240
gcttcttccc gtttcctcca tgaccaccag gctgagctgc acatccggga cgtgcgaggc    300
catgacgcca gcatctacgt gtgcagagtg gaggtgctgg gccttggtgt cgggacaggg    360
aatgggactc ggctggtggt ggagaaagaa catcctcagc tagggctgg tacagtcctc    420
ctccttcggg ctggattcta tgctgtcagc tttctctctg tggccgtggg cagcaccgtc    480
tattaccagg gcaaatgcca ctgtcacatg gaacacact gccactcctc agatgggccc    540
cgaggagtga ttccagagcc cagatgtccc tag    573

<210> SEQ ID NO 10
<211> LENGTH: 606
<212> TYPE: DNA
<213> ORGANISM: Homo sapiens

<400> SEQUENCE: 10
atggcctgga tgctgttgct catcttgatc atggtccatc caggatcctg tgctctctgg    60
gtgtcccagc ccctgagat tcgtaccctg aaggatcct ctgccttcct gccctgctcc    120
ttcaatgcca gccaagggag actggccatt ggctccgtca cgtggttccg agatgaggtg    180
gttccaggga aggaggtgag gaatggaacc ccagagttca ggggccgcct ggccccactt    240
gcttcttccc gtttcctcca tgaccaccag gctgagctgc acatccggga cgtgcgaggc    300
catgacgcca gcatctacgt gtgcagagtg gaggtgctgg gccttggtgt cgggacaggg    360
aatgggactc ggctggtggt ggagaaagaa catcctcagc tagggctgg tacagtcctc    420
ctccttcggg ctggattcta tgctgtcagc tttctctctg tggccgtggg cagcaccgtc    480
tattaccagg gcaaatgtct gacctggaaa ggtccaagaa ggcagctgcc ggctgtggtc    540
ccagcgcccc tcccaccacc atgtgggagc tcagcacatc tgcttccccc agtcccagga    600
ggctga    606

<210> SEQ ID NO 11
<211> LENGTH: 459
<212> TYPE: DNA
<213> ORGANISM: Homo sapiens

<400> SEQUENCE: 11
atggcctgga tgctgttgct catcttgatc atggtccatc caggatcctg tgctctctgg    60
gtgtcccagc ccctgagat tcgtaccctg aaggatcct ctgccttcct gccctgctcc    120
ttcaatgcca gccaagggag actggccatt ggctccgtca cgtggttccg agatgaggtg    180
gttccaggga aggaggctga gctgcacatc cgggacgtgc aggccatga cgccagcatc    240
tacgtgtgca gagtggaggt gctgggcctt ggtgtcggga cagggaatgg gactcggctg    300
gtggtggaga aagaacatcc tcagctaggg gctggtacag tcctcctcct tcgggctgga    360

```
ttctatgctg tcagctttct ctctgtggcc gtgggcagca ccgtctatta ccagggcaaa    420
tatgccaaat ctactctctc cggattcccc caactctga                           459
```

```
<210> SEQ ID NO 12
<211> LENGTH: 498
<212> TYPE: DNA
<213> ORGANISM: Homo sapiens

<400> SEQUENCE: 12
atggcctgga tgctgttgct catcttgatc atggtccatc caggatcctg tgctctctgg    60
gtgtcccagc ccctgagat tcgtaccctg gaaggatcct ctgccttcct gccctgctcc    120
ttcaatgcca gccaagggag actggccatt ggctccgtca cgtggttccg agatgaggtg    180
gttccaggga aggaggctga gctgcacatc cgggacgtgc gaggccatga cgccagcatc    240
tacgtgtgca gagtggaggt gctgggcctt ggtgtcggga cagggaatgg gactcggctg    300
gtggtggaga aagaacatcc tcagctaggg gctggtacag tcctcctcct tcgggctgga    360
ttctatgctg tcagctttct ctctgtggcc gtgggcagca ccgtctatta ccagggcaaa    420
tgccactgtc acatgggaac acactgccac tcctcagatg ggccccgagg agtgattcca    480
gagcccagat gtccctag                                                  498
```

```
<210> SEQ ID NO 13
<211> LENGTH: 531
<212> TYPE: DNA
<213> ORGANISM: Homo sapiens

<400> SEQUENCE: 13
atggcctgga tgctgttgct catcttgatc atggtccatc caggatcctg tgctctctgg    60
gtgtcccagc ccctgagat tcgtaccctg gaaggatcct ctgccttcct gccctgctcc    120
ttcaatgcca gccaagggag actggccatt ggctccgtca cgtggttccg agatgaggtg    180
gttccaggga aggaggctga gctgcacatc cgggacgtgc gaggccatga cgccagcatc    240
tacgtgtgca gagtggaggt gctgggcctt ggtgtcggga cagggaatgg gactcggctg    300
gtggtggaga aagaacatcc tcagctaggg gctggtacag tcctcctcct tcgggctgga    360
ttctatgctg tcagctttct ctctgtggcc gtgggcagca ccgtctatta ccagggcaaa    420
tgtctgacct ggaaaggtcc aagaaggcag ctgccggctg tggtcccagc gcccctccca    480
ccaccatgtg ggagctcagc acatctgctt cccccagtcc caggaggctg a             531
```

```
<210> SEQ ID NO 14
<211> LENGTH: 20
<212> TYPE: DNA
<213> ORGANISM: Artificial sequence
<220> FEATURE:
<223> OTHER INFORMATION: NCR3_Forward NCR3Frag1
<220> FEATURE:
<221> NAME/KEY: primer_bind
<222> LOCATION: (1)..(20)

<400> SEQUENCE: 14
gatgggtctg ggtactggtg                                                20
```

```
<210> SEQ ID NO 15
<211> LENGTH: 20
<212> TYPE: DNA
<213> ORGANISM: Artificial sequence
<220> FEATURE:
<223> OTHER INFORMATION: NCR3_Reverse NCR3Frag1
```

-continued

```
<220> FEATURE:
<221> NAME/KEY: primer_bind
<222> LOCATION: (1)..(20)

<400> SEQUENCE: 15
gggatctgag cagtgaggtc                                               20

<210> SEQ ID NO 16
<211> LENGTH: 20
<212> TYPE: DNA
<213> ORGANISM: Artificial sequence
<220> FEATURE:
<223> OTHER INFORMATION: NCR3_Forward NCR3Frag2
<220> FEATURE:
<221> NAME/KEY: primer_bind
<222> LOCATION: (1)..(20)

<400> SEQUENCE: 16
atcctgtgct ctctgggtgt                                               20

<210> SEQ ID NO 17
<211> LENGTH: 20
<212> TYPE: DNA
<213> ORGANISM: Artificial sequence
<220> FEATURE:
<223> OTHER INFORMATION: NCR3_Reverse NCR3Frag2
<220> FEATURE:
<221> NAME/KEY: primer_bind
<222> LOCATION: (1)..(20)

<400> SEQUENCE: 17
ctgtaccagc ccctagctga                                               20

<210> SEQ ID NO 18
<211> LENGTH: 20
<212> TYPE: DNA
<213> ORGANISM: Artificial sequence
<220> FEATURE:
<223> OTHER INFORMATION: NCR3_Forward NCR3Frag3
<220> FEATURE:
<221> NAME/KEY: primer_bind
<222> LOCATION: (1)..(20)

<400> SEQUENCE: 18
ctgaactttc ccttccacca                                               20

<210> SEQ ID NO 19
<211> LENGTH: 20
<212> TYPE: DNA
<213> ORGANISM: Artificial sequence
<220> FEATURE:
<223> OTHER INFORMATION: NCR3_Reverse NCR3Frag3
<220> FEATURE:
<221> NAME/KEY: primer_bind
<222> LOCATION: (1)..(20)

<400> SEQUENCE: 19
ggtccagcca gtaaaaacca                                               20

<210> SEQ ID NO 20
<211> LENGTH: 22
<212> TYPE: DNA
<213> ORGANISM: Artificial sequence
<220> FEATURE:
<223> OTHER INFORMATION: NCR3_Forward NKp30Fex2
<220> FEATURE:
<221> NAME/KEY: primer_bind
<222> LOCATION: (1)..(22)
```

<400> SEQUENCE: 20
gtgaggaatg aacccccaga gt                                              22

<210> SEQ ID NO 21
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: NCR3_Forward NKp30Fex2del

<400> SEQUENCE: 21
gtggttccag ggaaggaggc                                                 20

<210> SEQ ID NO 22
<211> LENGTH: 21
<212> TYPE: DNA
<213> ORGANISM: Artificial sequence
<220> FEATURE:
<223> OTHER INFORMATION: NCR3_Reverse NKp30Rex4I
<220> FEATURE:
<221> NAME/KEY: primer_bind
<222> LOCATION: (1)..(21)

<400> SEQUENCE: 22
ttcccatgtg acagtggcat t                                               21

<210> SEQ ID NO 23
<211> LENGTH: 25
<212> TYPE: DNA
<213> ORGANISM: Artificial sequence
<220> FEATURE:
<223> OTHER INFORMATION: NCR3_Forward NKp30Fex2del
<220> FEATURE:
<221> NAME/KEY: primer_bind
<222> LOCATION: (1)..(25)

<400> SEQUENCE: 23
ccggagagag tagatttggc atatt                                           25

<210> SEQ ID NO 24
<211> LENGTH: 23
<212> TYPE: DNA
<213> ORGANISM: Artificial sequence
<220> FEATURE:
<223> OTHER INFORMATION: NCR3_Reverse NKp30Rex4III
<220> FEATURE:
<221> NAME/KEY: primer_bind
<222> LOCATION: (1)..(23)

<400> SEQUENCE: 24 tggaccttc caggtcagac att                                              23

<210> SEQ ID NO 25
<211> LENGTH: 20
<212> TYPE: DNA
<213> ORGANISM: Artificial sequence
<220> FEATURE:
<223> OTHER INFORMATION: NCR3_Forward NKP30 EC-WT
<220> FEATURE:
<221> NAME/KEY: primer_bind
<222> LOCATION: (1)..(20)

<400> SEQUENCE: 25
tttcctccat gaccaccagg                                                 20

```
<210> SEQ ID NO 26
<211> LENGTH: 19
<212> TYPE: DNA
<213> ORGANISM: Artificial sequence
<220> FEATURE:
<223> OTHER INFORMATION: NCR3_Forward NKP30 EC-DEL
<220> FEATURE:
<221> NAME/KEY: primer_bind
<222> LOCATION: (1)..(19)

<400> SEQUENCE: 26
ggttccaggg aaggaggct                                                    19

<210> SEQ ID NO 27
<211> LENGTH: 21
<212> TYPE: DNA
<213> ORGANISM: Artificial sequence
<220> FEATURE:
<223> OTHER INFORMATION: NCR3_Reverse NKP30 EX4I
<220> FEATURE:
<221> NAME/KEY: primer_bind
<222> LOCATION: (1)..(21)

<400> SEQUENCE: 27
ttcccatgtg acagtggcat t                                                 21

<210> SEQ ID NO 28
<211> LENGTH: 24
<212> TYPE: DNA
<213> ORGANISM: Artificial sequence
<220> FEATURE:
<223> OTHER INFORMATION: NCR3_Reverse NKP30EX4II
<220> FEATURE:
<221> NAME/KEY: primer_bind
<222> LOCATION: (1)..(24)

<400> SEQUENCE: 28
cggagagagt agatttggca tatt                                              24

<210> SEQ ID NO 29
<211> LENGTH: 22
<212> TYPE: DNA
<213> ORGANISM: Artificial sequence
<220> FEATURE:
<223> OTHER INFORMATION: NCR3_Reverse NKP30EX4III
<220> FEATURE:
<221> NAME/KEY: primer_bind
<222> LOCATION: (1)..(22)

<400> SEQUENCE: 29
ggacctttcc aggtcagaca tt                                                22

<210> SEQ ID NO 30
<211> LENGTH: 21
<212> TYPE: DNA
<213> ORGANISM: Artificial sequence
<220> FEATURE:
<223> OTHER INFORMATION: NKP30Probe (6-FAM/TAMRA)
<220> FEATURE:
<221> NAME/KEY: primer_bind
<222> LOCATION: (1)..(21)

<400> SEQUENCE: 30
agctgcacat ccgggacgtg c                                                 21

<210> SEQ ID NO 31
<211> LENGTH: 20
<212> TYPE: DNA
<213> ORGANISM: Artificial sequence
```

```
<220> FEATURE:
<223> OTHER INFORMATION: B2M_Forward B2Mfor
<220> FEATURE:
<221> NAME/KEY: primer_bind
<222> LOCATION: (1)..(20)

<400> SEQUENCE: 31
gatgagtatg cctgccgtgt                                               20

<210> SEQ ID NO 32
<211> LENGTH: 21
<212> TYPE: DNA
<213> ORGANISM: Artificial sequence
<220> FEATURE:
<223> OTHER INFORMATION: B2M_Reverse B2MRev
<220> FEATURE:
<221> NAME/KEY: primer_bind
<222> LOCATION: (1)..(21)

<400> SEQUENCE: 32
aattcatcca atccaaatgc g                                             21

<210> SEQ ID NO 33
<211> LENGTH: 26
<212> TYPE: DNA
<213> ORGANISM: Artificial sequence
<220> FEATURE:
<223> OTHER INFORMATION: B2MProbe (6-FAM/TAMRA)
<220> FEATURE:
<221> NAME/KEY: primer_bind
<222> LOCATION: (1)..(26)

<400> SEQUENCE: 33
aaccatgtga ctttgtcaca gcccaa                                        26

<210> SEQ ID NO 34
<211> LENGTH: 30
<212> TYPE: DNA
<213> ORGANISM: Artificial sequence
<220> FEATURE:
<223> OTHER INFORMATION: NCR3_Forward KPNI-NKp30
<220> FEATURE:
<221> NAME/KEY: primer_bind
<222> LOCATION: (1)..(30)

<400> SEQUENCE: 34
ggggtacccc gacatggcct ggatgctgtt                                    30

<210> SEQ ID NO 35
<211> LENGTH: 28
<212> TYPE: DNA
<213> ORGANISM: Artificial sequence
<220> FEATURE:
<223> OTHER INFORMATION: NCR3_Reverse EcoRI-SHORT
<220> FEATURE:
<221> NAME/KEY: primer_bind
<222> LOCATION: (1)..(28)

<400> SEQUENCE: 35
ggaattcctg gtggaaggga aagttcag                                      28

<210> SEQ ID NO 36
<211> LENGTH: 31
<212> TYPE: DNA
<213> ORGANISM: Artificial sequence
<220> FEATURE:
<223> OTHER INFORMATION: NCR3_Reverse EcoRI-INTER
<220> FEATURE:
<221> NAME/KEY: primer_bind
```

<222> LOCATION: (1)..(31)

<400> SEQUENCE: 36 ggaattccttt tgaagagga ctagggacat c        31

<210> SEQ ID NO 37
<211> LENGTH: 27
<212> TYPE: DNA
<213> ORGANISM: Artificial sequence
<220> FEATURE:
<223> OTHER INFORMATION: NCR3_Reverse EcoRI-LONG
<220> FEATURE:
<221> NAME/KEY: primer_bind
<222> LOCATION: (1)..(27)

<400> SEQUENCE: 37
ggaattccat ttctcaggac aatcagg        27

<210> SEQ ID NO 38
<211> LENGTH: 116
<212> TYPE: PRT
<213> ORGANISM: Homo sapiens
<220> FEATURE:
<221> NAME/KEY: PEPTIDE
<222> LOCATION: (1)..(116)
<223> OTHER INFORMATION: Variable Ig-like extracellular domain of NKp30
      isoforms

<400> SEQUENCE: 38

Gly Ser Cys Ala Leu Trp Val Ser Gln Pro Pro Glu Ile Arg Thr Leu
1               5                   10                  15

Glu Gly Ser Ser Ala Phe Leu Pro Cys Ser Phe Asn Ala Ser Gln Gly
            20                  25                  30

Arg Leu Ala Ile Gly Ser Val Thr Trp Phe Arg Asp Glu Val Val Pro
        35                  40                  45

Gly Lys Glu Val Arg Asn Gly Thr Pro Glu Phe Arg Gly Arg Leu Ala
    50                  55                  60

Pro Leu Ala Ser Ser Arg Phe Leu His Asp His Gln Ala Glu Leu His
65                  70                  75                  80

Ile Arg Asp Val Arg Gly His Asp Ala Ser Ile Tyr Val Cys Arg Val
                85                  90                  95

Glu Val Leu Gly Leu Gly Val Gly Thr Gly Asn Gly Thr Arg Leu Val
            100                 105                 110

Val Glu Lys Glu
        115

<210> SEQ ID NO 39
<211> LENGTH: 91
<212> TYPE: PRT
<213> ORGANISM: Homo sapiens
<220> FEATURE:
<221> NAME/KEY: PEPTIDE
<222> LOCATION: (1)..(91)
<223> OTHER INFORMATION: Constant Ig-like extracellular domain of
      NKp30 isoforms

<400> SEQUENCE: 39

Gly Ser Cys Ala Leu Trp Val Ser Gln Pro Pro Glu Ile Arg Thr Leu
1               5                   10                  15

Glu Gly Ser Ser Ala Phe Leu Pro Cys Ser Phe Asn Ala Ser Gln Gly
            20                  25                  30

Arg Leu Ala Ile Gly Ser Val Thr Trp Phe Arg Asp Glu Val Val Pro
        35                  40                  45

Gly Lys Glu Ala Glu Leu His Ile Arg Asp Val Arg Gly His Asp Ala
            50                  55                  60

Ser Ile Tyr Val Cys Arg Val Glu Val Leu Gly Leu Gly Val Gly Thr
 65                  70                  75                  80

Gly Asn Gly Thr Arg Leu Val Val Glu Lys Glu
                 85                  90

<210> SEQ ID NO 40
<211> LENGTH: 12
<212> TYPE: PRT
<213> ORGANISM: Homo sapiens
<220> FEATURE:
<221> NAME/KEY: PEPTIDE
<222> LOCATION: (1)..(12)
<223> OTHER INFORMATION: Short intracellular domain of NKp30 isoforms

<400> SEQUENCE: 40

Tyr Ala Lys Ser Thr Leu Ser Gly Phe Pro Gln Leu
 1               5                  10

<210> SEQ ID NO 41
<211> LENGTH: 25
<212> TYPE: PRT
<213> ORGANISM: Homo sapiens
<220> FEATURE:
<221> NAME/KEY: PEPTIDE
<222> LOCATION: (1)..(25)
<223> OTHER INFORMATION: Intermediate intracellular domain of NKp30
      isoforms

<400> SEQUENCE: 41

Cys His Cys His Met Gly Thr His Cys His Ser Ser Asp Gly Pro Arg
 1               5                  10                  15

Gly Val Ile Pro Glu Pro Arg Cys Pro
             20                  25

<210> SEQ ID NO 42
<211> LENGTH: 36
<212> TYPE: PRT
<213> ORGANISM: Homo sapiens
<220> FEATURE:
<221> NAME/KEY: PEPTIDE
<222> LOCATION: (1)..(36)
<223> OTHER INFORMATION: Long intracellular domain of NKp30 isoforms

<400> SEQUENCE: 42

Cys Leu Thr Trp Lys Gly Pro Arg Arg Gln Leu Pro Ala Val Val Pro
 1               5                  10                  15

Ala Pro Leu Pro Pro Pro Cys Gly Ser Ser Ala His Leu Leu Pro Pro
             20                  25                  30

Val Pro Gly Gly
         35

<210> SEQ ID NO 43
<211> LENGTH: 25
<212> TYPE: PRT
<213> ORGANISM: Artificial sequence
<220> FEATURE:
<223> OTHER INFORMATION: Peptide used to obtain specific anti-NKp30
      variable Ig-like extracellular domain antibody
<220> FEATURE:
<221> NAME/KEY: PEPTIDE
<222> LOCATION: (1)..(25)

<400> SEQUENCE: 43

-continued

Val Arg Asn Gly Thr Pro Glu Phe Arg Gly Arg Leu Ala Pro Leu Ala
1               5                   10                  15

Ser Ser Arg Phe Leu His Asp His Gln
            20                  25

<210> SEQ ID NO 44
<211> LENGTH: 14
<212> TYPE: PRT
<213> ORGANISM: Artificial sequence
<220> FEATURE:
<223> OTHER INFORMATION: Peptide used to obtain specific anti-NKp30
      constant Ig-like extracellular domain antibody
<220> FEATURE:
<221> NAME/KEY: PEPTIDE
<222> LOCATION: (1)..(14)

<400> SEQUENCE: 44

Glu Val Val Pro Gly Lys Glu Ala Glu Leu His Ile Arg Asp
1               5                   10

<210> SEQ ID NO 45
<211> LENGTH: 12
<212> TYPE: PRT
<213> ORGANISM: Artificial sequence
<220> FEATURE:
<223> OTHER INFORMATION: Peptide used to obtain specific anti-NKp30
      short intracellular domain antibody
<220> FEATURE:
<221> NAME/KEY: PEPTIDE
<222> LOCATION: (1)..(12)

<400> SEQUENCE: 45

Tyr Ala Lys Ser Thr Leu Ser Gly Phe Pro Gln Leu
1               5                   10

<210> SEQ ID NO 46
<211> LENGTH: 25
<212> TYPE: PRT
<213> ORGANISM: Artificial sequence
<220> FEATURE:
<223> OTHER INFORMATION: Peptide used to obtain specific anti-NKp30
      intermediate intracellular domain antibody
<220> FEATURE:
<221> NAME/KEY: PEPTIDE
<222> LOCATION: (1)..(25)

<400> SEQUENCE: 46

Cys His Cys His Met Gly Thr His Cys His Ser Ser Asp Gly Pro Arg
1               5                   10                  15

Gly Val Ile Pro Glu Pro Arg Cys Pro
            20                  25

<210> SEQ ID NO 47
<211> LENGTH: 36
<212> TYPE: PRT
<213> ORGANISM: Artificial sequence
<220> FEATURE:
<223> OTHER INFORMATION: Peptide used to obtain specific anti-NKp30
      long intracellular domain antibody
<220> FEATURE:
<221> NAME/KEY: PEPTIDE
<222> LOCATION: (1)..(36)

<400> SEQUENCE: 47

Cys Leu Thr Trp Lys Gly Pro Arg Arg Gln Leu Pro Ala Val Val Pro
1               5                   10                  15

Ala Pro Leu Pro Pro Pro Cys Gly Ser Ser Ala His Leu Leu Pro Pro
            20                  25                  30

```
<210> SEQ ID NO 48
<211> LENGTH: 29
<212> TYPE: DNA
<213> ORGANISM: artificial sequence
<220> FEATURE:
<223> OTHER INFORMATION: NKP30Probe (6-FAM/TAMRA)

<400> SEQUENCE: 48
tggtggagaa agaacatcct cagctaggg                                      29

<210> SEQ ID NO 49
<211> LENGTH: 20
<212> TYPE: DNA
<213> ORGANISM: artificial sequence
<220> FEATURE:
<223> OTHER INFORMATION: sequence targeting polyadenylation signal 1

<400> SEQUENCE: 49
ggggcagatt tattggggtc                                                20

<210> SEQ ID NO 50
<211> LENGTH: 19
<212> TYPE: DNA
<213> ORGANISM: artificial sequence
<220> FEATURE:
<223> OTHER INFORMATION: sequence targeting polyadenylation site 1

<400> SEQUENCE: 50
ctcatgagga gttagtggt                                                 19

<210> SEQ ID NO 51
<211> LENGTH: 20
<212> TYPE: DNA
<213> ORGANISM: artificial sequence
<220> FEATURE:
<223> OTHER INFORMATION: Sequence INTER blocking antisense
      oligonucleotide

<400> SEQUENCE: 51
gtgacagtgg cctggtcaga                                                20
```